(12) United States Patent
Townsend et al.

(10) Patent No.: US 7,419,963 B2
(45) Date of Patent: Sep. 2, 2008

(54) INDOLE ANTIVIRAL COMPOSITIONS AND METHODS

(76) Inventors: Leroy B. Townsend, 2721 Winter Garden Ct., Ann Arbor, MI (US) 48105; John C. Drach, 1372 Barrister Rd., Ann Arbor, MI (US) 48105

( * ) Notice: Subject to any disclaimer, the term of this patent is extended or adjusted under 35 U.S.C. 154(b) by 312 days.

(21) Appl. No.: 10/959,885

(22) Filed: Oct. 6, 2004

(65) Prior Publication Data

US 2005/0143329 A1 Jun. 30, 2005

Related U.S. Application Data

(60) Provisional application No. 60/509,412, filed on Oct. 7, 2003.

(51) Int. Cl.
*A61K 31/70* (2006.01)
*C07H 19/04* (2006.01)
(52) U.S. Cl. ..................... 514/43; 536/27.13
(58) Field of Classification Search .............. 536/27.13; 514/43
See application file for complete search history.

(56) References Cited

U.S. PATENT DOCUMENTS

| 4,892,865 A | 1/1990 | Townsend et al. |
|---|---|---|
| 4,927,830 A | 5/1990 | Townsend et al. |
| 6,342,501 B1 | 1/2002 | Townsend et al. |
| 6,413,944 B1 | 7/2002 | Townsend et al. |
| 2005/0143329 A1* | 6/2005 | Townsend et al. ............. 514/43 |

FOREIGN PATENT DOCUMENTS

WO PCT/US2004/032895 10/2004

OTHER PUBLICATIONS

[R] Townsend et al., "Synthesis and Antiviral Activity of Some 2-Substituted 3-Formyl- and 3-Cyano-5,6-Dichloroindole Nucleosides," Nucleosides, Nucleotides & Nucleic Acids, 24(10-12), 1613-1626 (2005); only abstract supplied.*
(S) Google search of the term "IC50 and CC50," Sep. 25, 2007, see the circled search result for the definition of the term "selectivity index."*
Townsend, et al., "Design, Synthesis, and Antiviral Activity of Certain 2,5,6-Trihalo-I-(fJ-D-ribofuranosyl)benzimidazoles", J. Med. Chem. 1995, 38, 4098-4105.
Good, et al., "New Micromethod for Titration of DNA Viruses Encoding Thymidine Kinase." Antiviral Res. 1994, 23(S), 103.
Chen, et al., "Synthesis and Antiviral Evaluation of Trisubstituted Indole N-Nucleosides as Analogues of 2,5,6-Trichloro-I-(p-D-ribofuranosyl)benzimidazole (TCRB)", J. Med. Chem. 2000, 43, 2449-2456.
Chen, J. J., "Synthetic Studies of Some Pyrazine, Indole, and Quinoline Nucleosides", Ph. D. thesis: Department of Chemistry; University of Michigan: Ann Arbor, MI, 1998.
Prichard, et al., "A three-dimensional model to analyze' drug-drug interactions", Antiviral Res. 1990, 14, 181-206.

Migawa, et al., "Design, Synthesis, and Antiviral Activity of a-Nucleosides: D- and L-Isomers of Lyxofuranosyl- and (5-Deoxylyxofuranosyl)benzimidazoles", J. Med. Chem. 1998, 41, 1242-1251.
Biron, et al., "Potent and Selective Inhibition of Human Cytomegalovirus Replication by 1263W94, a Benzimidazole L-Riboside with a Unique Mode of Action", Agents Chemother. 2002, 46, 2365-2372.
Monge, et al., "New 5H-I,2,4-triazino[5,6-b]indole and aminoindole derivatives. Synthesis and studies as inhibitors of blood platelet aggregation, anti-hypertensive agents and thromboxane synthetase inhibitors", Eur. J. Med. Chem. 1991, 26, 179-188.
Ruccia, et al., "Addition Reactions of Heterocycles-IV Indoles and Nitrilimines", Tetrahedron 1973, 29, 3159-3164.
Laude, et al., "Cycloadditions dipolaires-I ,3 II. Addition des diarylnitrilimines au N-methylindole. Etude experimentale et essai d'interpretation", J. Heterocyclic Chem. 1977, 14, 1183-1189.
Kiselyov, et al., "Acylation of Activated Aromatic Substrates under !\lild Conditions with (RCOhO/ MezS/BFJ", Tetrahedron Lett. 1995, 36, 4005-4008.
Deutsch, et al., "Synthesis and Pharmacology of Site-Specific Cocaine Abuse Treatment Agents: The Role of the Phenyl Group in Highly Modified Methylphenidate Analogs as Dopamine Uptake Inhibitors", Med. Chem. Res. 1999, 9, 213-222.
Cocker, et al., "Reactions of Some Dicarbonyl Compounds. Part 111. 1 Oxidation of Some [3-Diketones with Alkaline Hydrogen Peroxide", J. Chem. Soc. Perkin I 1975, 1347-1352.
Rosemeyer, et al., "171. Stereoselective Synthesis of Pyrrolo[2,3-d]pyrimidine ~- and p-n-Ribonucleosides from Anomerically Pure n-Ribofuranosyl Chlorides: Solid-Liquid Phase-Transfer Glycosylation and 15N-NMR Spectra", Helv. Chim. Acta 1988, 71, 1573-1585.
Wilcox, et al., "Steroselective Preparations of Ribofuranosyl Chlorides and Ribofuranosyl Acetates. Solvent Effects and Stereo selectivity In the Reaction of Ribofuranosyl Acetates with Trimethylallylsilane", Tetrahedron Lett. 1986, 27, 1011-1014.
Rolland, et al., "Convenient Preparation of 2•Deoxy3,5.di•O•p•Toluoyl.a.n•erythro•Pentofuranosyl Chloride", Synth. Commun. 1997, 27, 3505-3511.
Cao, et al. "Structure of Lumazine N 1-(2'-Deoxy-n-ribonucleosides) ( =1-(2'-Deoxy-n-ribofuranosyl)pteridine-2,4(IH,3H)-diones): A Revision of the Anomeric Configuration", Helv. Chim. Acta 1992, 75, 1267-1273.
Miyaura, et al., "The Palladium-Catalyzed Cross-Coupling Reaction of Phenylboronic Acid With Haloarenes in the Presence of Bases", Synth. Commun. 1981, 11, 513-519.

(Continued)

*Primary Examiner*—L. E. Crane

(57) ABSTRACT

The present invention provides novel chemical compounds, and methods for their use. In particular, the present invention provides indole derivatives (e.g. as shown in Formula (I)) and related compounds and methods of using indole derivatives and related compounds as therapeutic agents to treat a number of conditions, including those associated with viral infection and cardiovascular diseases.

11 Claims, 18 Drawing Sheets

OTHER PUBLICATIONS

Echavarren, et al., "Palladium-Catalyzed Coupling of Aryl Triflates with Organostannanes", J. Am. Chem. Soc. 1987, 109, 5478-5486.

Huff, et al., "Synthesis of Unsymmetrical Biaryls Using a Modified Suzuki Cross-Coupling: 4-Biphenylcarboxaldehyde". In Organic Syntheses, vol. 75; Smith, A. B., III Ed.; American Chemical Society: Washington, DC, 1997; pp. 53-60.

Bunce, et al., "ArYI-Fused Nitrogen Heterocycles by a ITandem Reduction—Michael Addition Reaction", J. Org. Chem. 2000, 65, 2847-2850.

Bellamy, et al., "Selective Reduction of Aromatic Nitro Compounds With Stannous Chloride in Non Acidic and Non 'Aqueous Medium", Tetrahedron Lett. 1984, 25, 839-842.

Usui, et al., "Adaptation of the Photo-Induced [1,3]-Allylic Phenylthio Shift to the Preparation of Functionalized Diquinanes", Tetrahedron Lett. 1969, 40, 3495-3498.

Lal, et al., "Bis(2-methoxyethyl)aminosulfur Trifluoride: A New Broad-Spectrum Deoxofluorinating Agent with Enhanced Thermal Stability", J. Org. Chem. 1999, 64, 7048-7054.

Ottoni, et al., "Acylation of Indole under Friedel-Crafts Conditions—An Improved Method To Obtain 3-Acylindoles Regioselectively", Organic Letters 2001, 3, 1005-1007.

Ugarkar, et al., "Adenosine Kinase Inhibitors. 2. Synthesis, Enzyme Inhibition, and Antiseizure Activity of Diaryltubercidin Analogues" J. Med. Chem. 2000, 43, 2894-2904.

Shipman, et al., "Antiviral Activity of Arabinosyladenine and Arabinosylhypoxanthine in Herpes Simplex Virus-Infected KB Cells: Selective Inhibition of Viral Deoxyribonucleic Acid Synthesis in Synchronized Suspension Cultures", Antimicrob. Agents Chemother. 1976, 9, 120-127.

Turk, et al., "Pyrrolo[2,3-d]Pyrimidine Nucleosides as Inhibitors of Human Cytomegalovirus", Agents Chemother. 1987, 31, 544-550.

Prichard, et al., "A microtiter virus yield reduction assay for the evaluation of antiviral compounds against human cytomegalovirus and herpes simplex virus", J. Virol. Methods 1990, 28, 101-106.

Prichard, et al., "Three-Dimensional Analysis of the Synergistic Cytotoxicity of Ganciclovir and Zidovudine", Antimicrobial Agents & Chemotherapy, 1991, vol. 35, pp. 1060-1065.

Cavrini, et al., Study on Substance of Antiviral Activity. Part XIII. Synthesis and Activity in vitro of 1-Benzoyl- and 1-Benzyl-2-chloro-3-formylindole Thiosemicarbazones. Farmaco, Edizione Scientifica. 1980, vol. 35, No. 8, pp. 636-641.

Andreani, et al., "Studies on Antiviral Substances. IX. Synthesis and Antiviral Activity of 1-Acyl-2-halo-3-formylindole Semicarbazones." Farmaco, Edizione Scientifica. 1978, vol. 33, No. 10, pp. 754-760.

Andreani, et al., "Substances with Antiviral Activity. II. Derivatives of N-Substituted 2-chloro-3-formylindoles." Farmaco, Edizione Scientifica. 1974, vol. 30, No. 6, pp. 440-448.

* cited by examiner

A. TCRB and structurally related indole nucleosides.

4.1           4.2           4.3 R = CHO
                                                 4.4 R = CN
                                                 4.5 R = $CONH_2$

B. Modifications of indole nucleosides.

4.3

A. Synthesis of 2-monoalkylamine-substituted indole nucleosides.

B. Synthesis of 2-thiomethyl derivatives and synthesis of 2-methoxy derivatives.

Synthesis of 3-modified indole nucleosides: condensation of 3-aldehyde.

Synthesis of 3-modified indole nucleosides: condensation of 3-nitrile.

A. Synthesis of 3-modified indole nucleosides: 3-acyl indoles.

B. Synthesis of 3-modified indole nucleoside precursor: 2,5,6-trichloro-3-methylindole.

Synthesis of 3-modified indole nucleosides: glycosylation of 2,5,6-trichloro-3-methylindole.

Synthesis of 3-modified indole nucleosides: glycosylation of 2,5,6-trichloro-3-haloindoles.

Synthesis of sugar-modified indole nucleosides: 5'-deoxyribofuranoside.

Synthesis of sugar-modified indole nucleosides: 5'-deoxy-5'-fluororibofuranoside.

Synthesis of sugar-modified indole nucleosides: 2'-deoxyribofuranoside.

Synthesis of sugar-modified indole nucleosides: 5'-O-acyl-ribofuranosides.

US 7,419,963 B2

INDOLE ANTIVIRAL COMPOSITIONS AND METHODS

The present application claims priority to U.S. Provisional Application Ser. No. 60/509,412 filed Oct. 7, 2003, which is herein incorporated by reference in its entirety.

The present application was funded in part with government support under grant number U19-AI31718 and P01-AI46390 from the National Institutes of Health, National Institute of Allergy and Infectious Diseases. The government has certain rights in this invention.

FIELD OF THE INVENTION

The present invention relates to novel chemical compounds, and methods for their use. In particular, the present invention provides indole derivatives (e.g. as shown in Formula (I)) and related compounds and methods of using indole derivatives and related compounds as therapeutic agents to treat a number of conditions, including those associated with viral infection and cardiovascular diseases.

BACKGROUND OF THE INVENTION

The herpesviruses comprise a large family of double stranded DNA viruses. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans. Several of these viruses are important human pathogens. HSV-1 is estimated to affect 100 million people in the U.S. Primary infection of HSV-1 usually occurs between the ages of one and four. Cold sores, the visible symptom, typically appear at a later age, with 20-45% of the population over the age of fifteen affected (see, Whitley, Clin. Intect. Dis., 26:541-555, 1998, herein incorporated by refeence). Genital herpes (HSV-2) is the second most common sexually transmitted disease, with approximately 22% of the U.S population infected with this virus. VZV is the causative agent of chicken pox upon primary infection and can recur in adults as zoster. EBV results in approximately two million cases of infectious mononucleosis in the U.S. each year. It can also cause lymphomas in immunocompromised patients and has been associated with Burkitt's lymphoma, nasopharyngeal carcinoma, and Hodgkins disease. Infection with HCMV often occurs during childhood and is typically asymptomatic except in immunocompriomised patients where it causes significant morbidity and mortality. HHV-6 is the causitive agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

These viruses are capable of residing in a latent state within the host. Reactivation of latent virus results from response to environmental stimuli (ex. UV exposure, stress, etc.). Infections or recurrence can be life threatening in immunocompromised patients such as AIDS or transplant patients where HCMV can result in retinitis, pneumonia, and gastrointestinal disease. What is needed, therefore, are compounds capable of treating and/or preventing infection with one or more of these viruses.

SUMMARY OF THE INVENTION

The present invention provides novel chemical compounds, and methods for their therapeutic use. In particular, the present invention provides indole derivatives and related compounds and methods of using indole derivatives and related compounds as therapeutic agents to treat a number of conditions associated with viral infection and cardiovascular disease.

In some embodiments, the present invention provides compositions comprising a compound as depicted in formula (I), wherein formula (I) is as follows:

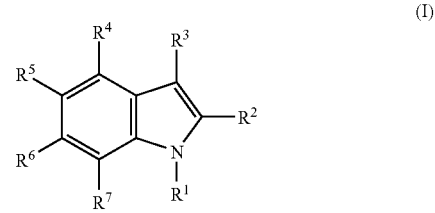

(I)

and wherein: $R^1$ is alkyl, alkenyl, aralkyl, polyhydroxyalkyl, or carbohydrate; $R^2$ is halogen, —N, $R^9$, —O—$R^{10}$, or —S—$R^{11}$; $R^3$ is CN, C=$NR^{12}$, CXNH$_2$, COR, CH$_2$COR—COR$^{13}$, halogen, exocyclic heterocycle, or NO$_2$; and $R^4$, $R^5$, $R^6$, $R^7$ are hydrogen, halogen, nitro, or azido ($R^9$—$R^{13}$ and remaining R groups described in examples below). In particular embodiments, $R^3$ is not CHO, CN, or CONH$_2$. It is noted that Formula I is not limited to any particular stereochemistry, unless otherwise indicated.

In certain embodiments, $R^1$ is alkyl $C_{1-10}$; alkenyl $C_{1-10}$; aryl $C_{1-10}$, including heteroaryl; hydroxyethoxymethoxy (HEM), dihydroxypropoxymethyl (DHPM); pentofuranosyl and pentopyranosyl (D or L) (α or β), tetrafuranosyl (D or L) (α or β); $R^2$ is —$NR^8R^9$ where $R^8$ and $R^9$ may be different or the same and selected from alkyl ($C_{1-10}$), alkenyl ($C_{1-10}$), aryl, heteroaryl, arylalkyl; halogen (e.g., chloro, bromo), cyano, mercaptan, alkylmercaptan, ($C_{1-10}$), alkoxy ($C_{1-10}$); $R^3$ is cyano, C=$NR^{12}$ where $R^{12}$ may be alkyl, alkylamine, urea, thiourea; —CXNH$_2$ where X may be =S, =O, =NH, =N—NH$_2$, =NOH, =N—NHR; —RC=O where R may be H, alkyl ($C_{1-10}$); —CH$_2$—C—R where R may be H, alkyl ($C_{1-10}$); heterocycle, e.g., thiophine, furan, imidazole, tetrazole, imidazolidine, thiazole, triazole; or nitro; and $R^4$—$R^7$ are halogen (chloro, bromo, fluoro, iodo) where $R^4$—$R^7$ may be the same or different halo groups or hydrogen; $R^4$—$R^7$ may be nitro groups or azido group with halogens in different juxtapositions, or $R^4$—$R^7$ may also represent different alkyl ($C_{1-6}$) groups in with the halogens, nitro and azido groups.

In other embodiments, $R^1$ is D or L-ribose, D or L-xylose, D or L-arabinose, D or L-lyxose, D or L-erythrose, D or L threose; also the 2-deoxy, 3-deoxy, 5-deoxy and 2,3-dideoxy derivatives of the above, also the α or β-anomers of both categories described above; alkyl (C1-10) e.g., methyl, ethyl, propyl; aralkyl, e.g., benzyl, phenethyl, substituted benzyl, substituted phenethyl; heteroaryl, e.g., picolylmethyl; HEM (hydroxyethoxymethoxy), DHPM (dihydroxypropoxymethyl), or structural variations of HEM & DHPM; $R^2$ is $NR^8R^9$ where $R^8$=$R^9$ H, CH$_3$, C$_2$H$_5$ isopropyl, cyclopropyl; halogen, chloro, bromo; —O—$R^{10}$ where $R^{10}$=CH$_3$, C$_2$H$_5$, CH$_2$C$_6$H$_5$; —S—$R^{11}$ where $R^{11}$=H, CH$_3$, C$_2$H$_5$, or CH$_2$C$_6$H$_5$; $R^3$ is cyano; C=$NR^{12}$ where $R^{12}$ urea, substituted urea, thiourea, substituted thiourea; —CXNH$_2$ where X is =O, =S, =NOH, =N—NH$_2$; —CR=O where R is H, CH$_3$, C$_2$H$_5$, C$_3$H$_7$; —CH$_2$—RC=O where R is H, CH$_3$, C$_2$H$_5$, C$_3$H$_7$; or exocyclic heterocycles; and $R^4$—$R^7$ are selected variations of substitution using the halo groups Cl, Br, F or I and the nitro and azido groups.

In certain embodiments, $R^1$ is D-ribofuranosyl, 2'-deoxy-D-ribofuranosyl, 5'-O-acetyl-D-ribofuranosyl, 5'-O-acetyl-2'-deoxy-D-ribofuranosyl, 2',3',5'-tri-O-acetyl-D-ribofuranosyl, 3'-5'-di-O-acetyl-2'-deoxy-D-ribofuranosyl; or 5'-deoxy-D-ribofuranosyl, 2',3'-di-O-acetyl-5'-deoxy-D-ribofuranosyl; $R^2$ is —$NR^8R^9$ where $R^8$=$R^9$=H, $CH_3$, $C_2H_5$, $R^8$=H$R^9$=isopropyl or cyclopropyl; where $R^2$=Cl, Br; $R^3$ is Cyano; C=$NR^{12}$ where $R^{12}$=urea, thiourea; —CXNH$_2$ where X is =O, =S, =NOH, =N—HN—R; —RC=O where R=H, $CH_3$, $C_2H_5$, $C_3H_7$; thienyl, or furyl; and $R^4$—$R^7$ are exocyclic groups selected from chloro, bromo, hydrogen or nitro groups.

In some embodiments, the compound is selected from the group consisting of compound 4.33, compound 4.46, compound 4.97, compound 4.117, compound 4.122, compound 4.137, compound 4.140, and compound 4.143. In certain embodiments, the compound is selected from compounds 4.6-4.143. In other embodiments, the compound has antiviral activity. In particular embodiments, the selectivity index (calculated by dividing the $CC_{50}$ by the $IC_{50}$) of the compound (against viruses) is at least 85 (e.g. at least 85, at least 90, at least 95, at least 100, at least 110, at least 125, at least 150, at least 170, at least 190). In further embodiments, the selectivity index (calculated by dividing the $CC_{50}$ by the $IC_{50}$) is between 85 and 195 (e.g. 85-195, 95-175, 100-150, or other ranges). In certain embodiments, the composition further comprises a pharmaceutically acceptable carrier or a pharmaceutically acceptable derivative.

In some embodiments, the present invention provides a prodrug of a compound as depicted in formula (I), wherein formula (I) is as follows:

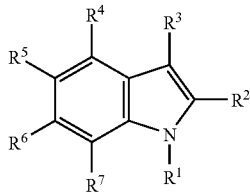

(I)

and wherein: $R^1$ is alkyl, alkenyl, aralkyl, polyhydroxyalkyl, or carbohydrate; $R^2$ is halogen, —N, $R^9$, —O—$R^{10}$, or —S—$R^{11}$; $R^3$ is CN, C=$NR^{12}$, CXNH$_2$, COR CH$_2$COR—$COR^{13}$, halogen, exocyclic heterocycle, or $NO_2$; and $R^4$, $R^5$, $R^6$, $R^7$ are hydrogen, halogen, nitro, or azido. It is noted that Formula I is not limited to any particular stereochemistry, unless otherwise indicated.

In other embodiments, the present invention provides methods comprising; a) providing; i) a patient with symptoms of viral or retroviral infection; and ii) a composition comprising a compound as depicted in formula (I), wherein formula (I) is as follows:

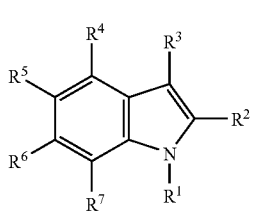

(I)

and wherein: $R^1$ is alkyl, alkenyl, aralkyl, polyhydroxyalkyl, or carbohydrate; $R^2$ is halogen, —N, $R^9$, —O—$R^{10}$, or —S—$R^{11}$; $R^3$ is CN, C=$NR^{12}$, CXNH$_2$, COR CH$_2$COR—$COR^{13}$, halogen, exocyclic heterocycle, or $NO_2$; and $R^4$, $R^5$, $R^6$, $R^7$ are hydrogen, halogen, nitro, or azido, and b) administering the composition to the patient under conditions such that at least one of the symptoms of viral or retroviral infection is reduced or eliminated.

In other embodiments, the viral infection is selected from the group consisting of herpes virus infection, pox virus infection, and hepatitis virus infection. In some embodiments, the viral infection is selected from the group consisting of cytomegalovirus infection, hepatitis B virus infection, herpes simplex virus type 1 infection, herpes simplex virus type 2 infection, varicella zoster virus infection, Epstein Barr virus infection, human herpes virus 6 infection, human herpes virus 7 infection, human herpes virus 8 infection, and hepatitis C virus infection.

In particular embodiments, the present invention provides methods comprising; a) providing; i) a patient with symptoms of cardiovascular disease (e.g., restenosis); and ii) a composition comprising a compound as depicted in formula (I), wherein formula (I) comprises:

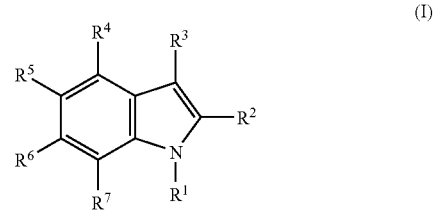

(I)

and wherein: $R^1$ is alkyl, alkenyl, aralkyl, polyhydroxyalkyl, or carbohydrate; $R^2$ is halogen, —N, $R^9$, —O—$R^{10}$, or —S—$R^{11}$; $R^3$ is CN, C=$NR^{12}$, CXNH$_2$, COR CH$_2$COR—$COR^{13}$, halogen, exocyclic heterocycle, or $NO_2$; and $R^4$, $R^5$, $R^6$, $R^7$ are hydrogen, halogen, nitro, or azido, and b) administering the composition to the patient under conditions such that at least one of the symptoms of the cardiovascular disease (e.g., restenosis) is reduced or eliminated.

In certain embodiments, the administering is conducted after a surgical procedure has been performed on the patient. In further embodiments, the administering is conducted following angioplasty in the patient. In certain embodiments, the present invention provides one or more stents (e.g. for cardiovascular procedures) comprising a compound of Formula (I) (e.g. a stent coated with the compound of Formula (I)). The further embodiments, the indole compounds of the present invention (e.g. as shown in Formula (I)) can be packaged into a kit, which may include instructions for administering the compounds to a subject.

In some embodiments, the present invention provides a compound as shown in Formula I as a medicament. In certain embodiments, the present invention provides a method of treting viral or retroviral infection, or cardiovascular disease in a subject, where the method comprises administering the subject an effective amount of a compound of Formula I or pharmaceutically acceptable satl thereof. In other embodiments, the present invention provides the use of compounds of Formula I in the manufacture of a medicament for the treatment of viral, retroviral, or cardiovascular diseases. In some embodiments, the present invention provides a pharmaceutical for the treatment of viral, retroviral or cardiovascular disease characterized in that it contains compounds of Formula I as an active substance. In particular embodiments, the present invention provides a compound of Formula I for the preparation of a composition for the treatment of viral, retroviral or cardiovascular disease.

DEFINITIONS

Figure 1:
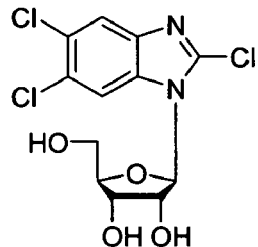
FIG. 1A shows TCRB and structurally related nucleosides.
FIG. 1B shows modifications of indole nucleosides.
Figure 1:
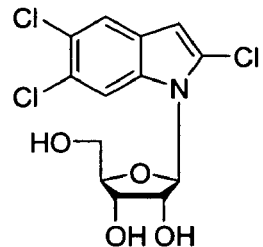
Figure 1:
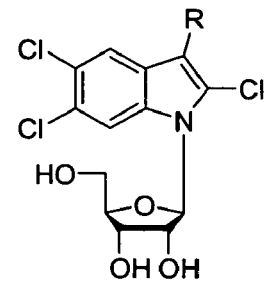
Figure 1:
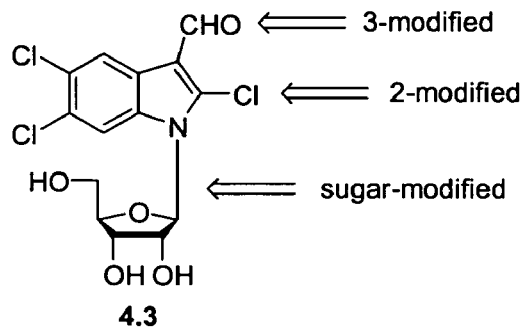

To facilitate an understanding of the invention, a number of terms are defined below.

As used herein, the term "aliphatic" or "aliphatic chain" refers to a class of organic compounds where carbon and hydrogen molecules are arranged in straight or branched chains. The chain may include saturated (e.g., alkanes) or unsaturated (e.g., alkenes and alkynes) elements. Examples include, but are not limited to, ethane, ethene, ethyne, octane, 2-octene, 2-octyne, pentadecane, hexadecane, and eicosane.

As used herein, the term "substituted aliphatic" or "substituted aliphatic chain" refers to an aliphatic chain where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of no more than three fused rings at least one of which is aromatic, and where at least one of the hydrogen atoms on a ring carbon has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to a cycloalkane or a fused ring system consisting of at least one fused cycloaliphatic ring. Examples of such include, but are not limited to, decalin and the like.

As used herein, the term "substituted cycloaliphatic" refers to a cycloalkane or a fused ring system consisting of at least one fused ring, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl and the like.

As used herein, the term "heterocyclic" refers to a cycloalkane and/or an aryl ring system and/or a fused ring system consisting of at least one fused ring, where at least one of the ring carbon atoms is replaced by oxygen, nitrogen or sulfur. Examples of such include, but are not limited to, morpholino and the like.

As used herein, the term "substituted heterocyclic" refers to a cycloalkane and/or an aryl ring system and/or a fused ring system consisting of at least one fused ring, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 3-chloropyranyl.

As used herein, the term "nitro" or "nitro subgroup" refers to an $NO_2$ subgroup. Examples of compounds containing nitro subgroups include, but are not limited to, nitrobenzene.

As used herein, the term "linker" refers to a chain containing at least two contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acylamino" is an amino group that has been acylated. Examples of such include, but are not limited to, acetamide and the like.

As used herein, the term "subject" or "patient" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of indole compound(s), such as shown in Formula (I), and optionally one or more other agents) for a condition characterized by viral infection, cardiovascular disease or other condition.

As used herein, the term "virus" refers to obligate intracellular parasites of replicating but noncellular nature. Examples include, but are not limited to, HIV-1, HTLV-1, human herpes virus 6, and hepatitis A virus.

As used herein, the term "retrovirus" refers to any virus in the family Retroviridae that has RNA has its nucleic acid and uses the enzyme reverse transcriptase to copy its genome into the DNA of the host cell chromosomes.

As used herein, the term "viral disease" or "viral infection" or "viral disorder" or "viral condition" refer to any disease, infection, condition, or disorder caused or exacerbated by a virus. Examples include, but are not limited to, human immunodeficiency virus-1 (HIV-1), acquired immunodeficiency syndrome (AIDS), herpes simplex virus (HSV), varicella zoster virus (VZV), respiratory syncytial virus (RSV) and cytomegalovirus (CMV).

As used herein, the term "retroviral disease" or "retroviral infection" or "retroviral disorder" or "retroviral condition" refer to any disease, infection, condition, or disorder caused or exacerbated by a retrovirus. Examples include, but are not limited, AIDS, T-cell leukemia, and T-cell lymphoma.

As used herein, the terms "antiviral agent," or "conventional antiviral agent" refer to any chemotherapeutic compounds used in the treatment of viral disorders. Examples include, but are not limited to, Agenerase (amprenavir), Combivir, Crixivan (indinavir), Epivir (3TC/lamivudine), Emtriva (emtricitabine (FTC)), Fortovase (saquinavir), Fuzeon (enfuvirtide), Hivid (ddc/zalcitabine), Hydrea (hydroxyurea), Invirase (saquinavir), Kaletra (lopinavir), Norvir (ritonavir), Rescriptor (delavirdine), Retrovir, AZT (zidovudine), Reyataz (atazanavir), Sustiva (efavirenz), Trizivir, Videx, Videx EC (ddI/didanosine), Viracept (nelfinavir), Viramune (nevirapine), Viread (tenofovir disoproxil flimarate), Zerit (d4T/stavudine), and Ziagen (abacavir). Such compounds can be combined with the indole compounds described herein (e.g. as shown in Formula (I)).

As used herein, the term "effective amount" refers to the amount of a compound (e.g., indole compound, such as in Formula (I)) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., indole compounds such as in formula (I)) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]). Such pharmaceutically acceptable carriers can be combined with the indole compounds described herein (e.g. as shown in Formula (I)).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions characterized by viral infection (e.g., providing dosing, route of administration, decision trees for treating physicians for correlating patient-specific characteristics with therapeutic courses of action). The indole compounds of the present invention (e.g. as shown in Formula (I)) can be packaged into a kit, which may include instructions for administering the compounds to a subject.

General Description

The present invention provides novel chemical compounds, and methods for their use. In particular, the present invention provides indole derivatives (e.g. as shown in Formula (I)) and related compounds and methods of using indole derivatives and related compounds as therapeutic agents to treat a number of conditions, including those associated with viral infection and cardiovascular diseases.

A compound of the Formula I can be administered to an individual for the treatment of a variety of clinical conditions including, for example, the treatment and prophylaxis of viral infection or cardiovascular disorders or complications associated, for example, with infection or surgery. Examples of viral infections include: herpes virus infection, pox virus infection, hepatitis virus infection, cytomegalovirus infection, hepatitis B virus infection, herpes simplex virus type 1 infection, herpes simplex virus type 2 infection, varicella zoster virus infection, Epstein Barr virus infection, human herpes virus 6 infection, human herpes virus 7 infection, human herpes virus 8 infection, and hepatitis C virus infection. Examples of cardiovascular disorders include restenosis, for example restenosis following angioplasty, reocclusion prophylaxis including reocclusion prophylaxis following lysis or dilatation (PTCA), conditions after coronary bypass operations, arterial, venous and microcirculatory disease states, cardiac infarction, angina pectoris including unstable angina pectoris, thromboembolic diseases, thromboses, embolism, adult respiratory distress syndrome, multi-organ failure, stroke and disseminated intravascular coagulation clotting disorder. Examples of related complications associated with surgery include, for example, deep vein and proximal vein thrombosis, which can occur following surgery. In certain embodiments, a compound of the invention is useful as a medicament for reducing or inhibiting or preventing unwanted coagulation or blood clotting or thrombus formation in an individual.

The compounds of the Formula I, their physiologically acceptable salts and other suitable derivatives thereof like prodrugs can be administered as medicaments or pharmaceuticals for the above mentioned conditions (or other conditions) for the treatment or prophylaxis on their own, in mixtures with each other or in the form of pharmaceutical compositions which comprise, as the active ingredient, an effective amount of at least one compound of the Formula I and/or of a physiologically acceptable salt and/or another suitable derivative thereof in admixture or otherwise in association with a pharmaceutically acceptable carrier.

In effecting treatment of a patient, compounds of the Formula I or pharmaceutical compositions comprising them can be administered in any form or mode which makes the compounds of the formula I bioavailable in effective amounts, including oral and parenteral routes. For example, they can be administered orally, subcutaneously, intramuscularly, intravenously, transdermally, intranasally, rectally, and the like. Oral administration is generally preferred but depending on the specific case other modes of administration can also be favorable, for example in an acute stage of a disease intravenous administration by means of injection or infusion. One skilled in the art can readily select the proper form and mode of administration depending upon the disease state to be treated, the stage of the disease, and other relevant circumstances.

Pharmaceutical compositions or medicaments comprising a compound of the Formula I and/or a physiologically acceptable salt and/or another suitable derivative thereof can be made by combining by standard procedures the compounds of the Formula I and/or their physiologically acceptable salts and/or other suitable derivatives thereof with one or more pharmaceutically acceptable carrier substances and/or auxiliary substances the proportion and nature of which are determined by the chosen route of administration and standard pharmaceutical practice. The pharmaceutical compositions or medicaments are prepared in a manner well known in the pharmaceutical art. The pharmaceutical compositions will, in general, contain an effective amount of one or more compounds of the Formula I and/or their physiologically acceptable salt and/or other suitable derivatives thereof together with a suitable amount of a carrier so as to comprise the proper dosage for administration to an individual. The pharmaceutical compositions may be adapted for oral or parenteral use and may be administered to the patient in the form of, for example, tablets, capsules, suppositories, solutions, suspensions, ointments, tinctures, nasal sprays, aerosol mixtures, implants, rods, microcapsules or the like. The present invention further encompasses a process for the preparation of pharmaceutical compositions or medicaments which comprise at least one compound of the formula I and/or a physiologically acceptable salt and/or another suitable derivative thereof, as well as it encompasses the use of the compounds of the formula I and/or physiologically acceptable salts and/or other suitable derivatives thereof for the preparation of medicaments, especially of medicaments for the treatment or prophylaxis of the above-mentioned diseases.

Pharmaceutically acceptable carrier and auxiliary substances are referred to as substances or compositions that are non-toxic to an individual or have acceptable toxicity (e.g. as determined by the appropriate regulatory agency). The carrier substance or excipient may be a solid, semi-solid, or liquid material which can serve as a vehicle or medium for the active ingredient.

Examples of auxiliary substances are fillers, disintegrants, binders, glidants, wetting agents, stabilizers, emulsifiers, preservatives, sweeteners, dyes, flavorants, aromatizing agents, thickeners, diluents, buffering substances, solubilizing agents, agents for achieving a slow-release effect, salts for altering the osmotic pressure, coating agents, antioxidants, etc.

For the purpose of oral administration, the compounds of the Formula I and/or of their physiologically acceptable salts and/or other suitable derivatives thereof may be incorporated with excipients or inert diluents or edible carriers and used in the form of, for example, tablets, film tablets, coated tablets, pills, troches, capsules, granules, solutions, suspensions, emulsions, elixirs, syrups, wafers, chewing gums and the like, or they may be enclosed in gelatin capsule. The pharmaceutical compositions for oral administration may be varied depending upon the particular form. Usually such pharmaceutical compositions contain at least 1% of the active ingredient of the Formula I and/or of a physiologically acceptable salt and/or another suitable derivative thereof and may conveniently contain up to about 90% of the weight of the unit. Preferably the content of the compounds of the formula I and/or their physiologically acceptable salts and/or other suitable derivatives is from about 4% to about 70% by weight. Preferably the amount of the active ingredient present in the compositions is such that a unit dosage form suitable for administration will be obtained.

The tablets, pills, capsules, troches and the like may also contain, for example, one or more of the following carrier and auxiliary substances: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide. Further, sweetening agents such as sucrose or saccharin may be added or flavoring agents such as peppermint, methyl salicylate or orange flavoring. When the dosage unit form is a capsule, it may contain, in addition to materials of the above type, a liquid carrier such as polyethylene glycol or a fatty oil. Other dosage unit forms may contain various other materials which modify the physical form of the dosage unit, for example, as coatings. Thus, tablets or pills may be coated with sugar, shellac, or other enteric coating agents. A syrup may contain, in addition to the active ingredient, for example sucrose as a sweetening agent and certain preservatives, dyes and colorings and flavors.

For the purpose of, for example, parenteral administration the compounds of the Formula I and/or physiologically acceptable salts thereof and/or other suitable derivatives thereof may be incorporated into a solution or a suspension. The solutions or suspensions may, for example, also include one or more of the following carrier and auxiliary substances: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates; agents for the adjustment of toxicity such as sodium chloride or dextrose. The content of the compounds of the formula I and/or of their physiologically acceptable salt and/or other suitable derivatives thereof in the preparations for parenteral adminstration may be varied. Usually they contain at least 0.1% by weight of the compound of the Formula I and/or of a physiologically acceptable salt and/or another suitable derivative thereof and up to 90% by weight. Preferably the content of the compound of the Formula I and/or the physiologically acceptable salts thereof and/or other suitable derivatives thereof is from about 0.1% to 50%. The parenteral preparations can be enclosed, for example, in ampules, disposable syringes, multiple dose vials made of glass or plastic, or infusion bottles. Suitable excipients for microcapsuies, implants and rods are, for example, mixed polymers of glycolic acid and lactic acid.

Generally, the amount of the compounds of the Formula I and/or physiologically acceptable salts thereof and/or other suitable derivatives thereof that is present in a pharmaceutical composition is from about 0.5 mg to about 1 g, preferably from about 1 mg to about 500 mg. Besides one or more compounds of the Formula I and/or one or more physiologically acceptable salts thereof and/or one or more other suitable derivatives thereof as active compounds the pharmaceutical compositions according to present invention may also contain one or more other pharmacologically active compounds. Any materials used in preparing the various pharmaceutical compositions should be pharmaceutically pure and non-toxic in the amounts used.

In another, more general embodiment the present invention provides compositions comprising at least one compound of the Formula I and/or a salt thereof and/or another suitable derivative thereof in admixture or otherwise in association with one or more inert carriers. These compositions are useful, for example, as assay standards, as convenient means of making bulk shipments, as pharmaceutical compositions or as starting materials for the production of pharmaceutical compositions. The amount of a compound of the formula I in such a composition will generally vary from about 0.001% to about 90% by weight. Inert carriers can be any material which does not degrade or otherwise covalently react with a compound of the formula I. Examples of suitable inert carriers are water; aqueous buffers, such as, for example, those which are generally useful in High Performance Liquid Chromatography (HPLC) analysis; organic solvents, such as acetonitrile, ethyl acetate, hexane and the like; and pharmaceutically acceptable carrier and/or auxiliary substances. The compounds of the Formula I can also be used as starting materials or chemical intermediates in the preparation of other compounds, especially in the preparation of other pharmacologically active compounds. Examples for such conversions of compounds of the invention into other compounds of the invention are discussed above and are given in detail below. For this use, besides the compounds of the Formula I and their physiologically acceptable salts also other salts of the compounds of the formula I can be useful which are not suitable or less suitable for use as pharmaceuticals. Thus, the present invention also relates to compounds of the formula I and their salts in general as chemical intermediates, especially as intermediates in the preparation of pharmacologically active compounds. A subject of the invention also are intermediates which are used in the syntheses of the compounds of the formula I described above and below, and their use as chemical intermediates, especially as intermediates in the preparation of pharmacologically active compounds.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); and C (degrees Centigrade).

EXAMPLE 1

Synthesis of Indole Nucleosides

This example describes the indole nucleosides and synthesis of various indole nucleosides. It has been reported reported that the benzimidazole nucleoside 2,5,6-trichloro-1-(β-D-ribofuranosyl)benzimidazole (Townsend, et al., J. Med. Chem. 1995, 38, 4098-4105, herein incorporated by reference; see TCRB, 4.1, FIG. 1A) is a potent and selective inhibitor of human cytomegalovirus (HCMV) replication in vitro. Because of the in vivo instability of TCRB, (Good et al., Antiviral Res. 1994, 23(S), 103, herein incorporated by reference) many analogs of this lead compound have been synthesized in the expectation that certain modifications would increase the glycosidic bond stability while maintaining potency and selectivity. Synthesis of analogs based on a different heterocyclic base has been especially productive.

The alternate heterocycle used in these new syntheses is indole, which resembles benzimidazole with one of the nitrogen atoms replaced by carbon. Surprisingly, 2,5,6-trichloro-1-(β-D-ribofuranosyl)indole (4.2, FIG. 1A), the direct analog of TCRB, was both inactive against HCMV and non-cytotoxic (Chen, et al., J. Med. Chem. 2000, 43, 2449-2456, herein incorporated by reference). However, some derivatives substituted at the 3-position of the indole ring proved to be very active (Chen, J. J. Synthetic Studies of Some Pyrazine, Indole, and Quinoline Nucleosides. Ph. D. thesis: Department of Chemistry; University of Michigan: Ann Arbor, Mich., 1998, herein incorporated by reference). The most potent and selective of these analogs was 2,5,6-trichloro-3-formyl-1-(β-D-ribofuranosyl)indole (4.3, FIG. 1A) with an $IC_{50}$ of 0.23 µM against HCMV and $CC_{50}$ of 45 µM against uninfected host cells. The selectivity index of compound 4.3 is 195 (calculated by dividing the $CC_{50}$ by the $IC_{50}$) is greater than the selectivity index of 82 reported for TCRB (see Tonwsend et al., supra).

Preliminary investigations into the mechanism of antiviral activity suggested that the 3-formyl indole nucleoside 4.3 (FIG. 1A) behaved in a manner similar to that of TCRB. Because compound 4.2, the direct analog of TCRB (4.1) was inactive but the 3-formyl indole nucleoside 4.3, was even more active than TCRB, it was believed that the superior antiviral activity of the 3-substituted indole nucleoside 4.3 (FIG. 1A) could be attributed to the presence of hydrogen bonding at the 3-position of the ring system. Therefore, synthesis and evaluation of a series of indole nucleosides with the intention of increasing the antiviral activity and/or reducing the cytotoxicity with respect to the previously synthesized analogs.

2-Substituted Indole Nucleosides

As is the case for the trichlorobenzimidazole nucleosides (Migawa, et al., J. Med. Chem. 1998, 41, 1242-1251, herein incorporated by reference), the 2-chloro substituent of indoles with electron-withdrawing substituents at the 3-position is susceptible to nucleophilic displacement. Because the benzimidazole nucleoside 1263W94, which contains a substituted amine at the 2-position, is very active against HCMV (Biron et al., Agents Chemother. 2002, 46, 2365-2372), a series of indole nucleoside analogs with mono- and di-alkylamines at the 2-position was planned.

Figure 2:
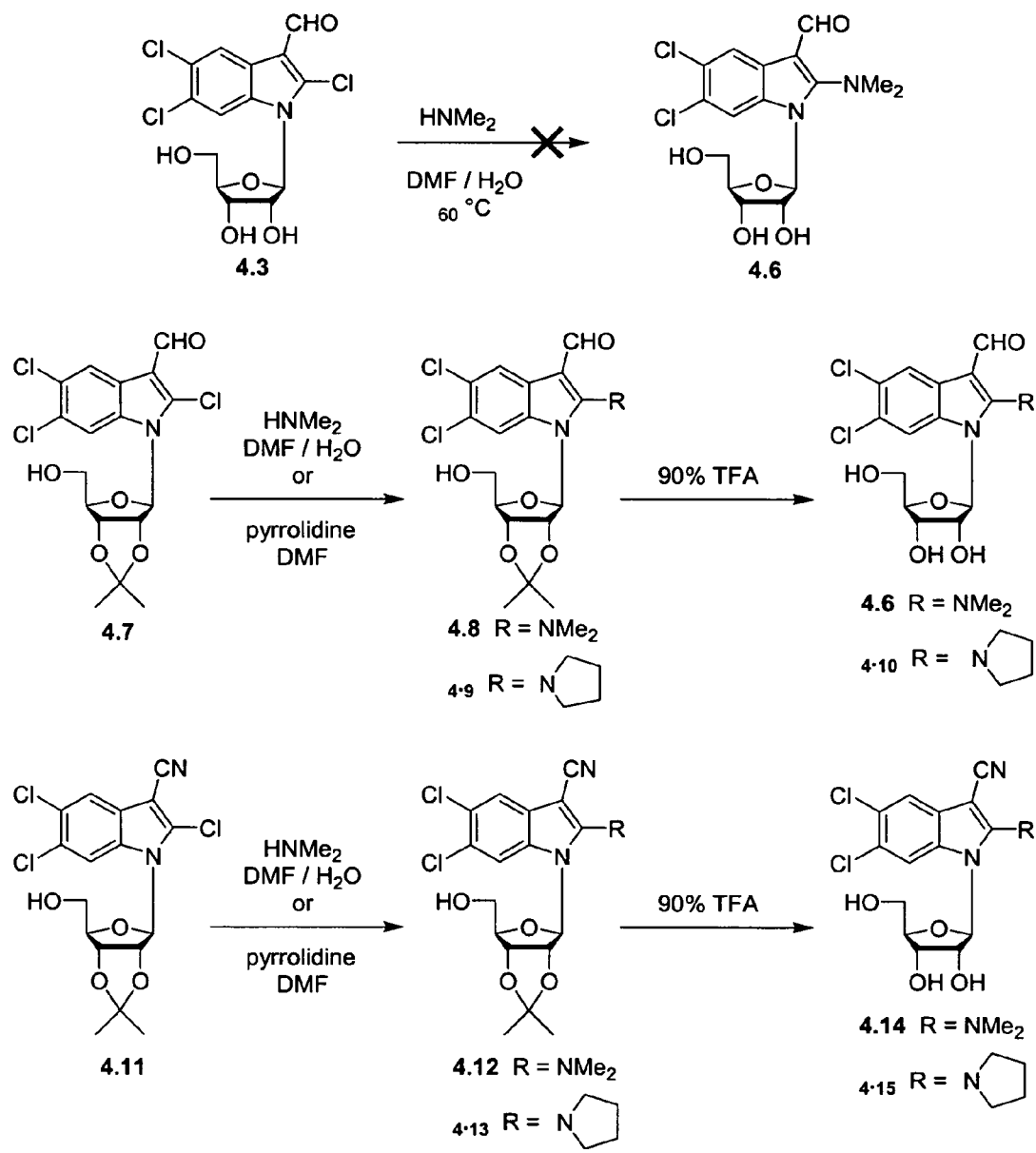
FIG. 2 shows synthesis of 2-dialkylamine-substituted indole nucleosides.

Unexpectedly, the reaction of dimethylamine with the unprotected nucleoside 4.3 (See Chen Thesis, supra) (FIG. 4.2) did not proceed, even at elevated temperatures. However, the reaction of dimethylamine with the isopropylidene protected nucleoside 4.7 (Chen et al., supra) did occur smoothly at room temperature to yield the desired 2-dimethylamino derivative 4.8 (FIG. 2). Compound 4.8 (FIG. 2) was then deprotected by treatment with 90% aqueous trifluoroacetic acid to afford the desired nucleoside analog 5,6-dichloro-2-dimethylamino-3-formyl-1-(β-D-ribofuranosyl)indole (4.6, FIG. 2). The reason for the difference in reactivity between the nucleoside 4.3 and the isopropylidene protected congener 4.7 is unclear, but has been used in later syntheses to guide chemoselectivity. With an efficient method to displace the 2-chloro substituent, other analogs were also pursued. Thus, the protected nucleoside 4.7 was reacted with pyrrolidine to provide the 2-(N-pyrrolidino) derivative 4.10 after deprotection. Reaction of the isopropylidene protected 3-cyano congener (4.11, FIG. 2) also proceeded smoothly under the above reaction conditions to provide both the 2-dimethylamino and 3-(N-pyrrolidino) analogs (4.14 and 41.5, FIG. 2) of the 3-nitrile after deprotection with trifluoroacetic acid.

It was initially assumed that synthesizing the corresponding 2-monoalkylamino compounds would not be straightforward. A synthetic scheme was envisioned that required the use of a "protected" monoalkylamine to avoid the possible complication of imine formation. Thus, it was believed that the reaction of protected indole nucleoside 4.7 with p-methoxybenzylmethylamine would lead to the unsymmetrical 2-dialkylamino derivative 4.17. Compound 4.17 (FIG. 3A) could then be deprotected with 90% aqueous trifluoroacetic acid in the usual manner, followed by DDQ to remove the p-methoxybenzyl protecting group and yield the desired analog 5,6-dichloro-2-methylamino-3-formyl-1-(β-D-ribofuranosyl)indole (4.18, FIG. 3A). Fortuitously, it was discovered that these extra steps were not necessary. In an attempt to synthesize the imine derivative 4.20, the parent nucleoside 4.3 was reacted with a solution of methylamine in ethanol. Surprisingly, it was not the imine that was isolated. Contrary to the trend observed above, in which the 2-chloro substituent of the fully deprotected nucleoside analog 4.3 was resistant to nucleophilic displacement, the only isolated product in this instance was 5,6-dichloro-2-methylamino-3-formyl-1-(β-D-ribofuranosyl)indole (4.18, FIG. 3A). Using this information, the corresponding 2-isopropylamino derivative (4.19, FIG. 3A) was also synthesized.

Figure 3:
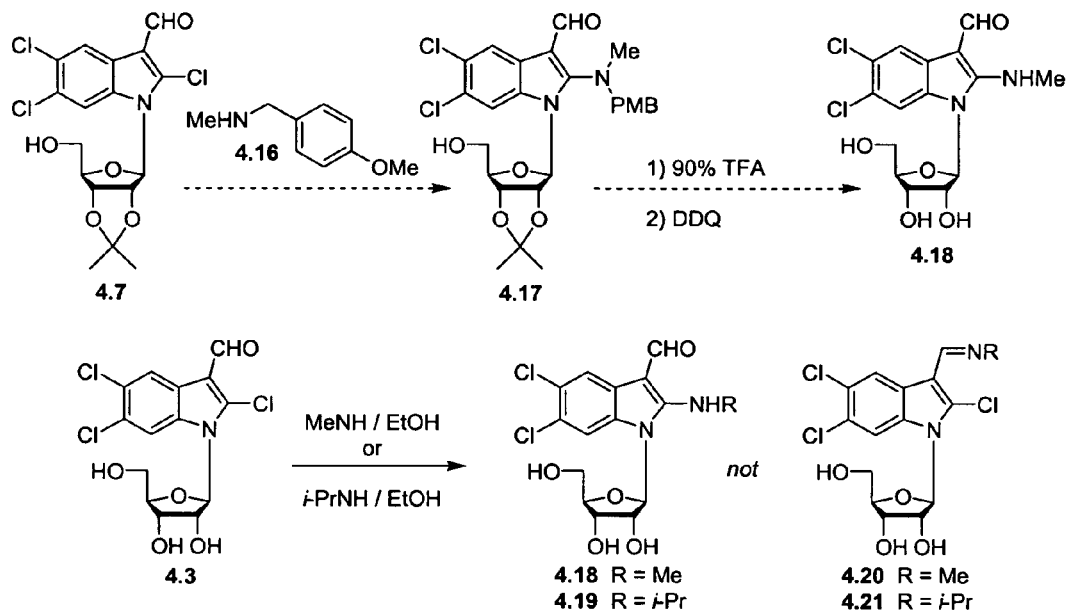
FIG. 3A shows synthesis of 2-monoalkylamine-substituted nucleosides.
FIG. 3B shows synthesis of 2-thioethyl derivatives and synthesis of 2-methoxy derivatives.
Figure 3:
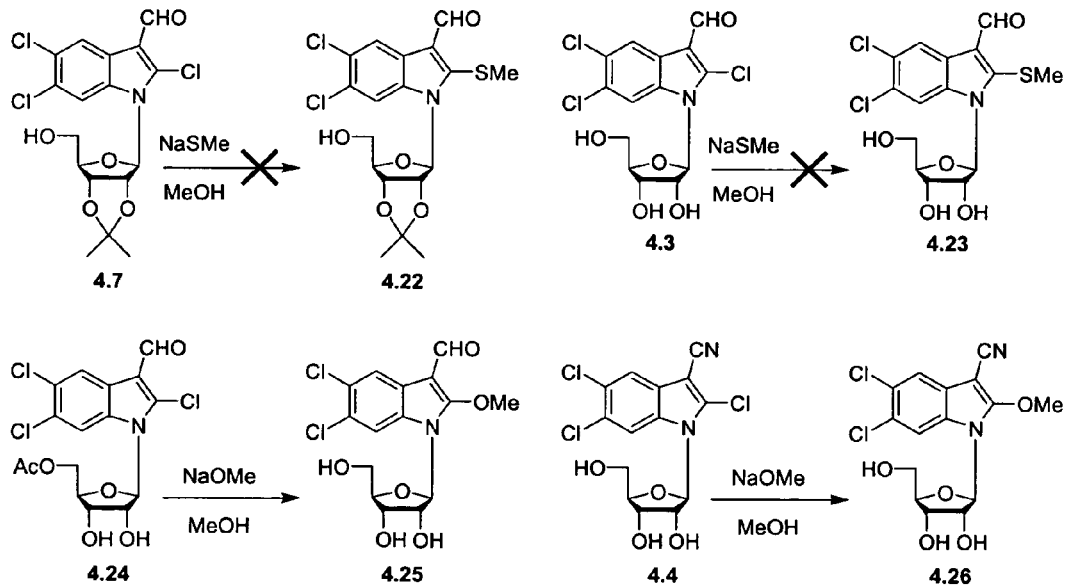

In order to determine whether other 2-substituents would have a beneficial effect on the activity of this series of compounds, the 2-methoxy- and the 2-thiomethoxy-derivatives were also prepared. The desired product was obtained as a by-product during the deprotection of the 5'-O-acetyl riboside 4.24 (FIG. 3B) with an excess of sodium methoxide, although in low yield. Likewise, an attempted synthesis of an imidate under basic conditions led instead to the 2-methoxy derivative 4.26 (FIG. 3B).

3-Substituted Indole Nucleosides

Three general approaches were used to prepare compounds in this class. First, the existing nucleoside analogs 4.3-4.5 (FIG. 1A) were modified directly. Second, modifications of the 3-unsubstituted nucleoside 4.2 (FIG. 1A) and its protected analogs via electrophilic addition were achieved. Third, targets which cannot be synthesized by either of these methods were produced by a synthesis of the appropriate heterocycle, followed by glycosylation and further manipulation of the sugar moiety.

Because aromatic aldehydes and nitriles offer many opportunities for modification, the derivatives 4.3 and 4.4 (FIG. 3B) were well-suited for modification. The aldehyde derivative 2,5,6-trichloro-3-formyl-1-(β-D-ribofuranosyl)indole (4.3, FIG. 4) can undergo addition-dehydration reactions with a number of different amine-containing compounds. The semicarbazone and thiosemicarbazone (4.27 and 4.28, FIG. 4) were synthesized by a reaction of 4.3 (FIG. 4) with semicarbazide and thiosemicarbazide, respectively. The oximes 4.29 and 4.30 (FIG. 4) were produced in a similar manner from hydroxylamine and methoxylamine, respectively. The carbazate 4.31 (FIG. 4) was similarly prepared using methyl hydrazinocarboxylate.

Figure 5:
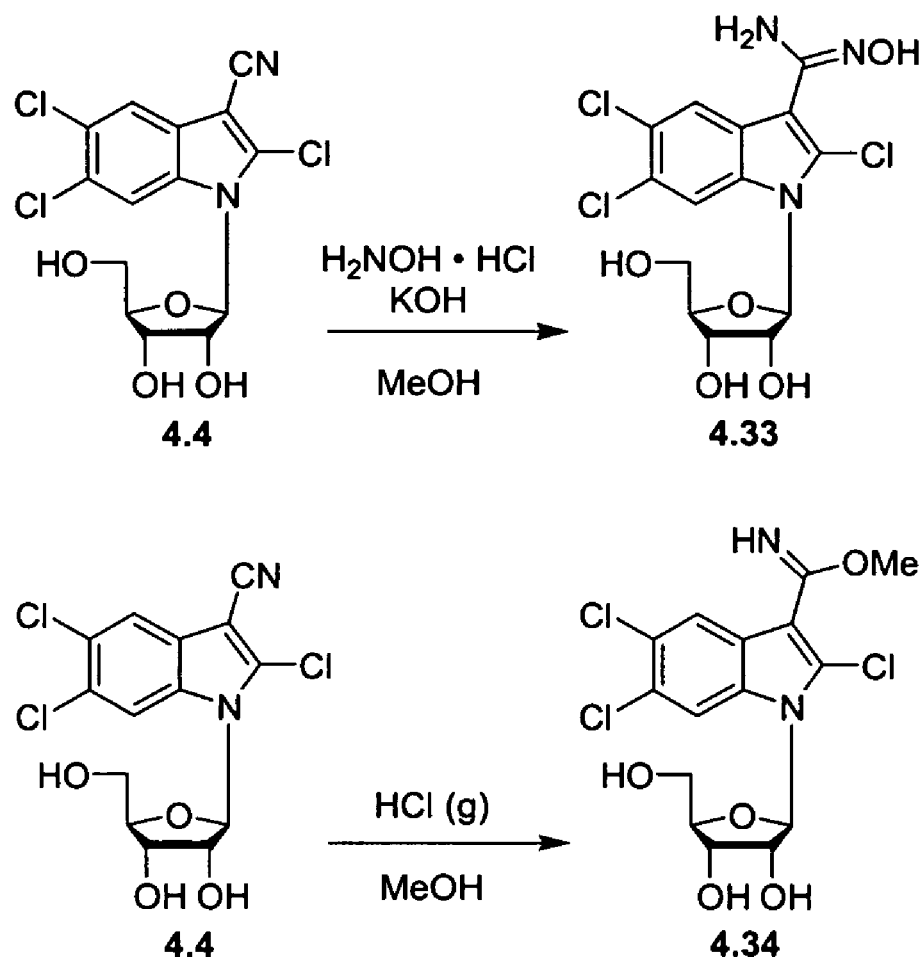
FIG. 5 shows synthesis of 3-modified indole nucleosides: condensation of 3-nitrile.

Aromatic nitriles can also undergo addition reactions with potent nucleophiles or under acid catalysis. The carboxamide oxime 4.33 (FIG. 5) was thus synthesized by a reaction of 2,5,6-trichloro-3-cyano-1-(β-D-ribofuranosyl)indole (4.4, FIG. 5) with hydroxylamine. The imidate 4.34 is an example of the latter strategy, as it is synthesized by a reaction of 4.4 (FIG. 5) with anhydrous methanol and dry HCl gas.

In order to determine whether other acyl substituents (i.e. acetyl, propionyl, etc.) would be tolerated at the 3-position, synthesis of some other acylated derivatives of 4.3 (FIG. 1A) was pursued. The 5'-hydroxyl group of the known intermediate 4.38 (Chen Thesis) (FIG. 6A) was acetylated with acetic anhydride at elevated temperatures. This fully protected nucleoside analog was then subjected to the Vilsmeier-Haack conditions (using dimethyl acetamide). The Vilsmeier-Haack conditions had successfully formylated the indole nucleosides previously (Chen Thesis) using DMF as a solvent, but unfortunately, no reaction occurred under these same conditions with dimethyl acetamide as a solvent. Standard Friedel-Crafts acylation of 4.39 (FIG. 6A) using acetyl chloride and aluminum chloride did produce the desired 3-acetyl indole nucleoside 4.40 (FIG. 6A), although the yield was poor. This intermediate was then deprotected in a 2-step procedure, first with 90% trifluoroacetic acid then with methanolic sodium methoxide to produce the desired 2,5,6-trichloro-3-acetyl-1-(β-D-ribofuranosyl)indole (4.46, FIG. 6A).

Figure 6:
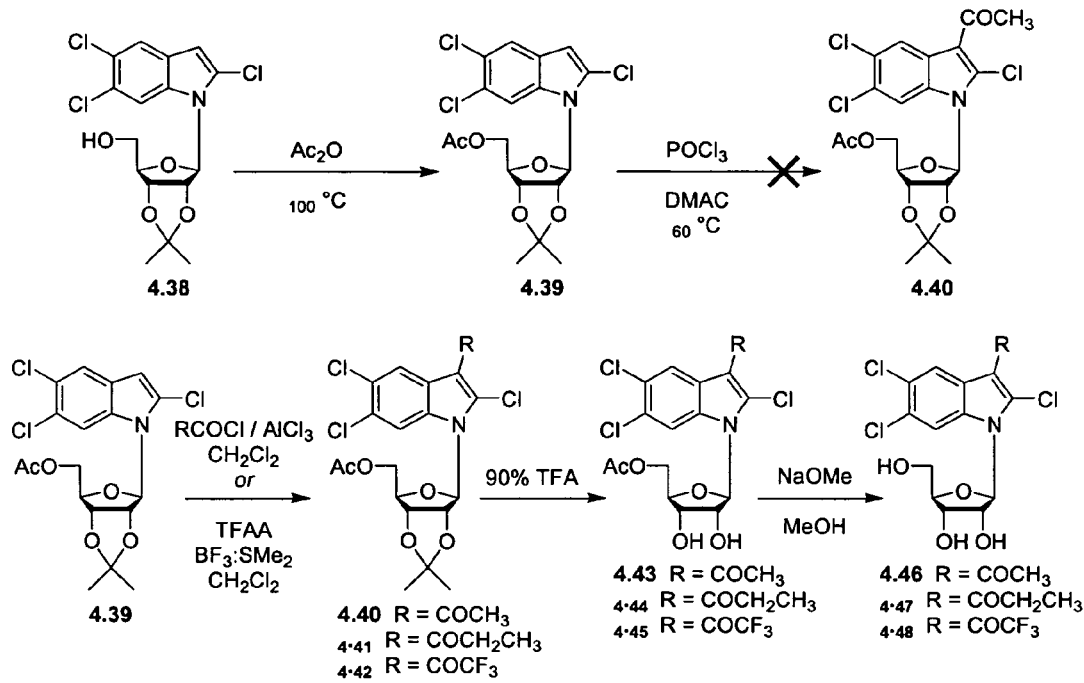
FIG. 6A shows synthesis of 3-modified indole nucleosides: 3-acyl indoles.
FIG. 6B shows synthesis of 3-modified indole nucleoside precursors: 2,5,6-trichloro-3-methylindole.
Figure 6:
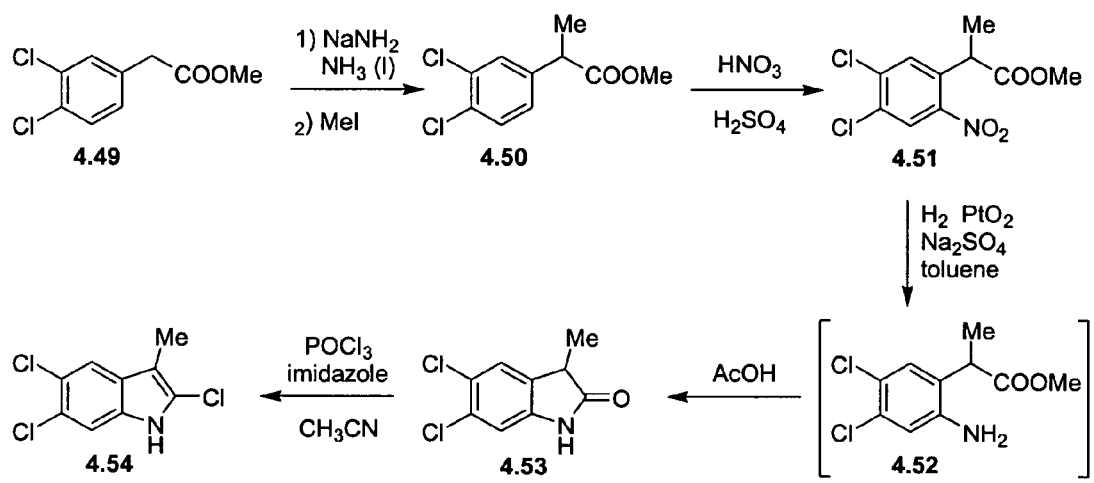

The same procedure was used for the synthesis of the 3-propionyl derivative 4.47 (FIG. 6A). 2,5,6-Trichloro-1-(5-O-acetyl-β-D-ribofuranosyl)indole (4.39, FIG. 6A) was acylated under Friedel-Crafts conditions with propionyl chloride and deprotected in two steps to yield the desired 2,5,6-trichloro-3-propionyl-1-(β-D-ribofuranosyl)indole (4.47, FIG. 6A).

The 3-trifluoroacetyl derivative 4.48 (FIG. 6A) is also desirable. A procedure utilizing $BF_3$:$SMe_2$ and trifluoroacetic anhydride (Kiselyov, et al., Tetrahedron Lett. 1995, 36, 4005-4008, herein incorporated by reference) provided the requisite intermediate 4.42 (FIG. 6A). Deprotection of the intermediate using aqueous trifluoroacetic acid followed by sodium methoxide in methanol produced the desired product 4.48 (FIG. 6A).

To synthesize the desired heterocycle for the 3-methyl derivative, the known methyl 3,4-dichlorophenylacetate (Deutsch et al., Med. Chem. Res. 1999, 9, 213-222, herein incorporated by reference) (4.49, FIG. 6B) was first methylated by a modification of the procedure of Cocker and Grayson (Cocker et al., J. Chem. Soc. Perkin I 1975, 1347-1352, herein incorporated by reference). Thus, 4.49 was deprotonated with sodium amide in liquid ammonia at −78 degrees C and treated with methyl iodide to provide methyl 2-(3,4-dichlorophenyl)propionate (4.50, FIG. 6B). Optimization of the amounts of sodium amide and methyl iodide led to a procedure which produced the desired compound in good yield with essentially none of the dimethylated analog. Nitration of the phenyl ring with $HNO_3$/$H_2SO_4$, followed by a reduction of the nitro group to provide the intermediate methyl 2-(6-amino-3,4-dichlorophenyl)acetate (4.52, FIG. 6B). This intermediate was cyclized in acetic acid to the oxindole 4.53 (FIG. 6B). Compound 4.53 was then chlorinated with phosphorous oxychloride and imidazole (procedure according to Chen; see Chen et al.) to afford the desired 2,5,6-trichloro-3-methylindole (4.54, FIG. 6B).

With the desired indole derivative in hand, attention was turned to the glycosylation of this heterocycle. Attempts to synthesized the glycosylated intermediate 4.56 (FIG. 7) in the same manner as the 3-unsubstituted analog (Chen et al.) using the protected ribofuranosyl chloride 4.55 (Rosemeyer, et al., Helv. Chim. Acta 1988, 71, 1573-1585; and Wilcox, et al., Tetrahedron Lett. 1986, 27, 1011-1014, both of which are herein incorporated by reference) (FIG. 7) provided only small amounts of the desired material. This was a puzzling result, because the addition of the methyl group at the 3-position should have very little effect on the electron distribution in the indole. One would in fact expect the yield to be better because the competing reaction of glycosylation at the 3-position has been eliminated. This prompted the development of an alternative procedure for the synthesis of the desired riboside.

Figure 7:
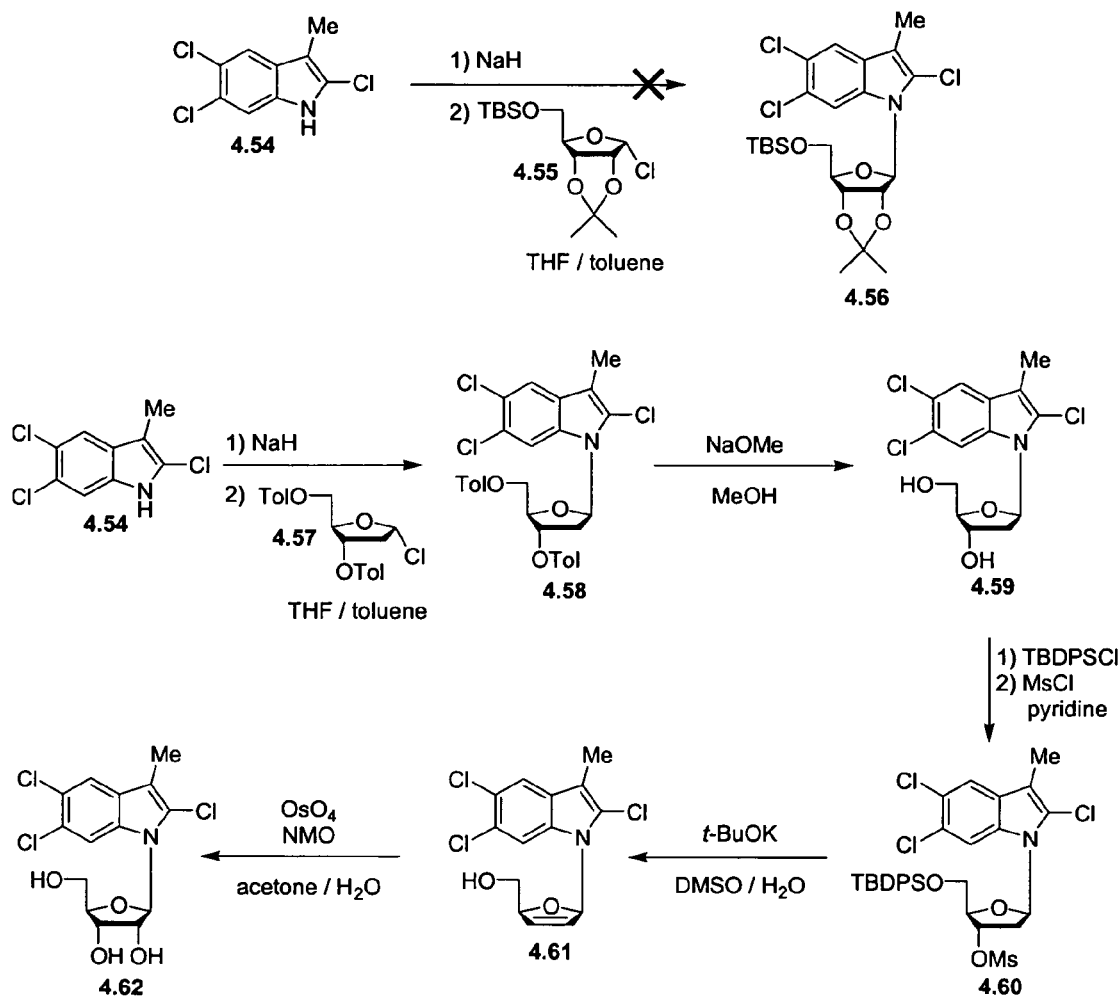
FIG. 7 shows synthesis of 3-modified indole nucleosides: glycosylation of 2,5,6-tricholoro-3-methylindole.

Condensation of 2,5,6-trichloro-3-methylindole (4.54, FIG. 7) with the protected 2-deoxyribofuranosyl chloride 4.57 (See, Rolland, et al., Synth. Commun. 1997, 27, 3505-3511; herein incorporated by reference) (FIG. 7) led to the protected 2'-deoxyribofuranosyl indole nucleoside 4.58 (FIG. 7) in good yield. This nucleoside analog was deprotected with sodium methoxide in methanol, then the 5'-hydroxy group was protected as the bulky and robust t-butyldiphenylsilyl (TBDPS) ether. The 3'-hydroxy group is too sterically hindered to be easily silylated, and was subsequently mesylated with methanesulfonyl chloride. The resulting protected and mesylated nucleoside analog (4.60, FIG. 7) was treated with potassium t-butoxide in wet DMSO (Cao, et al. Helv. Chim. Acta 1992, 75, 1267-1273, herein incorporated by reference) to yield the 2',3'-dideoxy-2',3'-didehydro nucleoside analog 4.61 (FIG. 7). This was dihydroxylated with a catalytic amount of osmium tetroxide and N-methyl-morpholine-N-oxide in acetone/water to yield the desired nucleoside analog 2,5,6-trichloro-3-methyl-1-(β-D-ribofuranosyl)indole (4.62, FIG. 7).

Figure 8:
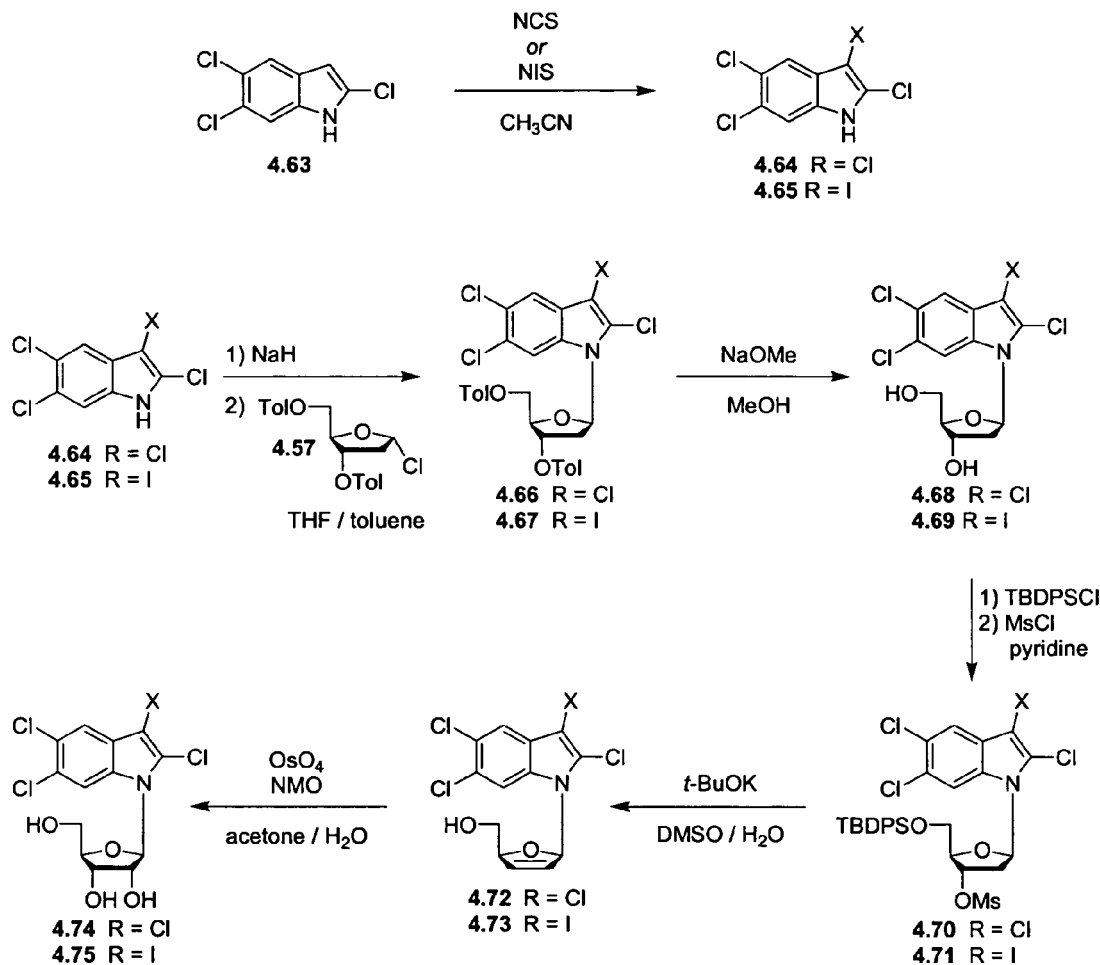
FIG. 8 shows synthesis of 3-modified indole nucleosides: glycosylation of 2,5,6-trichloro-3-haloindoles.

The 3-chloro- and 3-iodo substituted indole nucleosides (4.74 and 4.75, FIG. 8) also were synthesized. It was required, as was the case for the 3-methyl derivative 4.62 (FIG. 7), that the desired heterocycles be synthesized first with the glycosylation and sugar manipulations being carried out later in the synthesis. Thus, 2,5,6-trichloroindole (4.63, FIG. 8) was either chlorinated with N-chlorosuccinimide or iodinated with N-iodosuccinimide to provide the 2,3,5,6-tetrahaloindoles 4.64 and 4.65 (FIG. 8) in good yield. These were then subjected to the same procedure as the methyl analog above. Both were glycosylated as the sodium salt with the α-chlorosugar 3,5-di-O-p-toluoyl-2-deoxy-β-D-ribofuranosyl chloride (4.57, FIG. 8). After deprotection with sodium methoxide in methanol, the compounds were silylated at the 5'-position and mesylated at the 2'-position. Base-induced elimination of the mesylate followed by dihydroxylation of the intermediate 2',3'-dideoxy-2',3'-didehydro nucleosides 4.72 and 4.73 (FIG. 8) provided the desired nucleoside analogs 2,3,5,6-tetrachloro-1-β-D-ribofuranosyl)indole (4.74, FIG. 8) and 2,5,6-trichloro-3iodo-1-β-D-ribofuranosyl)indole (4.75, FIG. 8).

Figure 9:
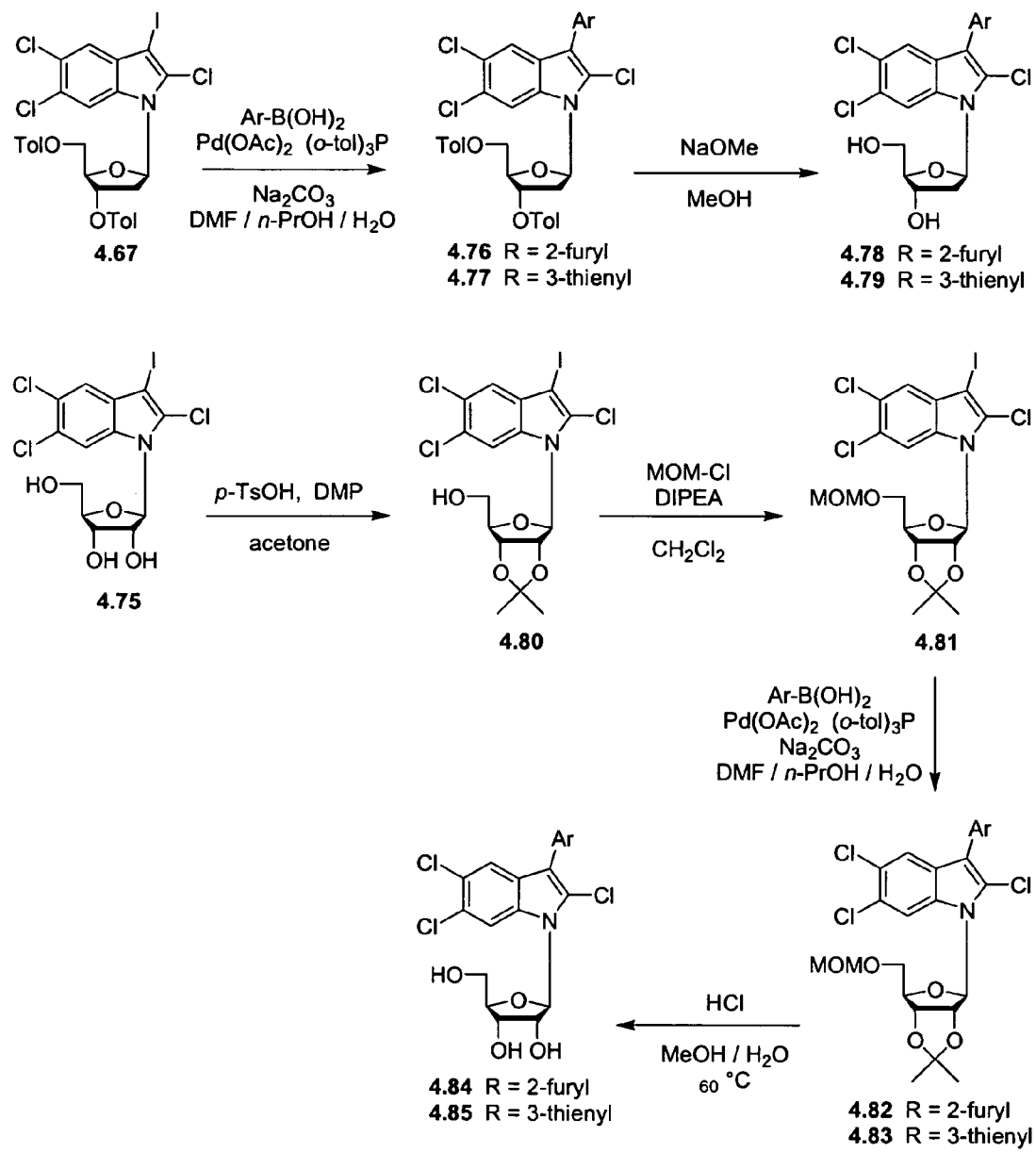
FIG. 9 shows synthesis of 3-modified indole nucleosides: Pd-catalyzed coupling of 3-iodo derivative.

Conditions for the coupling reaction to synthesize the iodo analog were established using the precursor 2,5,6-trichloro-3-iodo-1-(3,5-di-O-p-toluoyl-2-deoxy-β-D-ribofuranosyl) indole (4.67, FIG. 9) using a procedure modified from Huff, et. al. (Synthesis of Unsymmetrical Biaryls Using a Modified Suzuki Cross-Coupling: 4-Biphenylcarboxaldehyde. In Organic Syntheses, Vol. 75; Smith, A. B., III Ed.; American Chemical Society: Washington, DC, 1997; pp 53-60; herein incorporated by reference). The iodinated indole nucleoside was reacted with the desired arylboronic acid in the presence of palladium acetate, a phosphine ligand and base to provide good yields of the desired products 4.76 and 4.77 (FIG. 9). These were deprotected under the standard conditions of methanolic sodium methoxide to produce the 3-aryl-2'-deoxyribofuranosyl indole nucleosides 4.78 and 4.79 (FIG. 9).

With the appropriate conditions established, the corresponding ribofuranosyl derivatives were also synthesized. The 3-iodo indole derivative 4.75 (FIG. 9) was protected as the 5'-O-MOM-2',3'-O-isopropylidene derivative in two steps to avoid the potential complication of boronic ester formation. The protected intermediate 4.81 (FIG. 9) was coupled with 2-furanboronic acid and 3-thiopheneboronic acid in a manner identical to that above, and then deprotected with wet methanolic HCl to provide the desired 3-aryl nucleoside derivatives 4.84 and 4.85 (FIG. 9).

Figure 10:
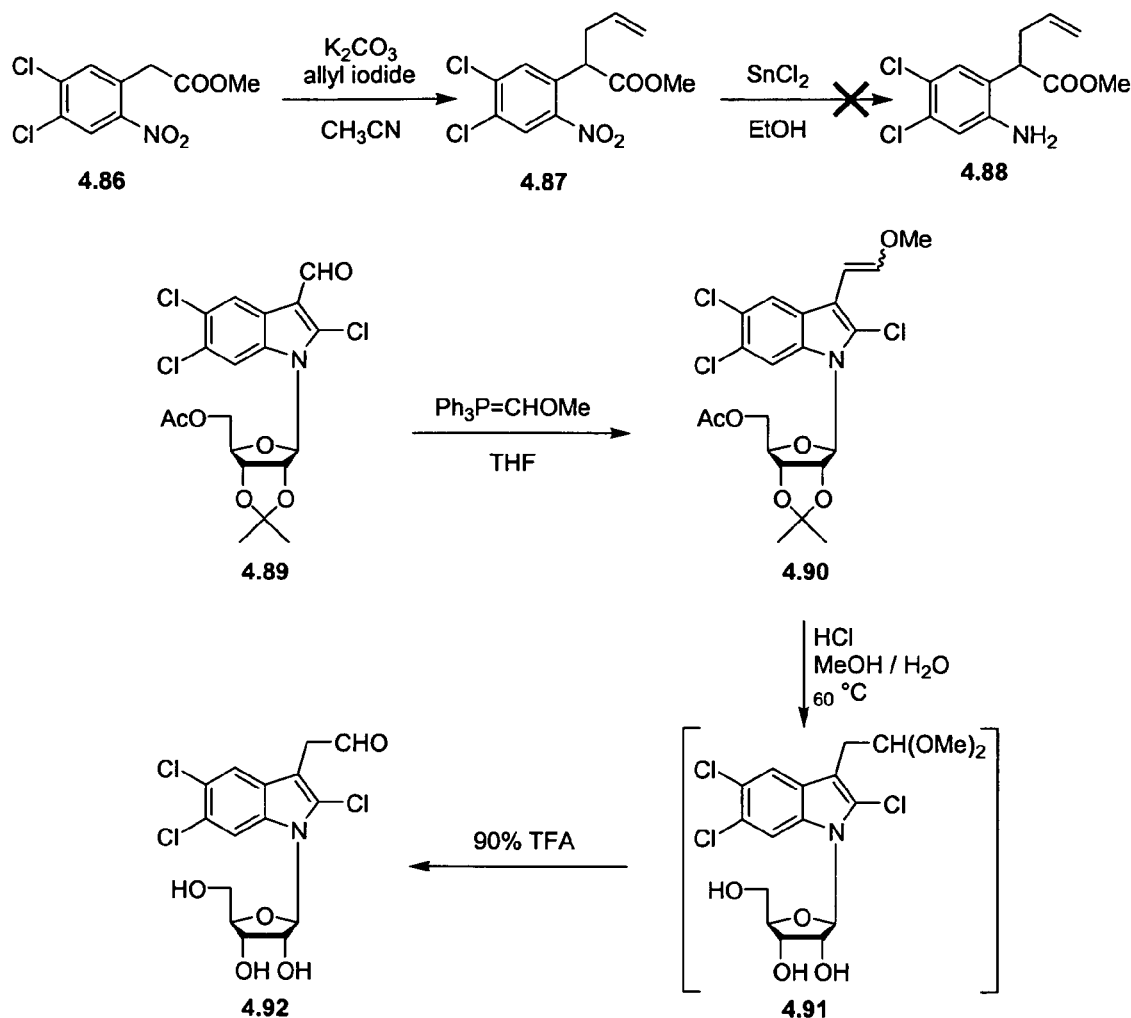
FIG. 10 shows synthesis of 3-modified indole nucleosides: 3-homoaldehyde.

Another desirable synthetic target is the 3-homoaldehyde 4.92 (FIG. 10). A procedure was developed, beginning from the known 3-formyl derivative 4.89 (FIG. 10). The aldehyde was treated with the Wittig reagent derived from (methoxymethyl) triphenylphosphonium chloride to produce vinyl ether 4.90 (FIG. 10). It was expected that treatment of this compound with wet methanolic HCl would unmask the aldehyde and remove the acetonide protecting group, but two additional side-reactions also occurred. Transacetylation of the 5'-O-acetate fully deprotected the sugar moiety, and the liberated aldehyde was immediately protected as the dimethyl acetal. The intermediate thus obtained was then treated with 90% aqueous trifluoroacetic acid to provide the desired 3-homoaldehyde 4.92 (FIG. 10).

Sugar-Modified Indole Nucleosides

Figure 4:
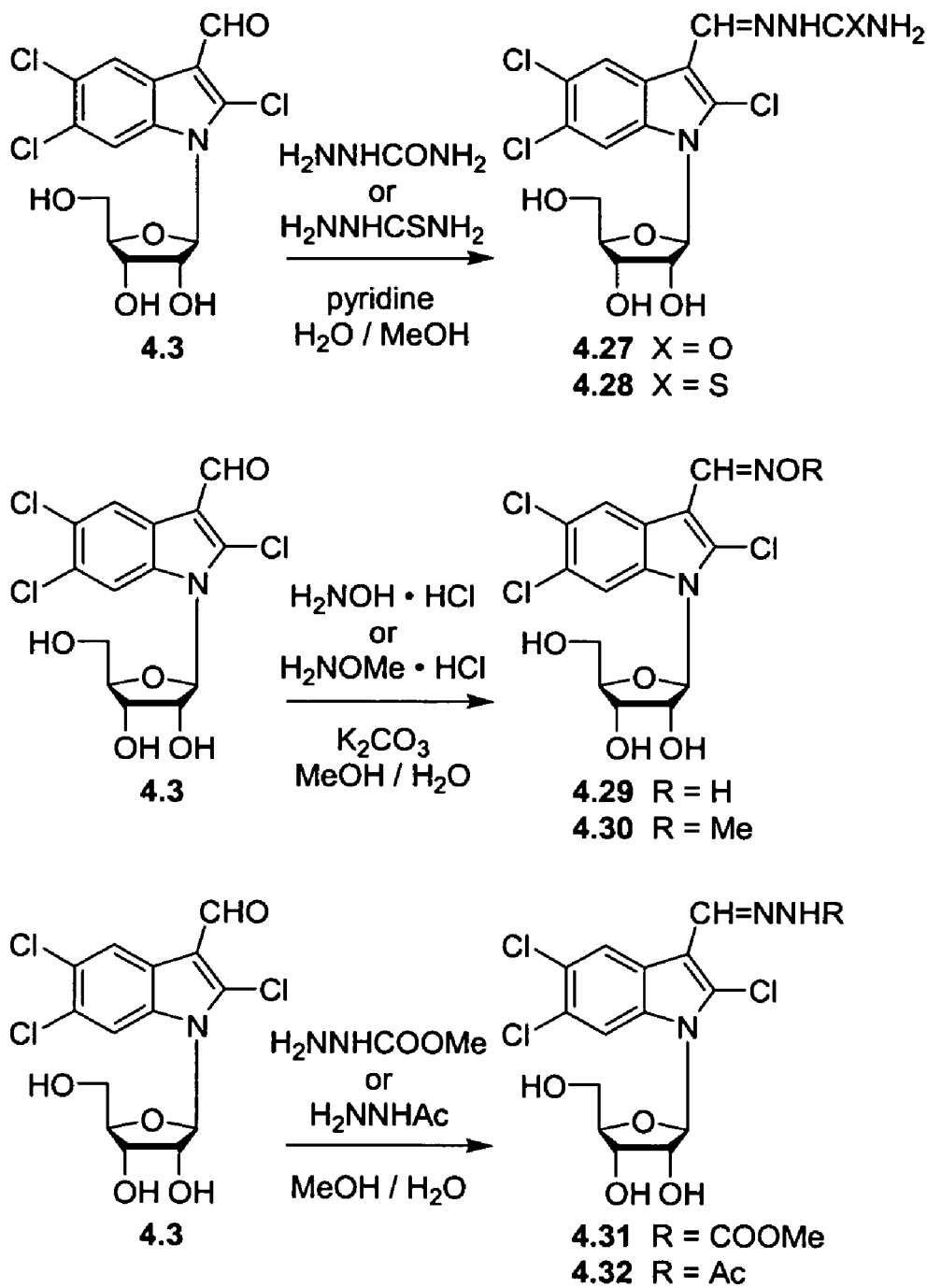
FIG. 4 shows synthesis of 3-modified indole nucleosides: condensation of 3-aldehyde.
Figure 11:
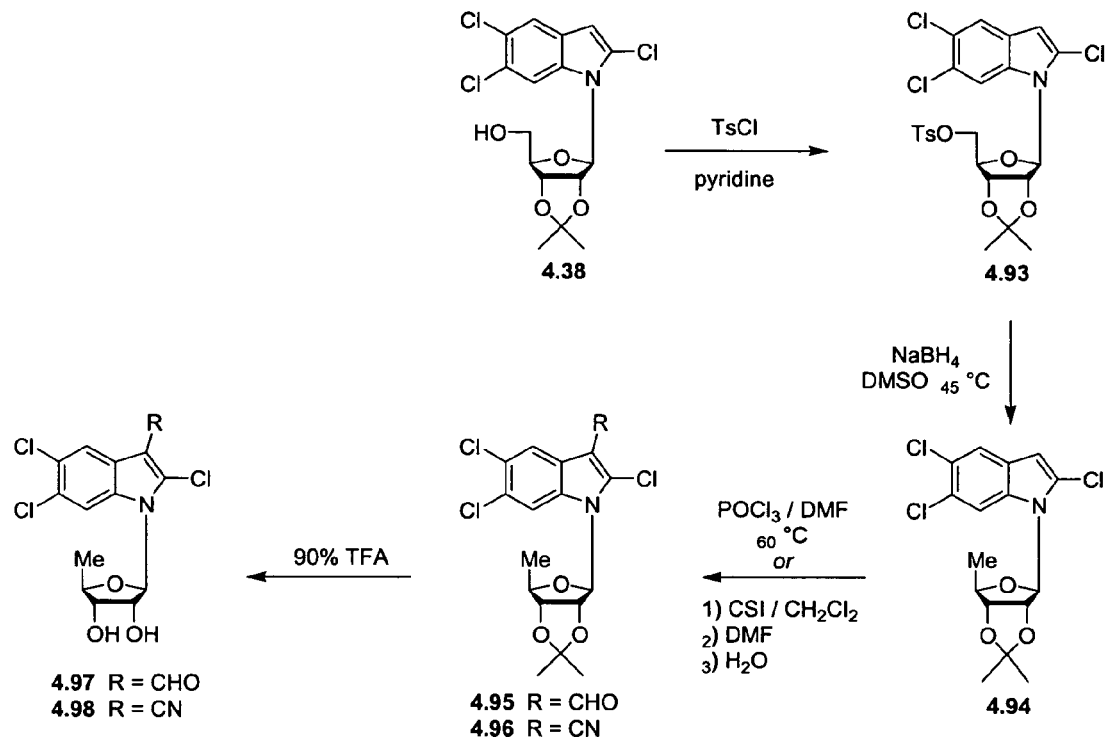
FIG. 11 shows synthesis of sugar-modified indole nucleosides: 5'-deoxyribofuranoside.

Many modifications of the sugar (glycosyl) portion of the indole nucleosides are possible, and a number of them are exemplefied herein. In order to synthesize 5'-deoxy analogs, an appropriate modified nucleoside had to be constructed. Thus the 5'-O-tosylate 4.93 (FIG. 11) was first synthesized, and this compound was reduced with sodium borohydride in DMSO (Hutchins, et al., Tetrahedron Lett. 1969, 40, 3495-3498, herein incorporated by reference) to yield the desired intermediate 4.94 (FIG. 4.11). The synthesis could then diverge into the two desired 3-substituted nucleoside analogs. Treatment of the deoxygenated intermediate 4.94 in the usual manner with either phosphorous oxychloride in DMF or with chlorosulfonyl isocyanate followed by DMF and water produced the protected intermediates 4.95 and 4.96 (FIG. 11), respectively. Deprotection of these compounds was accomplished with 90% aqueous trifluoroacetic acid to provide the desired nucleoside analog 4.97 and 4.98 (FIG. 11).

Figure 12:
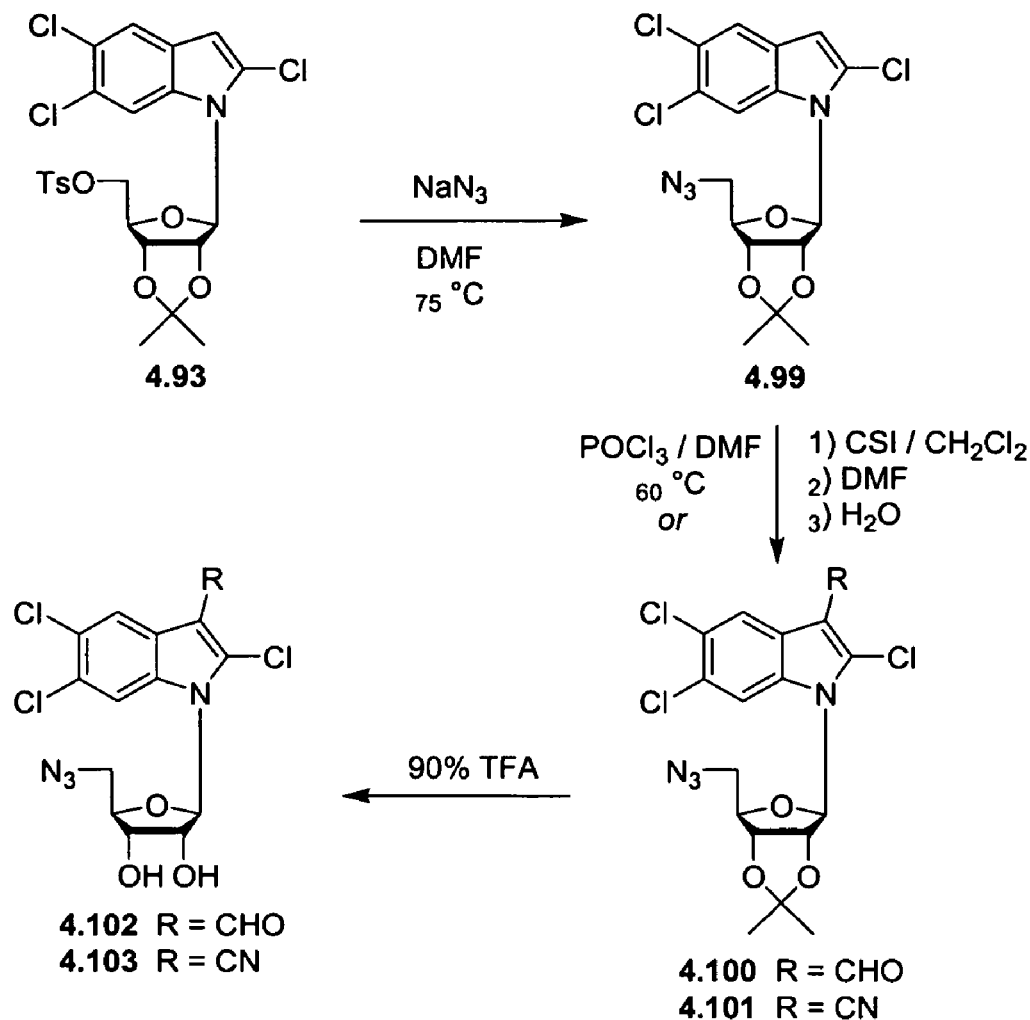
FIG. 12 shows synthesis of sugar-modified indole nucleosides: 5-deoxy-5'-azidoribofuranoside.

In order to synthesize the 5'-deoxy-5'-azido derivatives 4.102 and 4.103 (FIG. 12), the protected 5'-O-tosylate 4.93 (FIG. 12) was used again. Displacement of the tosylate with sodium azide in warm DMF produced the protected 5'-deoxy-5'-azido nucleoside analog 4.99 (FIG. 12). Compound 4.99 was then reacted with either phosphorous oxychloride in DMF or with chlorosulfonyl isocyanate followed by DMF and water and then with 90% aqueous trifluoroacetic acid to yield the desired analogs 2,5,6-trichloro-3-formyl-1-(5-deoxy-5-azido-β-D-ribofuranosyl)indole (4.102, FIG. 12) and 2,5,6-trichloro-3-cyano-1-(5-deoxy-5-azido-β-D-ribofuranosyl)indole (4.103, FIG. 12).

Figure 13:
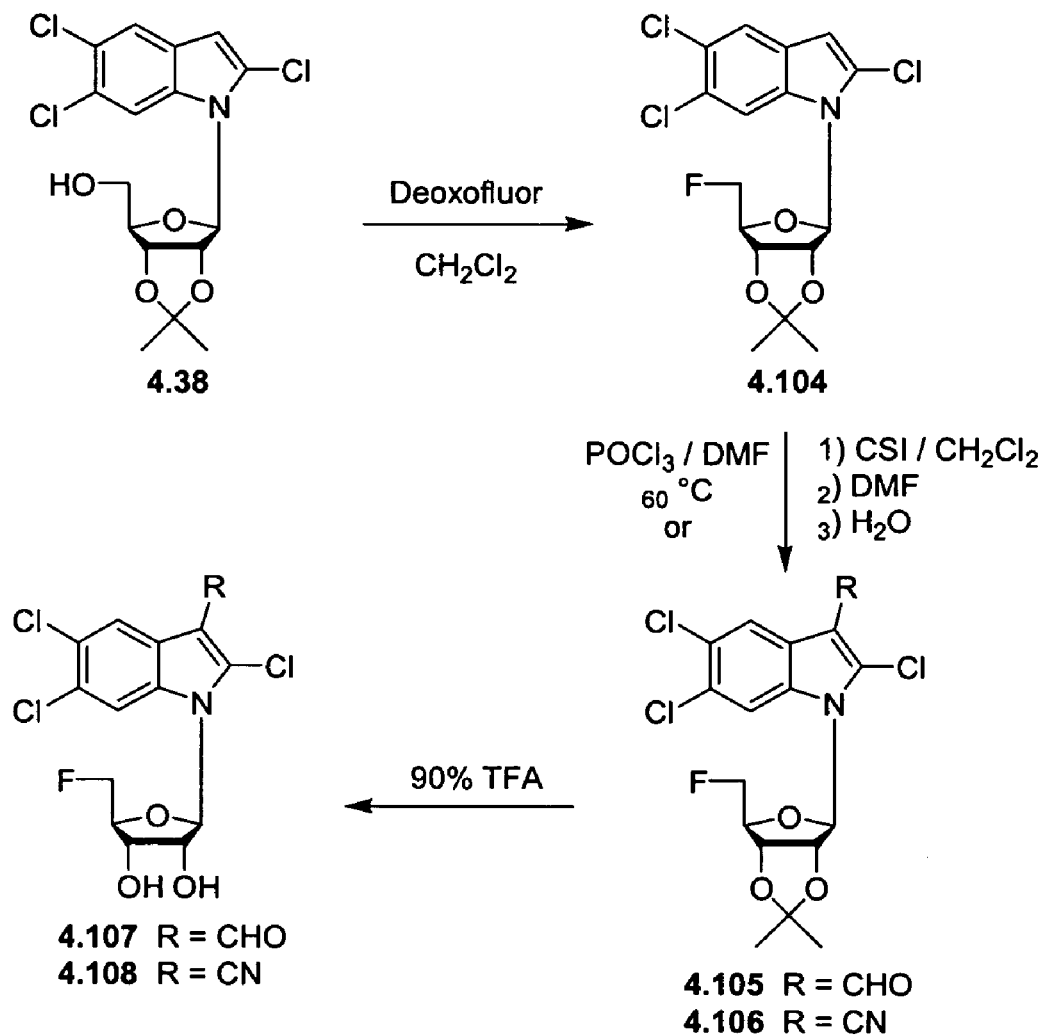
FIG. 13 shows synthesis of sugar-modified indole nucleosides: 5'-deoxy-5' fluororibofuranoside.

A similar strategy was employed for the synthesis of two 5'-deoxy-5'-fluoro analogs. The partially protected intermediate 4.38 (FIG. 13) was treated with Deoxofluor reagent (which was chosen over DAST because of its stability; see Lal et al., J. Org. Chem. 1999, 64, 7048-7054, herein incorporated by reference) to provide the fluorinated intermediate 4.104 (FIG. 13). As in the above synthesis of 5'-deoxy nucleoside analogs, this versatile intermediate was treated with either phosphorous oxychloride in DMF or chlorosulfonyl isocyanate followed by DMF to provide the fluorinated nucleoside analogs 4.107 and 4.108 (FIG. 13) after deprotection of the acetonides 4.105 and 4.106 (FIG. 13) with 90% aqueous trifluoroacetic acid.

Figure 14:
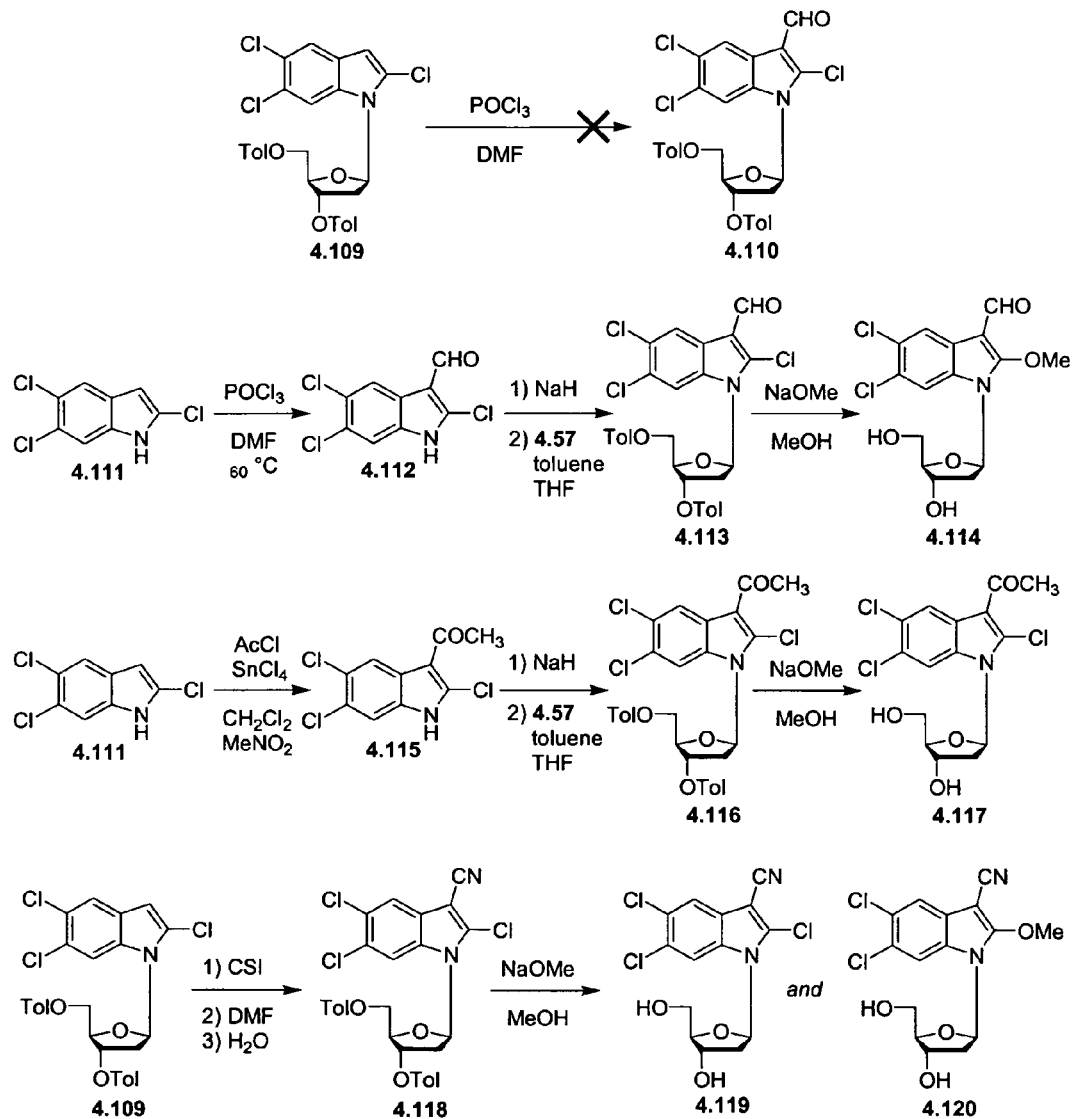
FIG. 14 shows synthesis of sugar-modified indole nucleosides: 2'-deoxyribofuranoside.

A series of 2'-deoxy nucleosides also was synthesized. The desired substituents could be installed on the heterocycle and then glycosylation of the modified heterocycle could then be achieved. 2,5,6-Trichloroindole (Chen et al.) (4.111, FIG. 14) was treated with either phosphorous oxychloride in DMF or acetyl chloride and tin tetrachloride in dichloromethane and nitromethane (Ottoni, et al., Organic Letters 2001, 3, 1005-1007, herein incorporated by reference) to yield 2,5,6-trichloro-3-formylindole (4.112, FIG. 14) and 2,5,6-trichloro-3-acetylindole (4.115, FIG. 14), respectively. These compounds (4.112 and 4.115, FIG. 14) were then glycosylated with the protected 2-deoxyribofuranosyl chloride 4.57 (FIG. 7) to provide the desired protected nucleoside analogs 4.113 and 4.116 (FIG. 7) in good yield. However, during the deprotection two very different behaviors were observed. While the desired 3-acetyl derivative 4.117 (FIG. 14) was produced as expected, the corresponding 3-formyl derivative could not be obtained using any of a variety of different deprotection procedures. The only isolated product from the deprotection of 4.113 (FIG. 14) was the 2-methoxy derivative 4.114 (FIG. 14). Deprotection of the 3-cyano derivative produced an intermediate result, with both the desired 2-chloro (4.119, FIG. 14) and the undesired 2-methoxy (4.120, FIG. 14) derivatives being produced.

Figure 15:
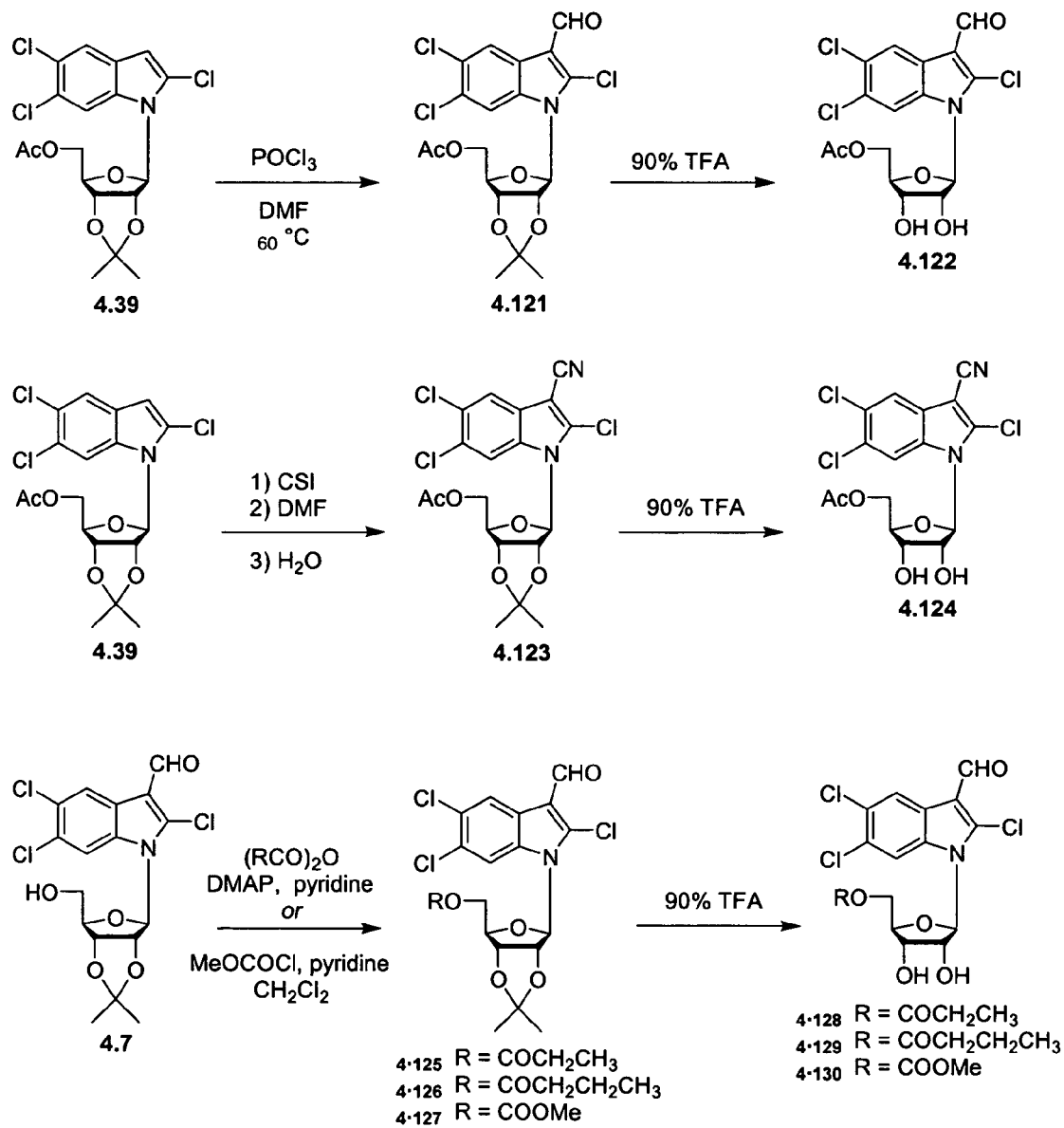
FIG. 15 shows synthesis of sugar-modified indole nucleosides: 5'O-acyl-ribofuranosides.

The 5'-O-acetyl protected derivative 2,5,6-trichloro-3-acetyl-1-(5-O-acetyl-β-D-ribofuranosyl)indole (4.43, FIG. 6A) was synthesized previously (FIG. 6A) and was found to have antiviral activity comparable to the fully deprotected analog 2,5,6-trichloro-3-acetyl-1-(β-D-ribofuranosyl)indole (4.46, FIG. 6A). To determine whether the 5'-O-acetyl analogs of the 3-carboxaldehyde 4.3 and 3-nitrile 4.4 (FIG. 1A) would demonstrate similar behavior, synthesis of these two compounds was initiated (4.122 and 4.124, FIG. 15). Thus, the fully protected 3-unsubstituted indole nucleoside derivative 4.39 (FIG. 15) was treated with either phosphorous oxychloride in DMF or chlorosulfonyl isocyanate followed by DMF to produce the desired protected nucleoside analogs 4.121 and 4.123 (FIG. 15), respectively. The isopropylidene protecting groups were then removed with 90% aqueous trifluoroacetic acid to produce the desired 5'-O-acetyl protected analogs 4.122 and 4.124 (FIG. 15). Additional analogs were synthesized from the partially protected 3-formyl intermediate 4.7 (FIG. 15), instead of partially protected 3-unsubstituted analog 4.38 (FIG. 6A), in an effort to minimize the number of synthetic procedures required for completion of the series. The asymmetric carbonate 4.130 (FIG. 15) was also desired to determine whether the differences in reactivity between acyl and carbonate substituents would have a similar effect on the antiviral profile of the compounds. The protected 5'-O-substituted nucleosides 4.125-4.127 (FIG. 15) were therefore synthesized using either an appropriate anhydride or methyl chloroformate. The acetonide protecting group was removed under the usual conditions to provide the 5'-O-acyl derivatives 4.128 and 4.129 (FIG. 15) and the methyl carbonate 4.130 (FIG. 15).

Brominated Indole Nucleosides

A small number of 2-bromo analogs have been exemplified to illustrate that these compounds also have useful antiviral activity at non-cytotoxic doses. Analogs of the parent compound 4.3 (FIG. 1A) and the 5'-O-acetyl ester derivative 4.122 (FIG. 15), as well as the carboxamide oxime 4.33 (FIG. 5) and the 3-acetyl-2'-deoxy analog 4.117 (FIG. 14) were synthesized.

Figure 16:
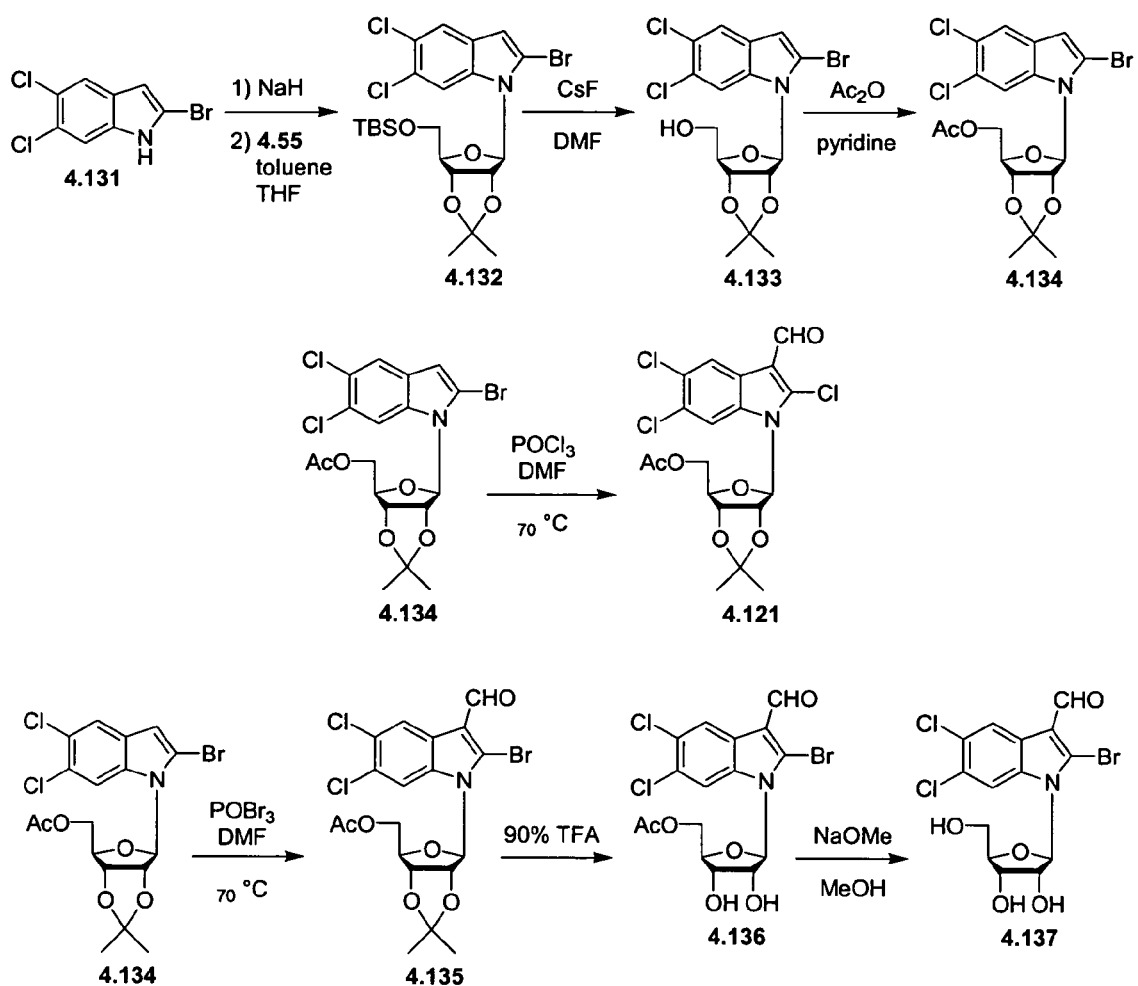
FIG. 16 shows synthesis of 3-formly-2-bromoindole nucleosides.

The ribofuranosyl analogs were synthesized by procedures paralleling those used to synthesize the 2-chloro analogs. 2-Bromo-5,6-dichloroindole (Chen Thesis) (4.131, FIG. 16) was glycosylated with chlorosugar 4.55 (FIG. 7). The resulting ribofuranoside was deprotected with cesium fluoride and then re-protected as the acetate ester to provide the common intermediate 4.134 (FIG. 16). In order to synthesize the 3-formyl derivatives, phosphorous oxybromide and DMF produced the desired 2-bromo analog 4.135 (FIG. 16). The synthesis was completed as before by treatment of 4.135 (FIG. 16) with 90% aqueous trifluoroacetic acid followed by methanolic sodium methoxide to provide 4.136 and 4.137 (FIG. 16) in good yield.

Figure 17:
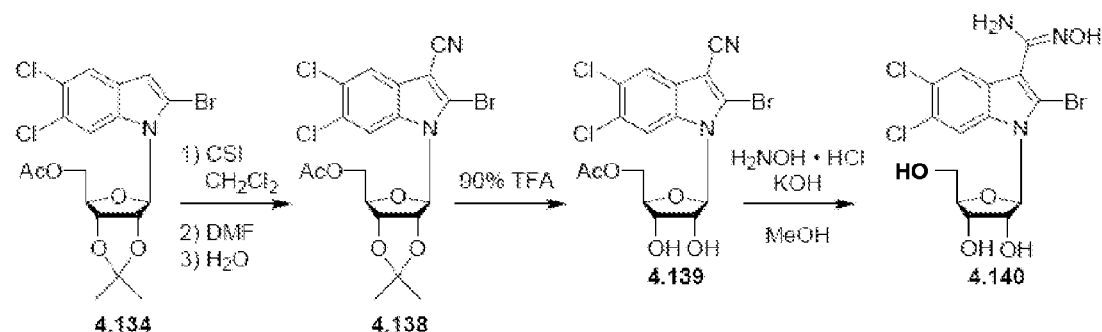
FIG. 17 shows synthesis of 2-bromoindole carboxamide oxime nucleoside.

The carboxamide oxime 4.140 (FIG. 17) was also synthesized from the intermediate 4.134 (FIG. 17). Compound 4.134 was cyanated using chlorosulfonyl isocyanate followed by DMF and water to provide the 3-cyanoindole nucleoside 4.138 (FIG. 17). Deprotection of the acetonide in 90% aqueous trifluoroacetic acid was followed by treatment with methanolic hydroxylamine which deprotected the 5'-O-acetate in situ, and formed the desired carboxamide oxime 4.140 (FIG. 4.17) after a prolonged reaction time.

Figure 18:
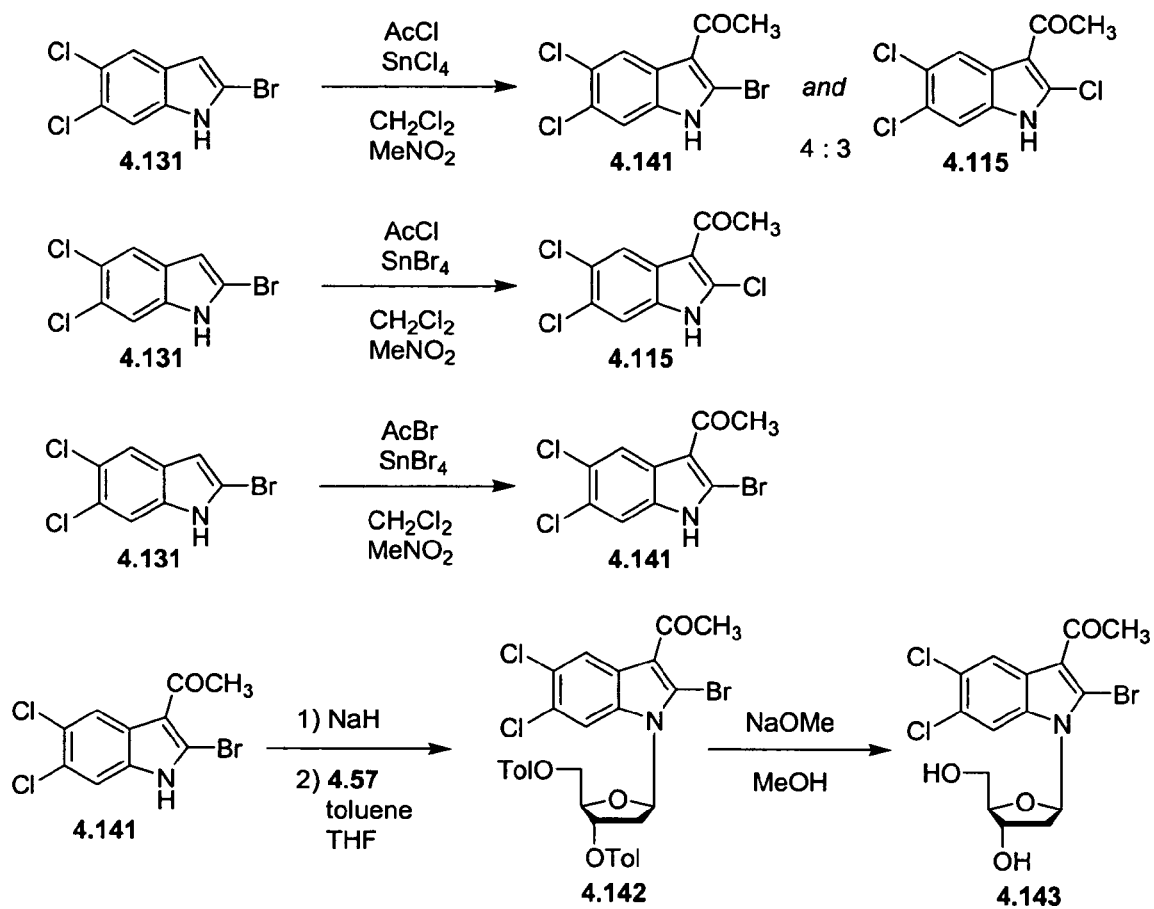
FIG. 18 shows synthesis of 3-acetyl-2-bromo indole 2'-deoxyribofuranoside.

The synthesis of the 2-bromo analog of 3-acetyl-2'-deoxy indole nucleoside 4.117 (FIG. 4.14) again proceeded from the known heterocycle 2-bromo-5,6-dichloroindole (4.131, FIG. 4.22). By removing all sources of exchangeable chloride and using both tin tetrabromide and acetyl bromide, the desired 2-bromo-5,6-dichloro-3-acetylindole (4.141, FIG. 18) was synthesized in moderate yield. With the appropriate heterocycle in hand, the glycosylation reaction was performed as before and the intermediate 4.142 (FIG. 4.18) was deprotected with sodium methoxide in methanol to yield the desired nucleoside analog 4.143 (FIG. 4.18).

EXAMPLE 2

Synthesis and Biological Evaluation of Compounds

This Example describes the biological evaluation of the compounds described above. In particular, the antiviral activity of each of the compounds was tested with nearly all of the compounds having some antiviral activity.

The antiviral activity of one member of each of the chemical series described above is exemplified in the following table. Antiviral activity was demonstrated using human cytomegalovirus (HCMV) and herpes simplex virus type 1 (HSV-1) assayed as described in the Experimental section below. Cytotoxicity was measured in stationary human foreskin fibroblasts (HFF cells) and growing KB cells also as described in the Experimental section below.

| Compound | | 50% Inhibitory Concentration, μM | | | |
|---|---|---|---|---|---|
| Type | Number | HCMV Activity | HSV-1 Activity | HFF Cytotoxicity | KB Cytotoxicity |
| Indole Nuc'side | 4.3 | 0.2 | 40 | 45 | 45 |
| 2-Sub'ted | 4.14 | 17 | >100 | 100 | 90 |
| 3-Sub'ted | 4.34 | 0.4 | 70 | 100 | 90 |
| 5'-Sugar Modified | 4.97 | 0.3 | 20 | 32 | 25 |
| Bromi'ted N'side | 4.136 | 0.3 | 15 | 32 | 40 |

Members of each group exhibited antiviral activity with several members being active against HCMV at concentrations at least 100-fold lower than those which produced cytotoxicity in uninfected cells.

A. Experimental Section

General Chemical Procedures. All solvents were dried prior to use according to known procedures; all reagents were obtained from commercial sources or were synthesized from literature procedures, and were used without further purification unless otherwise noted. Air-sensitive reactions were performed under slight positive pressure of argon, unless otherwise noted. Room temperature is assumed to be between 20-25 C. Evaporation of solvents was accomplished under reduced pressure (water aspirator, 12 mmHg), at less than 40 C, unless otherwise noted. Chromatography solvent systems are expressed in v:v ratios or as % v. Melting points were taken on a Mel-Temp apparatus, and are uncorrected. Thin layer chromatography was performed on silica gel GHLF plates from Analtech (Newark, Del.). Chromatograms were visualized under UV light at 254 nm unless otherwise noted. $^1$H-NMR spectra were obtained at 300 MHZ on a Bruker DPX300 spectrometer or at 500 MHz on a Bruker DRX500 spectrometer. $^{13}$C-NMR spectra were obtained at 75 MHz on a Bruker DPX300 spectrometer or at 125 MHz on a Bruker DRX500 spectrometer. $^{19}$F-NMR spectra were obtained at 300 MHz on a Bruker DPX300 spectrometer. Chemical shift values for $^1$H determined relative to an internal tetramethylsilane standard (0.00 ppm); chemical shift values for $^{13}$C were determined relative to the solvent used (39.52 ppm for DMSO-d$_6$ and 77.23 ppm for CDCl$_3$); chemical shift values for $^{19}$F were determined relative to an external TFA standard (−76.50 ppm). Mass Spectrometry was performed at the University of Michigan Department of Chemistry Mass Spectrometry facility. Elemental Analysis was performed at the University of Michigan Chemistry Department Elemental Analysis facility.

5,6-Dichloro-2-dimethylamino-3-formyl-1-(2,3-O-isopropylidene-β-D-ribofuranosyl)indole (4.8)

To a solution of 2,5,6-trichloro-3-formyl-1-(2,3-O-isopropylidene-β-D-ribofuranosyl)-indole (4.7, 100 mg, 0.24 mmol) dissolved in DMF (1 mL) was added 40% aqueous dimethylamine (1 mL). The resulting mixture was stirred at room temperature for 16 h, then the solvent was evaporated (0.5 mmHg, 40 C) to provide a pale yellow crystalline solid. The residue was suspended in water (10 mL) and brine (40 mL) and the aqueous suspension was extracted with EtOAc (2×25 mL). The combined organic extracts were washed with brine (10 mL), dried over MgSO$_4$, filtered and evaporated to yield a pale yellow crystalline solid. The solid was dissolved in CHCl$_3$ (1 mL) and subjected to column chromatography (40×350 mm) on silica gel with 1:2 hexane:EtOAc. Fractions containing product were pooled and evaporated to yield 81 mg (79%) of 4.8 as a white crystalline solid: R$_f$ 0.5 (1:2 hexane:EtOc); mp 206-207 C; $^1$H NMR (500 MHz, DMSO-d$_6$) δ 10.24 (s, 1H), 8.29 (s, 1H), 7.99 (s, 1H), 5.89 (d, 1H), 5.40 (t, 1H, D$_2$O exch.), 5.16 (m, 1H), 5.07 (m, 1H), 4.12 (m, 1H), 3.74 (s, 2H), 3.20 (s, 6H), 1.60 (s, 3H), 1.35 (s, 3H); $^{13}$CNMR (125 MHz, DMSO-d$_6$) δ 184.25, 158.96, 131.36, 126.13, 125.38, 124.85, 120.96, 114.99, 114.80, 106.38, 89.90, 83.62, 81.11, 79.53, 60.38, 45.02, 27.19, 25.35.

5,6-Dichloro-2-(N-pyrrolidino)-3-formyl-1-(2,3-O-isopropylidene-β-D-ribofuranosyl)indole (4.9)

To a solution of 2,5,6-trichloro-3-formyl-1-(2,3-O-isopropylidene-β-D-ribofuranosyl)-indole (4.7, 100 mg, 0.24 mmol) dissolved in DMF (1 mL) was added pyrrolidine (1 mL). The resulting mixture was stirred at room temperature for 16 h, then the solvent was evaporated to provide a pale yellow oil. The residue was suspended in water (10 mL) and brine (40 mL) and extracted with EtOAc (2×25 mL). The combined organic extracts were washed with brine (10 mL), dried over MgSO$_4$, filtered and evaporated to yield a pale yellow oil which solidified upon standing. The solid was dissolved in CHCl$_3$ (1 mL) and subjected to column chromatography (40×350 mm) on silica gel with 1:2 hexane:EtOAc. Fractions containing product were pooled and evaporated to yield 75 mg (69%) of 4.9 as a white crystalline solid: R$_f$ 0.5 (1:2 hexane:EtOAc); mp 119-120 C; $^1$H NMR (500 MHz, DMSO-d$_6$) δ 10.04 (s, 1H), 8.30 (s, 1H), 7.86 (s, 1H), 5.88 (d, 1H), 5.33 (t, 1H, D$_2$O exch.), 4.99 (m, 2H), 4.05 (s, 1H), 3.62 (m, 6H), 1.99 (q, 4H), 1.51 (s, 3H), 1.28 (s, 3H); $^{13}$C NMR (125 MHz, DMSO-d$_6$) δ 183.29, 155.95, 131.88, 127.63, 125.21, 123.96, 120.48, 114.79, 114.69, 104.82, 90.66, 83.53, 80.98, 79.43, 60.28, 54.26, 27.19, 25.49, 25.33.

5,6-Dichloro-2-dimethylamino-3-formyl-1-(β-D-ribofuranosyl)indole (4.6)

5,6-Dichloro-2-dimethylamino-3-formyl-1-(2,3-O-isopropylidene-β-D-ribofuranosyl)indole (4.8, 74 mg, 0.17 mmol) was dissolved in 90% aqueous TFA (5 mL), and the resulting solution was stirred at room temperature for 2 min. The excess solvent was removed under vacuum, and the residual oil suspended in 5% aqueous $Na_2CO_3$ (20 mL) The aqueous suspension was extracted with EtOAc (2×25 mL) and the combined organic extracts were washed with brine(25 mL), dried over $MgSO_4$, filtered and evaporated to yield a white solid. The crude material was dissolved in MeOH (1 mL) and subjected to column chromatography (40×350 mm) on C18-reverse phase silica gel with 75% MeOH/water. Fractions containing product were pooled and evaporated to yield 57 mg (85%) of 4.6 as a white powder: mp 181-182 C; $R_f$ 0.3 (10% MeOH/CHCl$_3$); $^1$H-NMR (500 MHz, DMSO-d$_6$): δ 10.18 (s, 1H), 8.27 (s, 1H), 8.24 (s, 1H), 5.72 (d, 1H), 5.34 (m, 2H, $D_2O$ exch.), 5.21 (d, 1H, $D_2O$ exch.), 4.50 (q, 1H), 4.12 (t, 1H), 3.92 (d, 1H), 3.68 (s, 2H), 3.17 (s, 6H), $^{13}$C-NMR (125 MHz, DMSO-d$_6$): δ 184.09, 159.90, 131.82, 126.27, 125.07, 124.48, 120.80, 115.46, 106.28, 88.41, 85.57, 70.33, 69.77, 61.15, 44.94. HRMS (EI) m/z calcd. for $C_{16}H_{18}Cl_2N_2O_5$ 388.0593, found 388.0596. Anal calcd for $C_{16}H_{18}Cl_2N_2O_5 \cdot ¼H_2O$: C, 48.81; H, 4.74; N, 7.11. Found: C, 48.69; H, 4.83; N, 6.94.

5,6-Dichloro-2-pyrrolidino-3-formyl-1-(β-D-ribofuranosyl)indole (4.10)

5,6-Dichloro-2-pyrrolidino-3-formyl-1-(2,3-O-isopropylidene-β-D-ribofuranosyl)indole (4.9, 65 mg, 0.14 mmol) was dissolved in 90% aqueous TFA (5 mL), and the resulting solution was stirred at room temperature for 2 min. The excess solvent was removed under vacuum, and the residual oil suspended in 5% aqueous $Na_2CO_3$ (20 mL) The aqueous suspension was extracted with EtOAc (2×25 mL) and the combined organic extracts were washed with brine(25 mL), dried over $MgSO_4$, filtered and evaporated to yield a white solid. The crude material was dissolved in MeOH (1 mL) and subjected to column chromatography (40×350 mm) on C18-reverse phase silica gel with 75% MeOH/water. Fractions containing product were pooled and evaporated to yield 39 mg (66%) of 4.10 as a white powder: mp 131-134° C.; $R_f$ 0.2 (10% MeOH/CHCl$_3$); $^1$H-NMR (500 MHz, DMSO-d$_6$): δ 10.05 (s, 1H), 8×(s, 1H), 8.17 (s, 1H), 5.71 (d, 1H), 5.34 (m, 1H, $D_2O$ exch.), 5.23 (d, 1H, $D_2O$ exch.), 5.18 (d, 1H, $D_2O$ exch.), 4.43 (q, 1H), 4.09 (m, 1H), 3.91 (m, 1H), 3.68 (d, 4H), 1.99 (m, 4H). $^{13}$C-NMR (125 MHz, DMSO-d$_6$): δ 182.93, 156.97, 132.27, 127.85, 124.81, 123.41, 120.26, 115.04, 104.56, 89.19, 85.32, 69.77, 69.63, 61.00, 54.07, 25.52. HRMS (EI) m/z calcd. for $C_{18}H_{20}Cl_2N_2O_5$ 414.0749, found 414.0733. Anal calcd for $C_{18}H_{20}Cl_2N_2O_5 \cdot ½H_2O$: C, 50.96; H, 4.99; N, 6.60. Found: C, 51.20; N, 6.54.

5,6-Dichloro-2-dimethylamino-3-cyano-1-(β-D-ribofuranosyl)indole (4.14)

5,6-Dichloro-2-dimethylamino-3-cyano-1-(2,3-O-isopropylidene-β-D-ribofuranosyl)indole (4.12, 100 mg, 0.23 mmol) was dissolved in 90% aqueous TFA (5 mL), and the resulting solution was stirred at room temperature for 2 min. The excess solvent was then removed under vacuum, and the residual oil suspended in 5% aqueous $Na_2CO_3$ (20 mL). The aqueous suspension was extracted with EtOAc (2×25 mL), and the combined organic extracts were washed with brine (25 mL), dried over $MgSO_4$, filtered and evaporated to yield a white solid. The crude material was dissolved in MeOH (1 mL) and subjected to column chromatography (40×350 mm) on C18-reverse phase silica gel with 75% MeOH/water. Fractions containing product were pooled and evaporated to yield 77 mg (85%) of 4.14 as a white powder: mp 186-188 C; $R_f$ 0.3 (10% MeOH/CHCl$_3$); $^1$H-NMR (500 MHz, DMSO-d$_6$): δ 8.34 (s, 1H), 7.59 (s, 1H), 5.69 (d, 1H), 5.37 (d, 1H, $D_2O$ exch.), 5.35 (t, 1H, $D_2O$ exch.), 5.20 (d, 1H, $D_2O$ exch.), 4.51 (q, 1H), 4.13 (m, 1H), 3.92 (m, 1H), 3.67 (m, 2H), 3.08 (s, 6H). $^{13}$C-NMR (125 MHz, DMSO-d$_6$): δ 158.43, 130.70, 127.62, 124.96, 124.62, 117.81, 115.95, 115.41, 88.13, 85.60, 72.63, 70.31, 69.73, 61.09, 43.53. HRMS (ES) m/z calcd. For $C_{16}H_{17}Cl_2N_3O_4 \cdot Na \cdot MeOH$ 440.0756, found 440.0756. Anal calcd for $C_{16}H_{17}Cl_2N_3O_4 \cdot ½MeOH$: C, 49.27; H, 4.76; N, 10.45. Found: C, 49.39; H, 4.37; N, 10.28.

5,6-Dichloro-2-pyrrolidino-3-cyano-1-(β-D-ribofuranosyl)indole (4.15)

5,6-Dichloro-2-pyrrolidino-3-cyano-1-(2,3-O-isopropylidene-β-D-ribofuranosyl)indole (4.13, 73 mg, 0.16 mmol) was dissolved in 90% aqueous TFA (5 mL), and the resulting solution was stirred at room temperature for 2 min. The excess solvent was then removed under vacuum, and the residual oil suspended in 5% aqueous $Na_2CO_3$ (20 mL). The aqueous suspension was extracted with EtOAc (2×25 mL), and the combined organic extracts were washed with brine (25 mL), dried over $MgSO_4$, filtered and evaporated to yield a white solid. The crude material was dissolved in MeOH (1 mL) and subjected to column chromatography (40×350 mm) on C18-reverse phase silica gel with 75% MeOH/water. Fractions containing product were pooled and evaporated to yield 53 mg (80%) of 4.15 as a white powder: mp 186-188 C; $R_f$ 0.4 (10% MeOH/CHCl$_3$); $^1$H-NMR (500 MHz, DMSO-d$_6$): δ 8.23 (s, 1H), 7.43 (s, 1H), 5.71 (d, 1H), 5.33 (d, 1H, $D_2O$ exch.), 5.30 (d, 1H, $D_2O$ exch.), 5.18 (d, 1H, $D_2O$ exch.), 4.46 (q, 1H), 4.10 (m, 1H), 3.91 (m, 1H), 3.71-3.62 (m, 6H), 2.01-1.93 (m, 4H). $^{13}$C-NMR (125 MHz, DMSO-d$_6$): δ 155.54, 130.83, 129.01, 124.82, 123.38, 116.72, 116.57, 115.72, 88.60, 85.45, 70.07, 69.59, 68.49, 60.99, 52.27, 25.26. HRMS (ES) m/z calcd. for $C_{18}H_{19}Cl_2N_3O_4Na \cdot MeOH$ 466.0912, found 466.0915. Anal calcd for $C_{18}H_{19}Cl_2N_3O_4$: C, 52.44; H, 4.65; N, 10.19. Found: C, 52.13; H, 4.58; N, 9.71.

5,6-Dichloro-2-methylamino-3-formyl-1-(β-D-ribofuranosyl)indole (4.18)

2,5,6-Trichloro-3-formyl-1-(β-D-ribofuranosyl)indole (4.3, 125 mg, 0.33 mmol) was dissolved in 33% ethylamine solution in ethanol (10 mL), and the resulting solution was stirred at room temperature for 30 min. The solvent was then evaporated to approx 1 mL, and diluted with EtOAc (50 mL). The suspension was washed with $H_2O$ (20 mL) and brine (50 mL), then dried over $MgSO_4$, filtered and evaporated to yield a yellow residue. The residue was dissolved in MeOH (1 mL) and subjected to column chromatography (40×350 mm) on silica gel with 20% MeOH/CHCl$_3$. Fractions containing product were pooled and evaporated to yield a clear viscous residue which was dissolved in MeOH (1 mL) and subjected to column chromatography (40×350 mm) on C18-reverse phase silica gel with 75% MeOH/$H_2O$. Fractions containing product were pooled and evaporated to yield a white solid which was recrystallized from MeOH/$H_2O$ to yield 56 mg (43%) of 4.18 as a white microcrystalline solid: mp 241-242 C; $R_f$ 0.5 (20% MeOH/CHCl$_3$); $^1$H-NMR (500 MHz, DMSO-d$_6$): δ 9.98 (s, 1H), 8.24 (s, 1H), 7.97 (q, 1H, $D_2O$ exch.), 7.69

(s, 1H), 5.93 (t, 1H, $D_2O$ exch.), 5.91 (d, 1H), 5.34 (d, 1H, $D_2O$ exch.), 5.32 (d, 1H, $D_2O$ exch.), 4.34 (q, 1H), 4.09 (t, 1H), 4.05 (s, 1H), 3.76-3.67 (m, 2H), 3.12 (d, 3H). $^{13}$C-NMR (125 MHz, DMSO-$d_6$): δ 181.72, 154.48, 133.66, 127.05, 123.71, 122.72, 119.70, 110.91, 100.20, 88.56, 86.10, 70.78, 70.30, 60.80, 33.45. HRMS (ES) m/z calcd. for $C_{15}H_{16}Cl_2N_2O_5$+H 375.0514, found 375.0511. Anal calcd for $C_{15}H_{16}Cl_2N_2O_5$ ¼$H_2O$: C, 47.45; H, 4.38; N, 7.38. Found: C, 47.53; H, 4.59; N, 7.26.

5,6-Dichloro-2-isopropylamino-3-formyl-1-(β-D-ribofuranosyl)indole (4.19)

2,5,6-Trichloro-3-formyl-1-(β-D-ribofuranosyl)indole (4.3, 171 mg, 0.45 mmol) was dissolved in isopropylamine (10 mL), and the resulting solution was stirred at room temperature for 16 h. The solvent was then evaporated and the residue dissolved in EtOAc (50 mL). The suspension was washed with $H_2O$ (20 mL) and brine (50 mL), then dried over $MgSO_4$, filtered and evaporated to yield a yellow syrup. The residue was dissolved in MeOH (1 mL) and subjected to column chromatography (40×350 mm) on silica gel with 20% MeOH/$CHCl_3$. Fractions containing product were pooled and evaporated to yield a clear viscous residue which was dissolved in MeOH (1 mL) and subjected to column chromatography (40×350 mm) on C18-reverse phase silica gel with 75% MeOH/$H_2O$. Fractions containing product were pooled and evaporated to yield a white solid which was recrystallized from MeOH/$H_2O$ to yield 76 mg (42%) of 4.19 as a white microcrystalline solid: mp 143-145 C; $R_f$ 0.6 (20% MeOH/$CHCl_3$); $^1$H-NMR (500 MHz, DMSO-$d_6$): δ 9.90 (s, 1H), 8.19 (s, 1H), 7.73 (s, 1H), 7.26 (d, 1H, $D_2O$ exch.), 5.87 (d, 1H, $D_2O$ exch.), 5.68 (s, 1H, $D_2O$ exch.), 5.37 (d, 1H, $D_2O$ exch.), 5.29 (d, 1H), 4.35 (q, 1H), 4.10 (s, 1H), 4.07 (m, 1H), 4.00 (s, 1H), 3.70 (m, 2H), 1.28 (s, 6H). $^{13}$C-NMR (125 MHz, DMSO-$d_6$): δ 181.55, 153.38, 133.43, 127.15, 123.96, 122.70, 119.37, 111.47, 99.04, 88.51, 85.88, 70.76, 69.80, 60.69, 48.99, 22.77, 22.55. HRMS (ES) m/z calcd. for $C_{17}H_{20}Cl_2N_2O_5$·Na·$CH_3OH$ 457.0909, found 457.0912. Anal calcd for $C_{17}H_{20}Cl_2N_2O_5$·¼$H_2O$: C, 49.53; H, 5.13; N, 6.80. Found: C, 49.83; H, 5.04; N, 6.51.

5,6-Dichloro-2-methoxy-3-formyl-1-(β-D-ribofuranosyl)indole (4.25)

2,5,6-Trichloro-3-formyl-1-(5-O-acetyl-β-D-ribofuranosyl)indole (see Chen et al.; 4.24, 148 mg, 0.35 mmol) was dissolved in dry MeOH (20 mL) to which was added sodium methoxide (21 mg, 0.39 mmol). The solution was stirred at room temperature for 30 min, then the solvent was removed under vacuum. The residue was suspended in 10% aqueous $NaHCO_3$, and the suspension extracted with EtOAc (2×50 mL). The combined organic extracts were dried over $MgSO_4$, filtered and evaporated to yield a white solid. The solid was dissolved in MeOH (1 mL) and subjected to column chromatography (40×350 mm) on silica gel with 20% MeOH/$CHCl_3$. Fractions containing product were pooled and evaporated to yield a white solid (the balance of recovered material was the deprotected 2-chloro derivative). The crude product was dissolved in MeOH and subjected to column chromatography (40×350 mm) on C18-reverse phase silica gel with 75% MeOH/$H_2O$. Fractions containing product were pooled and evaporated to yield 50 mg (42%) of 4.25 as a white crystalline solid: mp 198-199° C.; $R_f$ 0.2 (10% MeOH/$CHCl_3$); $^1$H-NMR (500 MHz, DMSO-$d_6$): δ 10.21 (s, 1H), 8.34 (s, 1H), 8.31 (s, 1H), 5.84 (d, 1H), 5.41 (d, 1H, $D_2O$ exch.), 5.30 (t, 1H, $D_2O$ exch.), 5.23 (d, 1H, $D_2O$ exch.), 4.41 (q, 4H), 4.13 (s, 1H), 3.95 (d, 1H), 3.69 (m, 2H). $^{13}$C-NMR (125 MHz, DMSO-$d_6$): δ 183.28, 160.04, 129.51, 125.21, 124.83, 124.68, 121.12, 114.73, 100.30, 86.81, 85.93, 71.06, 69.75, 64.78, 61.18. HRMS (EI) m/z calcd. for $C_{15}H_{15}Cl_2NO_6$ 375.0276, found 375.0278. Anal calcd for $C_{15}H_{15}Cl_2NO_6$: C, 47.89; H, 4.02; N, 3.72. Found: C, 47.73; H, 4.12; N, 3.72.

5,6-Dichloro-2-methoxy-3-cyano-1-(β-D-ribofuranosyl)indole (4.26)

2,5,6-Trichloro-3-cyano-1-(β-D-ribofuranosyl)indole (4.4, 100 mg, 0.27 mmol) was dissolved in dry MeOH (10 mL) to which was added sodium methoxide (100 mg, 1.9 mmol). The resulting solution heated at reflux for 2 h, then cooled to room temperature and the solvent evaporated. The residual solid was recrystallized from MeOH/$H_2O$ to yield 68 mg (63%) of 4.26 as a white powder: mp 245-246° C.; $R_f$ 0.2 (10% MeOH/$CHCl_3$); $^1$H-NMR (500 MHz, DMSO-$d_6$): δ 8.36 (s, 1H), 7.65 (s, 1H), 5.80 (d, 1H), 5.37 (d, 1H, $D_2O$ exch.), 5.28 (t, 1H, $D_2O$ exch.), 5.20 (d, 1H, $D_2O$ exch.), 4.39-4.37 (m, 4H), 4.10 (m, 1H), 3.93 (d, 1H), 3.66 (m, 2H). $^{13}$C-NMR (125 MHz, DMSO-$d_6$): δ 158.44, 128.52, 126.05, 125.01, 124.81, 118.21, 115.02, 114.47, 86.89, 85.86, 71.06, 69.67, 65.16, 61.10, 60.81. HRMS (EI) m/z calcd. for $C_{15}H_{14}Cl_2N_2O_5$ 372.0280, found 372.0265. Anal calcd for $C_{15}H_{14}Cl_2N_2O_5$: C, 48.28; H, 3.78; N, 7.51. Found: C, 47.97; H, 3.75; N, 7.34.

2,5,6-Trichloro-3-[(4-semicarbazono)methylidene]-1-(β-D-ribofuranosyl)indole (4.27)

2,5,6-Trichloro-3-formyl-1-(β-D-ribofuranosyl)indole (4.3, 76 mg, 0.20 mmol) was dissolved in methanol (3 mL) to which was added a solution of semicarbazide hydrochloride (2.0 M, 0.20 mL, 0.40 mmol) and 2 drops of pyridine. The solution was warmed to 60 C for 10 min, then stirred at room temperature for 16 h, during which time a fine white precipitate had developed. The suspension was cooled at 4 C for 4 h, then the solids were collected by filtration and rinsed with cold water. The solids were dried under vacuum (0.5 mmHg, 65° C.) for 12 h to yield a white crystalline solid which was recrystallized from MeOH to yield 49 mg (56%) of 4.27 as a white powder: mp dec. >250 C; $R_f$ 0.1 (10% MeOH/$CHCl_3$); $^1$H-NMR (500 MHz, DMSO-$d_6$): δ 10.19 (s, 1H, $D_2O$ exch.), 8.50 (s, 1H), 8.48 (s, 1H), 8.39 (s, 1H), 8.07 (s, 1H), 6.40 (s, 2H, $D_2O$ exch.), 5.91 (d, 1H), 5.38 (d, 1H, $D_2O$ exch.), 5.35 (t, 1H, $D_2O$ exch.), 5.23 (d, 1H, $D_2O$ exch.), 4.41 (q, 1H), 4.13 (s, 1H), 3.97 (d, 1H), 3.70 (d, 2H). $^{13}$C-NMR (125 MHz, DMSO-$d_6$): δ 156.51, 133.73, 133.05, 128.96, 125.99, 124.92, 123.71, 122.27, 115.13, 108.53, 88.71, 85.99, 71.29, 69.64, 61.10. HRMS (EI) m/z calcd. for $C_{15}H_{15}Cl_3N_4O_5$ 436.0108, found 436.090. Anal calcd for $C_{15}H_{15}Cl_3N_4O_4S$: C, 41.16; H, 3.45; N, 12.80. Found: C, 40.97; H, 3.67; N, 12.63.

2,5,6-Trichloro-3-[(4-thiosemicarbazono)methylidene]-1-(β-D-ribofuranosyl)indole (4.28)

2,5,6-Trichloro-3-formyl-1-(β-D-ribofuranosyl)indole (4.3, 94 mg, 0.25 mmol) was dissolved in methanol (10 mL) to which was added thiosemicarbazide (24 mg, 0.26 mmol). The solution was stirred at room temperature for 16 h, during which time a fine white precipitate had developed. The suspension was cooled at 4 C for 4 h, then the solids were collected by filtration and rinsed with cold water. The solids were dried under vacuum (0.5 mmHg, 65° C.) for 12 h to yield 72 mg (65%) of 4.28 as a white powder: mp dec. >225 C; $R_f$ 0.7 (20% MeOH/CHCl$_3$); $^1$H-NMR (500 MHz, DMSO-d$_6$): δ 11.36 (s, 1H, D$_2$O exch.), 8.53 (s, 1H), 8.48 (s, 1H), 8.35 (s, 1H), 8.19 (s, 1H, D$_2$O exch.), 7.84 (s, 1H, D$_2$O exch.), 5.94 (d, 1H), 5.41 (d, 1H, D$_2$O exch.), 5.37 (t, 1H, D$_2$O exch.), 5.25 (d, 1H, D$_2$O exch.), 4.42 (q, 1H), 4.15 (m, 1H), 3.99 (m, 1H), 3.72 (m, 2H). $^{13}$C-NMR (125 MHz, DMSO-d$_6$): δ 177.23, 137.32, 133.09, 126.22, 125.28, 123.50, 122.63, 115.06, 108.11, 88.84, 86.11, 71.35, 69.63, 61.08. HRMS (ES) m/z calcd. for C$_{15}$H$_{15}$Cl$_3$N$_4$O$_4$S·Na 472.9777, found 474.9789. Anal calcd for C$_{15}$H$_{15}$Cl$_3$N$_4$O$_4$S·¼MeOH: C, 39.67; H, 3.49; N, 12.13. Found: C, 39.43; H, 3.29; N, 12.06.

2,5,6-Trichloro-3-(N-hydroxyiminomethylidene)-1-(β-D-ribofuranosyl)indole (4.29)

To a solution of 2,5,6-trichloro-3-formyl-1-(β-D-ribofuranosyl)indole (4.3, 170 mg, 0.45 mmol) in MeOH (10 mL) was added a solution of methoxylamine hydrochloride (39 mg, 0.56 mmol) and sodium bicarbonate (49 mg, 0.48 mmol) in water (2.0 mL). The resulting mixture was stirred at room temperature for 16 h, then the solvent was evaporated to provide a pale yellow residue. The residue was suspended in 20 mL of 5% aqueous sodium thiosulfate and extracted with EtOAc (2×50 mL). The combined organic extracts were washed with brine (25 mL), dried over MgSO$_4$, filtered and evaporated to yield a pink residue. The residue was subjected to column chromatography (40×350 mm) on C18 reverse-phase silica gel with 75% MeOH/H$_2$O. The appropriate UV-active fractions were pooled and evaporated to yield 124 mg (70%) of 4.29 as a white powder. A portion was recrystallized from Et$_2$O/hexane to yield a white crystalline solid: mp 208-209 C; R$_f$ 0.2 (10% MeOH/CHCl$_3$); $^1$H NMR (500 MHz, DMSO-d$_6$) δ 11.31 (s, 1H), 8.54 (s, 1H), 8.22 (s, 1H), 8.19 (s, 1H), 5.93 (d, 1H), 5.37 (m, 2H, D$_2$O exch.), 5.25 (m, 1H, D$_2$O exch.), 4.43 (m, 1H), 4.16 (m, 1H), 3.99 (m, 1H), 3.73 (m, 2H). $^{13}$C NMR (125 MHz, DMSO-d$_6$) δ 141.30, 133.03, 128.48, 125.85, 124.73, 124.05, 121.76, 115.31, 106.70, 88.81, 86.02, 71.39, 69.65, 61.11. HRMS (EI) m/z calcd. for C$_{14}$H$_{13}$Cl$_3$N$_2$O$_5$ 393.9890, found 393.9892. Anal calcd for C$_{14}$H$_{13}$Cl$_3$N$_2$O$_5$·½Et$_2$O: C, 44.41; H, 4.19; N, 6.47. Found: C, 44.16; H, 4.18; N, 6.48.

2,5,6-Trichloro-3-(N-methoxyiminomethylidene)-1-(β-D-ribofuranosyl)indole (4.30)

To a solution of 2,5,6-trichloro-3-formyl-1-(β-D-ribofuranosyl)indole (4.3, 103 mg, 0.27 mmol) in MeOH (5 mL) was added a solution of methoxylamine hydrochloride (27 mg, 0.32 mmol) and sodium bicarbonate (22 mg, 0.26 mmol) in water (1.0 mL). The resulting mixture was stirred at room temperature for 16 h, then the solvent was evaporated to provide a pale yellow residue. The residue was suspended in 10 mL of 5% aqueous sodium thiosulfate and extracted with EtOAc (2×25 mL). The combined organic extracts were washed with brine (10 mL), dried over MgSO$_4$, filtered and evaporated to yield a yellow residue. The residue was subjected to column chromatography (40×350 mm) on C18 reverse-phase silica gel with 80% MeOH/H$_2$O. The appropriate UV-active fractions were pooled and evaporated to yield a white powder. The powder was recrystallized from Et$_2$O to yield 45 mg (41%) of 4.30 as a white crystalline solid: mp 197-198 C; R$_f$ 0.4 (10% MeOH/CHCl$_3$); $^1$H NMR (500 MHz, DMSO-d$_6$) δ 8.57 (s, 1H), 8.27 (s, 1H), 8.17 (s, 1H), 5.93 (d, 1H), 5.42 (d, 1H, D$_2$O exch.), 5.40 (t, 1H, D$_2$O exch.), 5.27 (d, 1H, D$_2$O exch.), 4.42 (q, 1H), 4.14 (m, 1H), 4.00 (d, 1H), 3.96 (s, 3H), 3.71 (m, 2H). $^{13}$C NMR (125 MHz, DMSO-d$_6$) δ 141.84, 133.04, 129.74, 126.09, 125.03, 123.82, 121.70, 115.46, 105.59, 88.85, 86.13, 71.43, 69.65, 61.84, 61.09. HRMS (EI) m/z calcd. for C$_{15}$H$_{15}$Cl$_3$N$_2$O$_5$ 408.0047, found 408.0047. Anal calcd for C$_{15}$H$_{15}$Cl$_3$N$_2$O$_5$: C, 43.98; H, 3.69; N, 6.84. Found: C, 43.79; H, 3.68; N, 6.61.

2,5,6-Trichloro-3-[N-(methoxycarbonylamino)iminomethylidene]-1-(β-D-ribofuranosyl)indole (4.31)

2,5,6-Trichloro-3-formyl-1-(β-D-ribofuranosyl)indole (4.3, 122 mg, 0.32 mmol) was dissolved in MeOH (10 mL) to which was added methyl hydrazinocarboxylate (115 mg, 1.3 mmol). The resulting solution was heated on a 60 C oil bath for 16 h, then cooled to room temperature and poured into 100 mL of water, and the solvent evaporated to approx 50 mL. The resulting suspension was cooled to 4C, then filtered and the solids rinsed with cold water (25 mL). The solids were recrystallized from boiling EtOAc/hexane to yield 123 mg (85%) of 4.31 as a pale pink crystalline solid: mp 217-219 C; R$_f$ 0.2 (10% MeOH/CHCl$_3$); $^1$H-NMR (500 MHz, DMSO-d$_6$): δ 11.17 (b, 1H, D$_2$O exch.), 8.54 (s, 1H), 8.42 (s, 1H), 8.22 (b, 1H), 5.92 (d, 1H), 5.42-5.37 (m, 2H, D$_2$O exch.), 5.25 (d, 1H, D$_2$O exch.), 4.43 (q, 1H), 4.15 (d, 1H), 3.98 (d, 1H), 3.72 (b, 5H). $^{13}$C-NMR (125 MHz, DMSO-d$_6$): δ 153.88, 133.17, 129.33, 126.08, 124.96, 124.06, 122.17, 115.34, 108.59, 88.76, 86.03, 71.30, 69.73, 69.62, 61.07, 52.04. HRMS (ES) m/z calcd. for C$_{16}$H$_{16}$Cl$_3$N$_3$O$_6$·Na 474.0002, found 473.9999. Anal calcd for C$_{16}$H$_{16}$Cl$_3$N$_3$O$_6$·¼H$_2$O: C, 42.03; H, 3.64; N, 9.19. Found: C, 42.11; H, 3.92; N, 9.18.

2,5,6-Trichloro-3-[N-(acetylamino)iminomethylidene]-1-(β-D-ribofuranosyl)indole (4.32)

2,5,6-Trichloro-3-formyl-1-(β-D-ribofuranosyl)indole (4.3, 109 mg, 0.29 mmol) was dissolved in MeOH (5 mL) to which was added acethydrazine (85 mg, 1.1 mmol). The resulting solution was heated on a 45 C oil bath for 16 h, then cooled to room temperature and poured into 15 mL of water. The resulting suspension was cooled to 4C, then filtered and the solids rinsed with cold water (25 mL). The solids were dissolved in DMF (0.5 mL) and subjected to column chromatography (40×350 mm) on C18-reverse phase silica gel with 75% MeOH/H$_2$O. Fractions containing product were pooled and evaporated to yield a white crystalline solid, which was recrystallized from acetone/MeOH to yield 70 mg (56%) of 4.32 as a white microcrystalline solid which is an inseparable mixture of isomers in a ratio of 60:40: mp 270-271 C; R$_f$ 0.2 (10% MeOH/CHCl$_3$); $^1$H-NMR (500 MHz, DMSO-d$_6$): (major isomer) δ 11.25 (s, 1H, D$_2$O exch.), 8.56 (s, 1H), 8.27 (s, 1H), 8.18 (s, 1H), 5.94 (d, 1H), 5.40-5.36 (m, 2H, D$_2$O exch.), 5.25 (d, 1H, D$_2$O exch.), 4.42 (q, 1H), 4.13 (s, 1H), 3.98 (s, 1H), 3.70 (s, 2H), 2.24 (s, 3H); (minor isomer) δ 11.41 (s, 1H, D$_2$O exch.), 8.56 (s, 1H), 8.44 (s, 1H), 8.32 (s, 1H), 5.94 (d, 1H), 5.40-5.36 (m, 2H, D$_2$O exch.), 5.25 (d, 1H, D$_2$O exch.), 4.42 (q, 1H), 4.13 (s, 1H), 3.98 (s, 1H), 3.70 (s, 2H), 1.95 (s, 3H). $^{13}$C-NMR (125 MHz, DMSO-d$_6$): (major isomer) δ 171.39, 135.98, 133.15, 129.73, 126.01, 124.96, 123.86, 121.69, 115.41, 108.31, 88.78, 86.09, 71.41, 69.66, 61.10, 20.36; (minor isomer) δ 165.24, 138.70, 133.12, 129.82, 126.06, 124.96, 123.99, 122.17, 115.33, 108.51, 88.78, 86.09, 71.41, 69.66, 61.10, 21.67. HRMS (ES) m/z calcd. for C$_{16}$H$_{16}$Cl$_3$N$_3$O$_5$·Na 458.0053, found 458.0043. Anal calcd for C$_{16}$H$_{16}$Cl$_3$N$_3$O$_5$: C, 44.01; H, 3.69; N, 9.62. Found: C, 43.76; H, 3.75; N, 9.67.

2,5,6-Trichloro-1-(β-D-ribofuranosyl)indole-3-carboxamide oxime (4.33)

2,5,6-Trichloro-3-cyano-1-(β-D-ribofuranosyl)indole (4.4, 107 mg, 0.28 mmol) was dissolved in dry MeOH (5 mL) and dry DMF (1 mL) to which were added hydroxylamine hydrochloride (0.50 g, 7.2 mmol) and potassium hydroxide (0.39 g, 7.0 mmol). The resulting suspension was stirred at room temperature for 16 h, then poured into brine (25 mL) and water (25 mL), and the resulting aqueous suspension extracted with EtOAc (2×100 mL). The combined organic extracts were dried over $MgSO_4$, filtered and evaporated to yield a clear oil which was dissolved in MeOH (1 mL) and subjected to column chromatography (40×350 mm) on C18-reverse phase silica gel with 75% $MeOH/H_2O$. Fractions containing product were pooled and evaporated to yield a light tan solid which was recrystallized from $MeOH/H_2O$ to yield 81 mg (70%) of 4.33 as a light tan solid: mp dec >150 C; $R_f$ 0.4 (20% $MeOH/CHCl_3$); $^1$H-NMR (500 MHz, DMSO-$d_6$): δ 9.71 (s, 1H, $D_2O$ exch.), 8.47 (s, 1H), 7.97 (s, 1H), 5.95 (d, 1H), 5.78 (s, 2H, $D_2O$ exch.), 5.36-5.33 (m, 2H, $D_2O$ exch.), 5.23 (d, 1H, $D_2O$ exch.), 4.44 (q, 1H), 4.14 (m, 1H), 3.96 (d, 1H), 3.71 (m, 2H). $^{13}$C-NMR (125 MHz, DMSO-$d_6$): δ 145.92, 132.24, 125.86, 125.78, 125.10, 123.92, 121.27, 114.85, 107.15, 88.61, 85.77, 71.24, 69.59, 61.09. HRMS (EI) m/z calcd. for $C_{14}H_{14}Cl_3N_3O_5$ 408.9999, found 408.9999. Anal calcd for $C_{14}H_{14}Cl_3N_3O_5$: C, 40.95; H, 3.44; N, 10.23. Found: C, 40.89; H, 3.61; N, 10.08.

Methyl 2,5,6-Trichloro-1-(β-D-ribofuranosyl)indole-3-formimidate (4.34)

2,5,6-Trichloro-3-cyano-1-(β-D-ribofuranosyl)indole (4.4, 107 mg, 0.28 mmol) was dissolved in dry MeOH (10 mL) which was cooled to 0 C in an ice bath. Hydrogen chloride gas was slowly bubbled through the solution for 2 h, then the reaction vessel was tightly capped, and the resulting solution was stirred at room temperature for 24 h. The acidic solution was diluted with $Et_2O$ (20 mL) and evaporated to dryness. The residual solid was suspended in 10% aqueous $NaHCO_3$ (100 mL) and extracted with EtOAc (3×100 mL, with vigorous shaking). The combined organic extracts were dried over $MgSO_4$, filtered and evaporated to yield a white solid which was dissolved in DMF (0.5 mL) and subjected to column chromatography (40×350 mm) on C18-reverse phase silica gel with 75% $MeOH/H_2O$. Fractions containing product were pooled and evaporated to yield 64 mg (58%) of 4.34 as a white crystalline solid: mp 248-249 C; $R_f$ 0.6 (20% $MeOH/CHCl_3$); $^1$H-NMR (500 MHz, DMSO-$d_6$): δ 8.55 (s, 1H), 8.43 (s, 1H, $D_2O$ exch.), 7.96 (s, 1H), 5.98 (d, 1H), 5.39 (d, 1H, $D_2O$ exch.), 5.37 (t, 1H, $D_2O$ exch.), 5.24 (d, 1H, $D_2O$ exch.), 4.41 (q, 1H), 4.14 (s, 1H), 3.98 (d, 1H), 3.85 (s, 3H), 3.71 (m, 2H). $^{13}$C-NMR (125 MHz, DMSO-$d_6$): δ 161.40, 132.01, 128.23, 125.67, 124.82, 124.50, 121.32, 115.19, 106.29, 88.73, 86.08, 71.40, 69.50, 60.99, 52.45. HRMS (EI) m/z calcd. for $C_{15}H_{15}Cl_3N_2O_5$ 408.0047, found 408.0043. Anal calcd for $C_{15}H_{15}Cl_3N_2O_5$: C, 43.98; H, 3.69; N, 6.84. Found: C, 43.97; H, 3.81; N, 6.75.

2,5,6-Trichloro-3-[N-(dimethylamino)iminomethylidene]-1-(β-D-ribofuranosyl)indole (4.35)

2,5,6-Trichloro-3-formyl-1-(β-D-ribofuranosyl)indole (4.3, 100 mg, 0.26 mmol) was dissolved in MeOH (5 mL) to which was added asym-dimethylhydrazine (0.5 mL). The resulting solution was stirred at room temperature for 16 h, then evaporated under vacuum to yield a yellow residue. The residue was dissolved in DMF (0.5 mL) and subjected to column chromatography (40×350 mm) on silica gel with 10% $MeOH/CHCl_3$. Fractions containing product were pooled and evaporated to yield 87 mg (78%) of 4.35 as a white powder: mp dec >170° C.; $R_f$ 0.4 (10% $MeOH/CHCl_3$); $^1$H-NMR (500 MHz, DMSO-$d_6$): δ 8.44 (s, 1H), 8.36 (s, 1H), 7.35 (s, 1H), 5.91 (d, 1H), 5.36-5.31 (m, 2H, $D_2O$ exch.), 5.21 (d, 1H, $D_2O$ exch.), 4.42 (q, 1H), 4.13 (s, 1H), 3.96 (d, 1H), 3.70 (b, 2H), 2.93 (s, 6H). $^{13}$C-NMR (125 MHz, DMSO-$d_6$): δ 133.01, 125.64, 125.62, 125.37, 124.26, 124.04, 121.97, 114.85, 110.14, 88.58, 85.75, 71.18, 69.66, 61.14, 42.58. HRMS (ES) m/z calcd. for $C_{16}H_{18}Cl_3N_3O_4$·Na 444.0261, found 444.0269. Anal calcd for $C_{16}H_{18}Cl_3N_3O_4$: C, 45.46; H, 4.29; N, 9.94. Found: C, 45.79; H, 4.61; N, 10.06.

5,6-Dichloro-1-methyl-8-(β-D-ribofuranosyl)pyrazolo[3,4-b]indole (4.36)

2,5,6-Trichloro-3-formyl-1-(β-D-ribofuranosyl)indole (4.3, 82 mg, 0.22 mmol) was dissolved in methanol (4 mL) to which was added methylhydrazine (0.5 mL). The solution was stirred at room temperature for 16 h, then the solvent was removed under vacuum. The residue was suspended in 20 mL of brine and extracted with EtOAc (2×20 mL). The combined organic extracts were dried over $MgSO_4$, filtered and evaporated to yield a yellow oil. The oil was subjected to column chromatography (40×350 mm) on C18-reverse phase silica gel with 75% MeOH/water. Fractions containing product were pooled and evaporated to yield 29 mg (33%) of 4.36 as a pale yellow solid: mp 135-138° C.; $R_f$ 0.6 (20% $MeOH/CHCl_3$); $^1$H-NMR (500 MHz, DMSO-$d_6$): δ 8.25 (s, 1H), 7.94 (s, 1H), 7.73 (s, 1H), 5.95 (d, 1H), 5.38 (d, 1H, $D_2O$ exch.), 5.25 (m, 2H, $D_2O$ exch.), 4.21 (q, 1H), 4.13 (m, 1H), 4.05 (s, 3H), 3.97 (m, 1H), 3.74 (m, 2H). $^{13}$C-NMR (125 MHz, DMSO-$d_6$): δ 146.23, 139.94, 128.98, 123.94, 122.80, 120.16, 119.24, 115.28, 109.15, 88.91, 85.71, 71.94, 68.75, 60.89, 37.81. HRMS (ES) m/z calcd. for $C_{15}H_{15}Cl_2N_3O_4$·Na·MeOH 426.0599, found 426.0593. Anal calcd for $C_{15}H_{15}Cl_2N_3O_4$: C, 48.40; H, 4.06; N, 11.29. Found: C, 48.13; H, 4.16; N, 11.12.

5,6-Dichloro-3-amino-8-(β-D-ribofuranosyl)pyrazolo[3,4-b]indole (4.37)

2,5,6-Trichloro-3-cyano-1-(β-D-ribofuranosyl)indole (4.4, 102 mg, 0.27 mmol) was dissolved in hydrazine hydrate (2 mL), and the resulting solution was stirred at room temperature for 30 min. The suspension thus obtained was diluted with water (8 mL), cooled to 0 °C, and the suspension filtered and the solids rinsed with water. The solids were recrystallized from $MeOH/H_2O$ to yield 91 mg (90%) of 4.37 as a white crystalline solid: mp 198-201 °C; $R_f$ 0.3 (20% $MeOH/CHCl_3$); $^1$H-NMR (500 MHz, DMSO-$d_6$): δ 8.68 (s, 1H, $D_2O$ exch.), 7.76 (s, 1H), 7.27 (s, 1H), 5.81 (d, 1H), 5.78 (b, 1H, $D_2O$ exch.), 5.31-5.28 (m, 2H, $D_2O$ exch.), 4.84 (s, 2H, $D_2O$ exch.), 4.27 (q, 1H), 4.07 (s, 1H), 4.00 (s, 1H), 3.68 (q, 2H). $^{13}$C-NMR (125 MHz, DMSO-$d_6$): δ 155.50, 131.99, 129.00, 123.60, 121.60, 116.91, 115.45, 111.96, 88.32, 85.95, 71.06, 69.95, 63.28, 60.78. HRMS (EI) m/z calcd. for $C_{14}H_{14}Cl_2N_4O_4$ 372.0392, found 372.0397. Anal calcd for $C_{14}H_{14}Cl_2N_4O_4$·¼$H_2O$: C, 44.52; H, 3.87; N, 14.83. Found: C, 44.63; H, 4.10; N, 14.72.

2,5,6-Trichloro-3-acetyl-1-(5-O-acetyl-β-D-ribofuranosyl)indole (4.43)

2,5,6-Trichloro-3-acetyl-1-(2,3-O-isopropylidene-5-O-acetyl-β-D-ribofuranosyl)indole (4.40, 375 mg, 0.79 mmol)

was dissolved in 90% aqueous trifluoroacetic acid (10 mL) and stirred at room temperature for 5 min. The solvent was then removed under vacuum and the residue dissolved in EtOAc (100 mL). The organic solution was washed with 10% aqueous NaHCO$_3$ (50 mL), dried over MgSO$_4$, filtered and evaporated to yield a pale yellow solid. The solid was dissolved in MeOH (1 mL) and was subjected to column chromatography (40×350 mm) on silica gel with 10% MeOH/CHCl$_3$. Fractions containing product were pooled and evaporated to yield a clear glass, which was recrystallized from boiling hexane/CHCl$_3$ to yield 318 mg (93%) of 4.43 as a white crystalline solid: mp 178-179 C; R$_f$ 0.5 (10% MeOH/CHCl$_3$); $^1$H-NMR (500 MHz, DMSO-d$_6$): δ 8.43 (s, 1H), 7.97 (s, 1H), 6.07 (d, 1H), 5.56 (d, 1H, D$_2$O exch.), 5.48 (d, 1H, D$_2$O exch.), 4.46 (dd, 1H) 4.42 (dd, 1H), 4.17-4.12 (m, 2H) 2.63 (s, 3H), 2.16 (s, 3H). $^{13}$C-NMR (125 MHz, DMSO-d$_6$): δ 192.21, 170.27, 133.05, 132.43, 126.18, 126.12, 125.76, 122.32, 113.93, 113.25, 89.30, 82.57, 71.45, 68.84, 63.43, 30.76, 20.85. HRMS (ES) m/z calcd. for C$_{17}$H$_{16}$Cl$_3$NO$_6$·Na 457.9941, found 457.9935. Anal calcd for C$_{17}$H$_{16}$Cl$_3$NO$_6$: C, 46.38; H, 3.75; N, 3.18. Found: C, 46.43; H, 3.70; N, 3.40.

2,5,6-Trichloro-3-propionyl-1-(5-O-acetyl-β-D-ribofuranosyl)indole (4.44)

2,5,6-Trichloro-3-acetyl-1-(2,3-O-isopropylidene-5-O-propionyl-β-D-ribofuranosyl)indole (4.41, 178 mg, 0.36 mmol) was dissolved in 90% aqueous trifluoroacetic acid (10 mL) and stirred at room temperature for 2 min. The solvent was then removed under vacuum and the residue dissolved in EtOAc (100 mL). The organic solution was washed with 10% aqueous NaHCO$_3$ (50 mL), then dried over MgSO$_4$, filtered and evaporated to yield a pale yellow solid. The solid was recrystallized from warm MeOH to yield 152 mg (93%) of 4.44 as a white crystalline solid: mp 168-169 C; R$_f$ 0.6 (10% MeOH/CHCl$_3$); $^1$H-NMR (500 MHz, DMSO-d$_6$): δ 8.45 (s, 1H), 7.97 (s, 1H), 6.07 (d, 1H), 5.54 (d, 1H, D$_2$O exch.), 5.46 (d, 1H, D$_2$O exch.), 4.46 (dd, 1H), 4.42 (t, 1H), 4.27 (dd, 1H), 4.17-4.12 (m, 2H), 3.03 (q, 2H), 2.16 (s, 3H), 1.12 (t, 3H). $^{13}$C-NMR (125 MHz, DMSO-d$_6$): δ 195.16, 170.26, 132.45, 132.35, 126.10, 126.03, 125.87, 122.39, 113.87, 112.87, 89.27, 82.52, 71.42, 68.83, 63.41, 35.08, 20.84, 7.91. HRMS (ES) m/z calcd. for C$_{18}$H$_{18}$Cl$_3$NO$_6$·Na 472.0097, found 472.0097. Anal calcd for C$_{18}$H$_{18}$Cl$_3$NO$_6$: C, 47.97; H, 4.03; N, 3.11. Found: C, 47.74; H, 3.99; N, 3.39.

2,5,6-Trichloro-3-acetyl-1-(β-D-ribofuranosyl)indole (4.46)

2,5,6-Trichloro-3-acetyl-1-(5-O-acetyl-β-D-ribofuranosyl)indole (4.43, 232 mg, 0.53 mmol) was dissolved in dry MeOH (20 mL) to which was added sodium methoxide (35 mg, 0.65 mmol). The solution was stirred at room temperature for 45 min, and the solvent was then removed under vacuum. The residue was suspended in 10% aqueous NaHCO$_3$ (50 mL) and the suspension extracted with EtOAc (2×50 mL). The combined organic extracts were dried over MgSO$_4$, filtered and evaporated to yield a white solid. The solid was recrystallized from boiling EtOAc/hexane to yield 170 mg (81%) of 4.46 as a white crystalline solid: mp 249-250 C; R$_f$ 0.4 (10% MeOH/CHCl$_3$); $^1$H-NMR (500 MHz, DMSO-d$_6$): δ 8.63 (s, 1H), 8.41 (s, 1H), 6.07 (d, 1H), 5.45-5.42 (m, 2H, D$_2$O exch.), 5.30 (d, 1H, D$_2$O exch.), 4.44 (q, 1H), 4.17 (d, 1H), 4.03 (d, 1H), 3.75 (b, 2H), 2.63 (s, 3H). $^{13}$C-NMR (125 MHz, DMSO-d$_6$): δ 192.17, 133.10, 132.38, 126.21, 126.00, 125.73, 122.00, 115.44, 112.99, 88.97, 86.39, 71.63, 69.54, 60.97, 30.72. HRMS (ES) m/z calcd. for C$_{15}$H$_{14}$Cl$_3$NO$_5$·Na 415.9835, found 415.9843. Anal calcd for C$_{15}$H$_{14}$Cl$_3$NO$_5$: C, 45.65; H, 3.58; N, 3.55. Found: C, 45.75; H, 3.78; N, 3.61.

2,5,6-Trichloro-3-propionyl-1-(β-D-ribofuranosyl)indole (4.47)

2,5,6-Trichloro-3-propionyl-1-(5-O-acetyl-β-D-ribofuranosyl)indole (4.44, 90 mg, 0.21 mmol) was dissolved in dry MeOH (15 mL) to which was added sodium methoxide (14 mg, 0.26 mmol). The solution was stirred at room temperature for 40 min, and the solvent was then removed under vacuum. The residue was suspended in brine (50 mL) and water (5 mL), and the suspension extracted with EtOAc (2×50 mL). The combined organic extracts were dried over MgSO$_4$, filtered and evaporated to yield a white solid. The solid was dissolved in 10% MeOH/CHCl$_3$ (1 mL) and subjected to column chromatography (40×350 mm) on silica gel with 10% MeOH/CHCl$_3$. Fractions containing product were pooled and evaporated to yield a white solid which was recrystallized from boiling EtOAc to yield 170 mg (81%) of 4.47 as a white crystalline solid: mp 239-240 C; R$_f$ 0.3 (10% MeOH/CHCl$_3$); $^1$H-NMR (500 MHz, DMSO-d$_6$): δ 8.63 (s, 1H), 8.44 (s, 1H), 6.06 (d, 1H), 5.44-5.41 (m, 2H, D$_2$O exch.), 5.29 (d, 1H, D$_2$O exch.), 4.42 (q, 1H), 4.17 (s, 1H), 3.74 (m, 2H), 3.04 (dd, 2H), 1.12 (t, 3H). $^{13}$C-NMR (125 MHz, DMSO-d$_6$): δ 195.17, 132.45, 132.41, 126.13, 125.91, 125.84, 122.09, 115.39, 112.60, 88.90, 86.36, 71.58, 69.54, 60.97, 35.05, 7.98. HRMS (EI) m/z calcd. for C$_{16}$H$_{16}$Cl$_3$NO$_5$ 407.0094, found 407.0089. Anal calcd for C$_{16}$H$_{16}$Cl$_3$NO$_5$: C, 47.02; H, 3.95; N, 3.43. Found: C, 46.85; H, 3.96; N, 3.47.

2,5,6-Trichloro-3-trifluoroacetyl-1-(β-D-ribofuranosyl)indole (4.48)

2,5,6-Trichloro-3-trifluoroacetyl-1-(5-O-acetyl-β-D-ribofuranosyl)indole (4.45, 94 mg, 0.19 mmol) was dissolved in dry MeOH (20 mL) to which was added sodium methoxide (12 mg, 0.22 mmol). The solution was stirred at room temperature for 90 min, then the solvent was removed under vacuum. The residue was suspended in brine (40 mL) and water (5 mL), and the suspension extracted with EtOAc (2×50 mL). The combined organic extracts were dried over MgSO$_4$, filtered and evaporated to yield a yellow-orange solid. The solid was dissolved in 10% MeOH/CHCl$_3$ (1 mL) and subjected to column chromatography (40×350 mm) on silica gel with 10% MeOH/CHCl$_3$. Fractions containing product were pooled and evaporated to yield a white solid which was recrystallized from MeOH/H$_2$O to yield 48 mg (56%) of 4.48 as a pale yellow powder: mp 179-180 C; R$_f$ 0.3 (10% MeOH/CHCl$_3$); $^1$H-NMR (500 MHz, DMSO-d$_6$): δ 8.80 (s, 1H), 8.23 (s, 1H), 6.14 (d, 1H), 5.50 (b, 2H, D$_2$O exch.), 5.34 (b, 1H, D$_2$O exch.), 4.44 (t, 1H), 4.19 (dd, 1H), 4.06 (d, 1H), 3.76 (dq, 2H). $^{13}$C-NMR (125 MHz, DMSO-d$_6$): δ 173.47 (J=37 Hz), 132.34, 132.65, 127.38, 127.28, 125.47, 121.35, 116.29, 115.88 (J=289 Hz), 106.90, 89.42, 86.88, 71.96, 69.49, 60.86. $^{19}$F-NMR (300 MHz, DMSO-d$_6$): δ -72.34. HRMS (EI) m/z calcd. for C$_{15}$H$_{11}$Cl$_3$F$_3$NO$_5$ 446.9655, found 446.9661. Anal calcd for C$_{15}$H$_{11}$Cl$_3$F$_3$NO$_5$: C, 40.16; H, 2.47; N, 3.12. Found: C, 40.18; H, 2.60; N, 2.98.

2,5,6-Trichloro-3-methyl-1-(β-D-ribofuranosyl)indole (4.62)

2,5,6-Trichloro-3-methyl-1-(2,3-dideoxy-2,3-didehydro-β-D-ribofuranosyl)indole (4.61, 212 mg, 0.64 mmol) was dissolved in acetone (8 mL) and water (1 mL) to which were added N-methylmorpholine-N-oxide (0.20 g, 1.7 mmol) and 2.5% osmium tetroxide solution in t-BuOH (0.65 mL, 0.065 mmol). The resulting solution was stirred at room temperature for 2 h, then additional N-methylmorpholine-N-oxide (0.20 g, 1.7 mmol) was added, and the solution was stirred at room temperature for an additional 16 h. The solvent volume was then reduced to approx 2 mL, and the solution was poured into 5% aqueous sodium thiosulfate (30 mL). The resulting mixture was extracted with EtOAc (2×30 mL), and the combined organic extracts were dried over MgSO$_4$, filtered and evaporated to yield an orange oil. The oil was dissolved in 50% MeOH/CHCl$_3$ (1 mL) and subjected to column chromatography (40×350 mm) on silica gel with 10% MeOH/CHCl$_3$. Fractions containing product were pooled and evaporated to yield 144 mg (62%) of 4.62 as a white powder: mp 190-191° C.; R$_f$ 0.4 (10% MeOH/CHCl$_3$); $^1$H-NMR (500 MHz, DMSO-d$_6$): δ 8.35 (s, 1H), 7.82 (s, 1H), 5.86 (d, 1H), 5.28 (d, 2H, D$_2$O exch.), 5.19 (d, 1H, D$_2$O exch. 4.40 (q, 1H), 4.11 (s, 1H), 3.93 (d, 1H), 3.69 (s, 2H), 2.21 (s, 3H). $^{13}$C-NMR (125 MHz, DMSO-d$_6$): δ 132.47, 127.73, 124.60, 123.18, 119.53, 114.58, 107.99, 88.66, 85.46, 79.19, 71.14, 69.68, 61.21, 8.34. HRMS (EI) m/z calcd. for C$_{14}$H$_{14}$Cl$_3$NO$_4$ 364.9988, found 364.9992. Anal calcd for C$_{14}$H$_{14}$Cl$_3$NO$_4$·½H$_2$O: C, 44.76; H, 4.02; N, 3.73. Found: C, 44.64; H, 3.93; N, 3.60.

2,3,5,6-Tetrachloro-1-(β-D-ribofuranosyl)indole (4.74)

2,3,5,6-Tetrachloro-1-(2,3-dideoxy-2,3-didehydro-β-D-ribofuranosyl)indole (4.72, 0.30 g, 0.85 mmol) was dissolved in acetone (12 mL) and water (3 mL) to which were added N-methylmorpholine-N-oxide (0.25 g, 2.1 mmol) and 2.5% osmium tetroxide solution in t-BuOH (1.0 mL, 0.10 mmol). The resulting solution was stirred at room temperature for 2 h. Additional N-methylnorpholine-N-oxide (0.25 g, 2.1 mmol) was then added, and the solution was stirred at room temperature for an additional 16 h. The solvent volume was then reduced to approx 5 mL, and the solution was poured into 5% aqueous sodium thiosulfate (125 mL). The resulting mixture was extracted with EtOAc (2×100 mL), and the combined organic extracts were washed with brine (50 mL), dried over MgSO$_4$, filtered and evaporated to yield a damp yellow solid. The crude material was dissolved in MeOH (1 mL) and subjected to column chromatography (40×350 mm) on silica gel with 10% MeOH/CHCl$_3$. Fractions containing product were pooled and evaporated to yield a yellow solid which was recrystallized from 50% MeOH/CHCl$_3$ and hexane to yield 0.60 g (48%) of 4.74 as a white powder: mp 197-198 C; R$_f$ 0.3 (10% MeOH/CHCl$_3$); $^1$H-NMR (500 MHz, DMSO-d$_6$): δ 8.56 (s, 1H), 7.77 (s, 1H), 5.90 (d, 1H), 5.40 (d, 1H, D$_2$O exch.), 5.37 (t, 1H, D$_2$O exch.), 5.25 (d, 1H, D$_2$O exch.), 4.40 (q, 1H), 4.14 (m, 1H), 3.99 (d, 1H), 3.71 (m, 2H). $^{13}$C-NMR (125 MHz, DMSO-d$_6$): δ 131.41, 126.21, 124.83, 124.61, 124.52, 118.26, 115.58, 102.47, 89.33, 86.05, 71.53, 69.66, 61.12. HRMS (EI) m/z calcd. for C$_{13}$H$_{11}$Cl$_4$NO$_4$ 384.9442, found 384.9450. Anal calcd for C$_{13}$H$_{11}$Cl$_4$NO$_4$: C, 40.34; H, 2.86; N, 3.62. Found: C, 40.24; H, 2.86; N, 3.46.

2,5,6-Trichloro-3-iodo-1-(β-D-ribofuranosyl)indole (4.75)

2,5,6-Trichloro-3-iodo-1-(2,3-dideoxy-2,3-didehydro-β-D-ribofuranosyl)indole (4.73, 0.77 g, 1.7 mmol) was dissolved in acetone (24 mL) and water (3 mL) to which were added N-methylmorpholine-N-oxide (0.51 g, 4.3 mmol) and 2.5% osmium tetroxide solution in t-BuOH (1.7 mL, 0.17 mmol). The resulting solution was stirred at room temperature for 2 h. Additional N-methylmorpholine-N-oxide (0.51 g, 4.3 mmol) was then added, and the solution was stirred at room temperature for an additional 16 h. The solvent volume was then reduced to approx 5 mL, and the solution was poured into 5% aqueous sodium thiosulfate (125 mL). The resulting mixture was extracted with EtOAc (2×100 mL), and the combined organic extracts were washed with brine (50 mL), dried over MgSO$_4$, filtered and evaporated to yield a damp yellow solid. The crude material was dissolved in MeOH (2 mL) and subjected to column chromatography (50×450 mm) on silica gel with 10% MeOH/CHCl$_3$. Fractions containing product were pooled and evaporated to yield a yellow solid which was recrystallized from 50% MeOH/CHCl$_3$ and hexane to yield 0.60 g (72%) of 4.75 as a white crystalline solid: mp 201-202 C; R$_f$ 0.3 (10% MeOH/CHCl$_3$); $^1$H-NMR (500 MHz, DMSO-d$_6$): δ 8.52 (s, 1H), 7.51 (s, 1H), 5.95 (d, 1H), 5.38 (d, 1H, D$_2$O exch.), 5.36 (t, 1H, D$_2$O exch.), 5.23 (d, 1H, D$_2$O exch.), 4.39 (q, 1H), 4.13 (m, 1H), 3.97 (d, 1H), 3.70 (m, 2H). $^{13}$C-NMR (125 MHz, DMSO-d$_6$): δ 132.95, 131.08, 129.77, 125.88, 124.68, 121.19, 115.32, 89.83, 85.90, 71.44, 69.59, 61.10. HRMS (EI) m/z calcd. for C$_{13}$H$_{11}$Cl$_3$INO$_4$ 476.8798, found 476.87.98. Anal calcd for C$_{13}$H$_{11}$Cl$_3$INO$_4$: C, 32.63; H, 2.32; N, 2.93. Found: C, 32.65; H, 2.37; N, 2.90.

2,5,6-Trichloro-3-(2-furyl)-1-(2-deoxy-β-D-ribofuranosyl)indole (4.78)

2,5,6-Trichloro-3-(2-furyl)-1-(3,5-di-O-toluoyl-2-deoxy-β-D-ribofuranosyl)indole (4.76, 142 mg, 0.22 mmol) was suspended in dry MeOH (10 mL) to which was added sodium methoxide (30 mg, 0.56 mmol). The suspension was stirred at room temperature for 45 min, until the solids were completely dissolved. The solvent was then removed under vacuum, and the residue suspended in brine (50 mL). The aqueous suspension was extracted with EtOAc (2×50 mL), and the combined organic extracts were dried over MgSO$_4$, filtered and evaporated to yield a clear oil. The oil was dissolved in CHCl$_3$ (1 mL) and subjected to column chromatography (40×350 mm) on silica gel with 10% MeOH/CHCl$_3$. Fractions containing product were pooled and evaporated to yield a pale yellow solid which was recrystallized from 10% MeOH/CHCl$_3$ and hexane to yield 67 mg (75%) of 4.78 as a white crystalline solid: mp 140-141 C; R$_f$ 0.5 (10% MeOH/CHCl$_3$); $^1$H-NMR (500 MHz, DMSO-d$_6$): δ 8.46 (s, 1H), 8.14 (s, 1H), 7.86 (s, 1H), 6.88 (d, 1H), 6.68 (s, 1H), 6.47 (dd, 1H), 5.42 (d, 1H, D$_2$O exch.), 5.23 (s, 1H, D$_2$O exch.), 4.45 (d, 1H), 3.89 (d, 1H), 3.73 (s, 2H), 2.55 (m, 1H), 2.13 (m, 1H). $^{13}$C-NMR (125 MHz, DMSO-d$_6$): δ 146.54, 142.25, 132.30, 125.61, 124.39, 124.09, 122.64, 120.75, 114.98, 111.51, 106.91, 104.87, 87.25, 85.04, 69.98, 60.91, 38.97. HRMS (EI) m/z calcd. for C$_{17}$H$_{14}$Cl$_3$NO$_4$ 400.9988, found 400.9986. Anal calcd for C$_{17}$H$_{14}$Cl$_3$NO$_4$·¼H$_2$O: C, 50.15; H, 3.59; N, 3.44. Found: C, 50.17; H, 3.65; N, 3.43.

2,5,6-Trichloro-3-(3-thienyl)-1-(2-deoxy-β-D-ribofuranosyl)indole (4.79)

2,5,6-Trichloro-3-(2-thienyl)-1-(3,5-di-O-toluoyl-2-deoxy-β-D-ribofuranosyl)indole (4.77, 159 mg, 0.24 mmol) was suspended in dry MeOH (12 mL) to which was added sodium methoxide (30 mg, 0.56 mmol). The suspension was stirred at room temperature for 90 min, until the solids were completely dissolved. The solvent was then removed under vacuum, and the residue suspended in brine (50 mL). The aqueous suspension was extracted with EtOAc (2×50 mL), and the combined organic extracts were dried over MgSO$_4$, filtered and evaporated to yield a clear oil. The oil was dissolved in CHCl$_3$ (1 mL) and subjected to column chromatography (40×350 mm) on silica gel with 10% MeOH/CHCl$_3$. Fractions containing product were pooled and evaporated to yield a pale yellow solid which was recrystallized from 10% MeOH/CHCl$_3$ and hexane to yield 84 mg (82%) of 4.79 as a white crystalline solid: mp 144-145° C.; R$_f$ 0.5 (10% MeOH/CHCl$_3$); $^1$H-NMR (500 MHz, DMSO-d$_6$): δ 8.44 (s, 1H), 7.82 (d, 1H), 7.80 (s, 1H), 7.74 (dd, 1H), 7.47 (d, 1H), 6.48 (dd, 1H), 5.41 (d, 1H, D$_2$O exch.), 5.21 (s, 1H, D$_2$O exch.), 4.45 (d, 1H), 3.88 (d, 1H), 3.70 (s, 2H), 2.57 (m, 1H), 2.12 (m, 1H). $^{13}$C-NMR (125 MHz, DMSO-d$_6$): δ 132.30, 130.79, 127.68, 126.69, 125.99, 125.21, 124.16, 123.72, 123.42, 119.78, 114.84, 109.19, 87.17, 85.05, 70.04, 60.99, 38.95. HRMS (EI) m/z calcd. for C$_{17}$H$_{14}$Cl$_3$NO$_3$S 416.9760, found 416.9760. Anal calcd for C$_{17}$H$_{14}$Cl$_3$NO$_3$S·¼H$_2$O: C, 48.24; H, 3.45; N, 3.31. Found: C, 48.17; H, 3.49; N, 3.32.

2,5,6-Trichloro-3-(2-furyl)-1-(β-D-ribofuranosyl)indole (4.84)

2,5,6-Trichloro-3-(2-furyl)-1-(2,3-O-isopropylidene-5-O-methoxymethyl-β-D-ribofuranosyl)indole (4.82, 105 mg, 0.21 mmol) was dissolved in absolute MeOH (10 mL) to which was added concentrated aqueous HCl (2 mL). The resulting suspension was heated on a 60 □C oil bath for 45 min, then cooled to room temperature and evaporated until no more MeOH remained. The remaining aqueous suspension was diluted with brine (25 mL) and extracted with EtOAc (2×40 mL). The combined organic extracts were washed with 10% NaHCO$_3$ (25 mL), dried over MgSO$_4$, filtered and evaporated to yield a dark oil. The oil was dissolved in 10% MeOH/CHCl$_3$ (1 mL) and subjected to column chromatography (40×350 mm) on silica gel with 10% MeOH/CHCl$_3$. Fractions containing product were pooled and evaporated to yield 63 mg (65%) of 4.84 as a pale grey powder: mp 139-140 C; R$_f$ 0.3 (10% MeOH/CHCl$_3$); $^1$H-NMR (500 MHz, DMSO-d$_6$): δ 8.55 (s, 1H), 8.16 (s, 1H), 7.87 (s, 1H), 6.90 (d, 1H), 6.68 (d, 1H), 5.99 (d, 1H), 5.40 (d, 1H, D$_2$O exch.), 5.37 (t, 1H, D$_2$O exch.), 5.25 (d, 1H, D$_2$O exch.), 4.46 (q, 1H), 4.16 (m, 1H), 3.99 (d, 1H), 3.73 (m, 2H). $^{13}$C-NMR (125 MHz, DMSO-d$_6$): δ 146.58, 142.26, 132.48, 125.62, 124.45, 124.20, 123.71, 120.72, 115.20, 111.52, 106.90, 104.86, 88.76, 85.93, 71.32, 69.64, 61.11. HRMS (EI) m/z calcd. for C$_{17}$H$_{14}$Cl$_3$NO$_5$ 416.9938, found 416.9943. Anal calcd for C$_{17}$H$_{14}$Cl$_3$NO$_5$: C, 48.77; H, 3.37; N, 3.35. Found: C, 48.96; H, 3.46; N, 3.24.

2,5,6-Trichloro-3-(3-thienyl)-1-(β-D-ribofuranosyl)indole (4.85)

2,5,6-Trichloro-3-(3-thienyl)-1-(2,3-O-isopropylidene-5-O-methoxymethyl-β-D-ribofuranosyl)indole (4.83, 175 mg, 0.34 mmol) was dissolved in absolute MeOH (10 mL) to which was added concentrated aqueous HCl (2 mL). The resulting suspension was heated on a 60 □C oil bath for 45 min, then cooled to room temperature and evaporated until no more MeOH remained. The remaining aqueous suspension was diluted with brine (25 mL) and extracted with EtOAc (2×40 mL). The combined organic extracts were washed with 10% NaHCO$_3$ (25 mL), dried over MgSO$_4$, filtered and evaporated to yield an orange oil. The oil was dissolved in 10% MeOH/CHCl$_3$ (1 mL) and subjected to column chromatography (40×350 mm) on silica gel with 10% MeOH/CHCl$_3$. Fractions containing product were pooled and evaporated to yield a pale yellow residue which was recrystallized form MeOH/H$_2$O to yield 110 mg (75%) of 4.85 as a tan solid: mp 152-153° C.; R$_f$ 0.4(10% MeOH/CHCl$_3$); $^1$H-NMR (500 MHz, DMSO-d$_6$): δ 8.52 (s, 1H), 7.83 (dd, 1H), 7.82 (s, 1H), 7.74 (dd, 1H), 7.48 (dd, 1H), 6.00 (d, 1H), 5.38 (d, 1H, D$_2$O exch.), 5.35 (t, 1H, D$_2$O exch.), 5.23 (d, 1H, D$_2$O exch.), 4.48 (q, 1H), 4.16 (m, 1H), 3.99 (d, 1H), 3.73 (m, 2H). $^{13}$C-NMR (125 MHz, DMSO-d$_6$): δ 132.50, 130.86, 127.66, 126.69, 126.08, 125.22, 124.46, 124.21, 123.69, 119.75, 115.04, 109.15, 88.83, 85.78, 71.24, 69.66, 61.16. HRMS (EI) m/z calcd. for C$_{17}$H$_{14}$Cl$_3$NO$_4$S 432.9709, found 432.9713. Anal calcd for C$_{17}$H$_{14}$Cl$_3$NO$_4$S: C, 46.97; H, 3.25; N, 3.22. Found: C, 46.95; H, 3.40; N, 3.14.

2,5,6-Trichloro-3-formylmethyl-1-(β-D-ribofuranosyl)indole (4.92)

2,5,6-Trichloro-3-[1-(2-methoxy)vinyl]-1-(2,3-O-isopropylidene-5-O-acetyl-β-D-ribofuranosyl)indole (4.90, 185 mg, 0.38 mmol) was dissolved in absolute MeOH (10 mL) to which was added concentrated aqueous HCl (2 mL). The resulting suspension was heated on a 60° C. oil bath for 1 h, then cooled to room temperature and evaporated until no more MeOH remained. The remaining aqueous suspension was diluted with brine (25 mL) and extracted with EtOAc (2×40 mL). The combined organic extracts were washed with 10% NaHCO$_3$ (25 mL), dried over MgSO$_4$, filtered and evaporated to yield a yellow oil. The oil was dissolved in 90% aqueous trifluoroacetic acid (10 mL) and the solution was stirred at room temperature for 5 min. The solvent was evaporated until approx 1 mL remained, and the remainder was poured into 10% aqueous NaHCO$_3$ (50 mL). The aqueous suspension was extracted with EtOAc (2×50 mL), and the combined organic extracts were dried over MgSO$_4$, filtered and evaporated to yield a white powder. The solid was dissolved in MeOH (1 mL) and subjected to column chromatography (40×350 mm) on C18-revers phase silica gel with 75% MeOH/H$_2$O. Fractions containing product were pooled and evaporated to yield 93 mg (62%) of 4.92 as a tan powder: mp 119-121 C; R$_f$ 0.2 (10% MeOH/CHCl$_3$); $^1$H-NMR (500 MHz, DMSO-d$_6$): δ 9.67 (s, 1H), 8.41 (s, 1H), 7.84 (s, 1H), 5.89 (d, 1H), 5.34 (d, 1H, D$_2$O exch.), 5.31 (t, 1H, D$_2$O exch.), 5.22 (d, 1H, D$_2$O exch.), 4.44 (q, 1H), 4.13 (m, 1H), 3.98-3.89 (m, 3H), 3.69 (m, 2H). $^{13}$C-NMR (125 MHz, DMSO-d$_6$): δ 198.66, 132.52, 127.44, 126.40, 124.83, 123.53, 119.88, 114.76, 104.60, 88.78, 85.64, 71.21, 69.66, 61.19, 38.34. HRMS (EI) m/z calcd. for C$_{17}$H$_{20}$Cl$_3$NO$_6$ 392.9938, found 392.9950. Anal calcd for C$_{17}$H$_{20}$Cl$_3$NO$_6$: C, 45.65; H, 3.58; N, 3.55. Found: C, 45.48; H, 3.91; N, 3.48.

2,5,6-Trichloro-3-formyl-1-(5-deoxy-β-D-ribofuranosyl)indole (4.97)

2,5,6-Trichloro-3-formyl-1-(2,3-O-isopropylidene-5-deoxy-β-D-ribofuranosyl)indole (4.95, 139 mg, 0.34 mmol) was dissolved in 90% aqueous trifluoroacetic acid (5 mL). The solution was stirred at room temperature for 5 min and then evaporated to approx 1 mL. The remainder was poured into 5% aqueous Na$_2$CO$_3$ (10 mL) and brine (40 mL). The aqueous suspension was extracted with EtOAc (2×100 mL), and the combined organic extracts were dried over MgSO$_4$, filtered and evaporated to yield a pale yellow solid. The solid was dissolved in DMF (0.5 mL) and subjected to column chromatography (40×350 mm) on silica gel with 10% MeOH/CHCl$_3$. Fractions containing product were pooled and evaporated to yield a white solid which was recrystallized from boiling hexane to yield 86 mg (70%) of 4.97 as a white crystalline solid: mp 217-218 C; R$_f$ 0.6 (10% MeOH/CHCl$_3$); $^1$H-NMR (500 MHz, DMSO-d$_6$): δ 10.03 (s, 1H), 8.27 (s, 1H), 7.94 (s, 1H), 6.00 (d, 1H), 5.53 (d, 1H, $D_2O$ exch.), 5.31 (d, 1H, $D_2O$ exch.), 4.50 (q, 1H), 4.03 (m, 1H), 3.92 (q, 1H), 1.45 (d, 3H). $^{13}$C-NMR (125 MHz, DMSO-$d_6$): δ 184.11, 137.58, 133.06, 126.69, 126.60, 124.07, 121.01, 114.23, 112.55, 89.88, 81.01, 73.68, 71.82, 18.86. HRMS (EI) m/z calcd. for $C_{14}H_{12}Cl_3NO_4$ 362.9832, found 362.9836. Anal calcd for $C_{14}H_{12}Cl_3NO_4$: C, 46.12; H, 3.32; N, 3.84. Found: C, 46.07; H, 3.44; N, 3.79.

2,5,6-Trichloro-3-cyano-1-(5-deoxy-β-D-ribofuranosyl)indole (4.98)

2,5,6-Trichloro-3-cyano-1-(2,3-O-isopropylidene-5-deoxy-β-D-ribofuranosyl)indole (4.96, 207 mg, 0.52 mmol) was dissolved in 90% aqueous trifluoroacetic acid (5 mL). The solution was stirred at room temperature for 5 min, then evaporated to approx 1 mL. The remainder was poured into 5% aqueous $Na_2CO_3$ (10 mL) and brine (40 mL). The aqueous suspension was extracted with EtOAc (2×100 mL), and the combined organic extracts were dried over $MgSO_4$, filtered and evaporated to yield a pale yellow solid. The solid was dissolved in DMF (0.5 mL) and subjected to column chromatography (40×350 mm) on silica gel with 10% MeOH/$CHCl_3$. Fractions containing product were pooled and evaporated to yield a white solid which was recrystallized from 10% MeOH/$CHCl_3$ and hexane to yield 152 mg (82%) of 4.98 as a white crystalline solid: mp 227-228° C.; $R_f$ 0.6 (10% MeOH/$CHCl_3$); $^1$H-NMR (500 MHz, DMSO-$d_6$): δ 8.00 (s, 1H), 7.96 (s, 1H), 5.96 (d, 1H), 5.54 (d, 1H, $D_2O$ exch.), 5.31 (d, 1H, $D_2O$ exch.), 4.46 (q, 1H), 4.02 (m, 1H), 3.91 (q, 1H), 1.44 (d, 3H). $^{13}$C-NMR (125 MHz, DMSO-$d_6$): δ 135.31, 132.36, 127.17, 126.49, 125.32, 119.86, 114.54, 112.70, 90.46, 86.63, 81.09, 73.62, 71.94, 18.82. HRMS (EI) m/z calcd. for $C_{14}H_{11}Cl_3N_2O_3$ 359.9835, found 359.9836. Anal calcd for $C_{14}H_{11}Cl_3N_2O_3 \cdot \frac{1}{8}H_2O$ C, 46.04; H, 3.15; N, 7.67. Found: C, 45.90; H, 3.15; N, 7.66.

2,5,6-Trichloro-3-formyl-1-(5-deoxy-5-azido-β-D-ribofuranosyl)indole (4.102)

2,5,6-Trichloro-3-formyl-1-(2,3-O-isopropylidene-5-deoxy-5-azido-β-D-ribofuranosyl)indole (4.100, 168 mg, 0.38 mmol) was dissolved in 90% aqueous trifluoroacetic acid (10 mL). The resulting solution was stirred at room temperature for 2 min, then evaporated to approx 1 mL. The remainder was poured into 10% aqueous $NaHCO_3$ (50 mL). The aqueous suspension was extracted with EtOAc (2×50 mL), and the combined organic extracts were dried over $MgSO_4$, filtered and evaporated to yield a white solid. The solid was dissolved in 10% MeOH/$CHCl_3$ (1 mL) and subjected to column chromatography (40×350 mm) on silica gel with 10% MeOH/$CHCl_3$. Fractions containing product were pooled and evaporated to yield a pale yellow solid which was recrystallized from boiling $CHCl_3$ to yield 117 mg (76%) of 4.102 as a pale yellow crystalline solid: mp 160-161° C.; $R_f$ 0.5 (10% MeOH/$CHCl_3$); $^1$H-NMR (500 MHz, DMSO-$d_6$): δ 10.04 (s, 1H), 8.28 (s, 1H), 8.20 (s, 1H), 6.03 (d, 1H), 5.63 (d, 1H, $D_2O$ exch.), 5.47 (d, 1H, $D_2O$ exch.), 4.48 (q, 1H), 4.13 (q, 1H), 4.09 (q, 1H), 3.87 (d, 2H). $^{13}$C-NMR (125 MHz, DMSO-$d_6$): δ 184.18, 137.72, 132.86, 126.71, 126.69, 124.15, 121.03, 114.87, 112.60, 89.30, 83.30, 71.37, 69.53, 51.56. HRMS (EI) m/z calcd. for $C_{14}H_{11}Cl_3N_4O_4$ 403.9846, found 403.9833. Anal calcd for $C_{14}H_{11}Cl_3N_4O_4 \cdot \frac{1}{20}CHCl_3$: C, 41.00; H, 2.71; N, 13.61. Found: C, 40.90; H, 2.69; N, 13.64.

2,5,6-Trichloro-3-cyano-1-(5-deoxy-5-azido-β-D-ribofuranosyl)indole (4.103)

2,5,6-Trichloro-3-cyano-1-(2,3-O-isopropylidene-5-deoxy-5-azido-β-D-ribofuranosyl)indole (4.101, 216 mg, 0.49 mmol) was dissolved in 90% aqueous trifluoroacetic acid (10 mL). The resulting solution was stirred at room temperature for 2 min, then evaporated to approx 1 mL. The remainder was poured into 10% aqueous $NaHCO_3$ (50 mL). The aqueous suspension was extracted with EtOAc (2×50 mL), and the combined organic extracts were dried over $MgSO_4$, filtered and evaporated to yield a white solid which was recrystallized from boiling $CHCl_3$ to yield 165 mg (84%) of 4.103 as a white powder: mp 161-162 C; $R_f$ 0.5 (10% MeOH/$CHCl_3$); $^1$H-NMR (500 MHz, DMSO-$d_6$): δ 8.24 (s, 1H), 7.98 (s, 1H), 5.97 (d, 1H), 5.63 (d, 1H, $D_2O$ exch.), 5.47 (d, 1H, $D_2O$ exch.), 4.45 (q, 1H), 4.11-4.07 (m, 2H), 3.86 (d, 2H). $^{13}$C-NMR (125 MHz, DMSO-$d_6$): δ 135.53, 132.15, 127.21, 126.62, 125.39, 119.93, 115.18, 112.66, 89.93, 86.69, 83.37, 71.48, 69.51, 51.52. HRMS (EI) m/z calcd. for $C_{14}H_{10}Cl_3N_5O_3$ 400.9849, found 400.9834. Anal calcd for $C_{14}H_{10}Cl_3N_5O_3 \cdot \frac{1}{20}CHCl_3$: C, 41.30; H, 2.48; N, 17.14. Found: C, 41.15; H, 2.53; N, 16.93.

2,5,6-Trichloro-3-formyl-1-(5-deoxy-5-fluoro-β-D-ribofuranosyl)indole (4.107)

2,5,6-Trichloro-3-formyl-1-(2,3-O-isopropylidene-5-deoxy-5-fluoro-β-D-ribofuranosyl)indole (4.105, 133 mg, 0.31 mmol) was dissolved in 90% aqueous trifluoroacetic acid (5 mL). The solution was stirred at room temperature for 5 min, then evaporated to approx 1 mL. The remainder was poured into 10% aqueous $NaHCO_3$ (50 mL). The aqueous suspension was extracted with EtOAc (2×50 mL), and the combined organic extracts were dried over $MgSO_4$, filtered and evaporated to yield a pale yellow solid. The solid was dissolved in DMF (0.5 mL) and subjected to column chromatography (40×350 mm) on silica gel with 10% MeOH/$CHCl_3$. Fractions containing product were pooled and evaporated to yield a white solid which was recrystallized from 10% MeOH/$CHCl_3$ and hexane to yield 82 mg (68%) of 4.107 as a white crystalline solid: mp 207-208° C.; $R_f$ 0.5 (10% MeOH/$CHCl_3$); $^1$H-NMR (500 MHz, DMSO-$d_6$): δ 10.05 (s, 1H), 8.28 (s, 1H), 8.02 (s, 1H), 6.08 (d, 1H), 5.67 (d, 1H, $D_2O$ exch.), 5.55 (d, 1H, $D_2O$ exch.), 4.83 (dq, 1H), 4.75 (dq, 1H), 4.40 (q, 1H), 4.23 (m, 1H), 4.20 (dd, 1H). $^{13}$C-NMR (125 MHz, DMSO-$d_6$): δ 184.87, 138.51, 133.49, 127.43, 127.35, 124.93, 121.74, 115.27, 113.21, 89.80, 84.43, 83.84, 72.29, 69.32. $^{19}$F-NMR (300 MHz, DMSO-$d_6$) −228.57. HRMS (EI) m/z calcd. for $C_{14}H_{11}Cl_3FNO_4$ 380.9738, found 380.9734. Anal calcd for $C_{14}H_{11}Cl_3FNO_4$: C, 43.95; H, 2.90; N, 3.66. Found: C, 43.90; H, 2.98; N, 3.55.

2,5,6-Trichloro-3-cyano-1-(5-deoxy-5-fluoro-β-D-ribofuranosyl)indole (4.108)

2,5,6-Trichloro-3-cyano-1-(2,3-O-isopropylidene-5-deoxy-5-fluoro-β-D-ribofuranosyl)indole (4.106, 133 mg, 0.31 mmol) was dissolved in 90% aqueous trifluoroacetic acid (5 mL). The solution was stirred at room temperature for 5 min, then evaporated to approx 1 mL. The remainder was poured into 10% aqueous $NaHCO_3$ (50 mL). The aqueous suspension was extracted with EtOAc (2×50 mL), and the combined organic extracts were dried over $MgSO_4$, filtered and evaporated to yield a white solid which was recrystallized from EtOAc/hexane to yield 150 mg (88%) of 4.108 as a white crystalline solid: mp 246-247 □C; $R_f$ 0.6 (10% MeOH/

CHCl$_3$); $^1$H-NMR (500 MHz, DMSO-d$_6$): δ 8.04 (s, 1H), 7.99 (s, 1H), 6.01 (d, 1H), 5.66 (d, 1H, D$_2$O exch.), 5.55 (d, 1H, D$_2$O exch.), 4.84 (m, 1H), 4.74 (m, 1H), 4.36 (q, 1H), 4.22-4.16 (m, 1H). $^{13}$C-NMR (125 MHz, DMSO-d$_6$): δ 135.67, 132.07, 127.25, 126.62, 125.52, 120.00, 114.91, 112.68, 89.83, 86.60, 83.96, 83.11, 71.75, 68.59. $^{19}$F-NMR (300 MHz, DMSO-d$_6$) −228.54. HRMS (EI) m/z calcd. for C$_{14}$H$_{10}$Cl$_3$FN$_2$O$_3$ 377.9741, found 377.9751. Anal calcd for C$_{14}$H$_{10}$Cl$_3$FN$_2$O$_3$: C, 44.30; H, 2.66; N, 7.38. Found: C, 44.46; H, 2.76; N, 7.14.

5,6-Dichloro-2-methoxy-3-formyl-1-(2-deoxy-β-D-ribofuranosyl)indole (4.114)

3-Formyl-2,5,6-trichloro-1-[3,5-di-O-(p-toluoyl)-2-deoxy-β-D-ribofuranosyl]indole (4.113, 198 mg, 0.33 mmol) was suspended in dry MeOH (10 mL) to which was added sodium methoxide (75 mg, 1.4 mmol). The suspension was stirred at room temperature for 16 h, after which time the solution clarified. The solvent was then removed under vacuum, and the residue was suspended in water (50 mL), and extracted with EtOAc (2×100 mL). The combined organic extracts were washed with brine (25 mL), dried over MgSO$_4$, filtered and evaporated to yield a damp solid. The crude material was dissolved in MeOH (1 mL) and subjected to column chromatography (40×350 mm) on silica gel with 10% MeOH/CHCl$_3$. Fractions containing product were pooled and evaporated to yield a white solid. The solid was recrystallized from warm MeOH to yield 82 mg (68%) of 4.114 as a white crystalline solid: mp 186-187° C.; R$_f$ 0.3 (10% MeOH/CHCl$_3$); $^1$H-NMR (500 MHz, DMSO-d$_6$): δ 10.21 (s, 1H), 8.29 (s, 1H), 8.22 (s, 1H), 6.32 (dd, 1H), 5.37 (b, 1H, D$_2$O exch.), 5.15 (b, 1H, D$_2$O exch.), 4.43 (s, 3H), 4.41 (m, 1H), 3.83 (d, 1H), 3.68 (m, 2H), 2.53 (m, 1H), 2.11 (m, 1H). $^{13}$C-NMR (125 MHz, DMSO-d$_6$): δ 183.22, 159.16, 129.40, 125.04, 124.73, 124.66, 121.11, 114.24, 100.02, 87.29, 82.99, 70.07, 64.16, 61.03, 38.43. HRMS (EI) m/z calcd. for C$_{15}$H$_{15}$Cl$_2$NO$_5$ 359.0327, found 359.0320. Anal calcd for C$_{15}$H$_{15}$Cl$_2$NO$_5$·½H$_2$O: C, 48.80; H, 4.37; N, 3.79. Found: C, 48.48; H, 4.61; N, 3.61.

2,5,6-Trichloro-3-acetyl-1-(2-deoxy-β-D-ribofuranosyl)indole (4.117)

2,5,6-Trichloro-3-acetyl-1-[3,5-di-O-(p-toluoyl)-2-deoxy-β-D-ribofuranosyl]indole (4.116, 0.62 g, 1.0 mmol) was suspended in dry MeOH (50 mL) to which was added sodium methoxide (220 mg, 4.1 mmol). The suspension was stirred at room temperature for 16 h, after which time the solution first clarified and a precipitate then formed. The suspension was allowed to stand at 4° C. for 4 h, and was then filtered, and the solids rinsed with cold MeOH (10 mL). The solid was recrystallized from warm MeOH to yield 0.28 g (74%) of 4.117 as a white crystalline solid: mp dec. >200 C; R$_f$ 0.4 (10% MeOH/CHCl$_3$); $^1$H-NMR (500 MHz, DMSO-d$_6$): δ 8.52 (s, 1H), 8.37 (s, 1H), 6.49 (dd, 1H), 5.43 (s, 1H, D$_2$O exch.), 5.26 (s, 1H, D$_2$O exch.), 4.45 (m, 1H), 3.89 (d, 1H), 3.72 (m, 2H), 2.60 (s, 3H), 2.49 (m, 1H), 2.13 (m, 1H). $^{13}$C-NMR (125 MHz, DMSO-d$_6$): δ 192.13, 132.15, 131.99, 126.12, 125.50, 125.65, 121.96, 115.25, 112.85, 87.55, 85.43, 69.81, 60.67, 47.10, 30.68. HRMS (EI) m/z calcd. for C$_{15}$H$_{14}$Cl$_3$NO$_4$ 376.9988, found 376.9982. Anal calcd for C$_{15}$H$_{14}$Cl$_3$NO$_4$: C, 47.58; H, 3.73; N, 3.70. Found: C, 47.52; H, 3.95; N, 3.59.

2,5,6-Trichloro-3-cyano-1-(2-deoxy-β-D-ribofuranosyl)indole (4.119) and 5,6-dichloro-2-methoxy-3-cyano-1-(2-deoxy-β-D-ribofuranosyl)indole (4.120)

2,5,6-Trichloro-3-cyano-1-[3,5-di-O-(p-toluoyl)-2-deoxy-β-D-ribofuranosyl]indole (4.118, 366 mg, 0.63 mmol) was suspended in dry MeOH (30 mL) to which was added sodium methoxide (82 mg, 1.5 mmol). The suspension was stirred at room temperature for 16 h, then the solvent was removed under vacuum, and the residue was suspended in brine (100 mL) and water (10 mL). The aqueous mixture was extracted with EtOAc (2×100 mL), and the combined organic extracts were dried over MgSO$_4$, filtered and evaporated to yield a viscous residue. The residue was dissolved in DMF (0.5 mL) and subjected to column chromatography (40×350 mm) on silica gel with 10% MeOH/CHCL$_3$. Fractions containing product were pooled and evaporated to yield a white solid. The solid was dissolved in DMF (0.5 mL) and subjected to column chromatography (40×350 mm) on C18-reverse phase silica gel with 75% MeOH/H$_2$O. Fractions containing the more rapidly eluting material were pooled and evaporated to yield 47 mg (21%) of 4.120 as a white powder. Fractions containing the more slowly eluting material were pooled and evaporated to yield 120 mg (53%) of 4.119 as a white powder. 4.120: mp 222-223° C.; R$_f$ 0.4 (10% MeOH/CHCl$_3$); $^1$H-NMR (500 MHz, DMSO-d$_6$): δ 8.27 (s, 1H), 7.62 (s, 1H), 6.26 (dd, 1H), 5.54 (d, 1H, D$_2$O exch.) 5.12 (t, 1H, D$_2$O exch.), 4.38 (s, 4H), 3.81 (m, 1H), 3.67 (m, 2H), 2.50 (m, 1H), 2.07 (m, 1H). $^{13}$C-NMR (125 MHz, DMSO-d$_6$): δ 157.80, 128.43, 126.08, 124.90, 124.71, 118.18, 114.76, 114.67, 87.35, 83.09, 70.04, 64.86, 61.02, 60.62, 38.35. HRMS (electrospray) m/z calcd. for C$_{15}$H$_{14}$Cl$_2$N$_2$O$_4$·Na 379.0228, found 379.0246. Anal calcd for C$_{15}$H$_{14}$Cl$_2$N$_2$O$_4$·⅛H$_2$O: C, 49.93; H, 4.02; N, 7.76. Found: C, 50.29; H, 4.04; N, 7.76. 4.119: mp 187-188° C.; R$_f$ 0.4 (10% MeOH/CHCl$_3$); $^1$H-NMR (500 MHz, DMSO-d$_6$): δ 8.62 (s, 1H), 7.94 (s, 1H), 6.42 (dd, 1H), 5.45 (d, 1H, D$_2$O exch.), 5.28 (t, 1H, D$_2$O exch.), 4.45 (d, 1H), 3.90 (d, 1H), 3.72 (m, 2H), 2.50 (m, 1H), 2.19 (m, 1H). $^{13}$C-NMR (125 MHz, DMSO-d$_6$): δ 134.68, 131.90, 127.11, 126.41, 125.45, 119.62, 116.11, 112.82, 87.74, 85.98, 85.95, 69.77, 60.69. HRMS (ES) m/z calcd. for C$_{14}$H$_{11}$Cl$_3$N$_2$O$_3$·Na 382.9733, found 382.9747. Anal calcd for C$_{14}$H$_{11}$Cl$_3$N$_2$O$_3$·⅛H$_2$O: C, 46.04; H, 3.15; N, 7.67. Found: C, 46.22; H, 3.18; N, 7.67.

2,5,6-Trichloro-3-formyl-1-(5-O-acetyl-β-D-ribofuranosyl)indole (4.122)

2,5,6-Trichloro-3-formyl-1-(2,3-O-isopropylidene-5-O-acetyl-β-D-ribofuranosyl)indole (4.121, 540 mg, 1.2 mmol) was dissolved in 90% aqueous trifluoroacetic acid (10 mL) and was stirred at room temperature for 5 min. The solvent was then removed under vacuum and the residue dissolved in EtOAc (100 mL). The organic solution was washed with 10% aqueous NaHCO$_3$ (50 mL), then dried over MgSO$_4$, filtered and evaporated to yield a white powder which was recrystallized from EtOAc/hexane to yield 420 mg (86%) of 4.122 as a white crystalline solid: mp 154-155° C.; R$_f$ 0.5 (10% MeOH/CHCl$_3$); $^1$H-NMR (500 MHz, DMSO-d$_6$): δ 10.04 (s, 1H), 8.31 (s, 1H), 8.00 (s, 1H), 6.04 (d, 1H), 5.60 (d, 1H D$_2$O exch.), 5.49 (d, 1H, D$_2$O exch.), 4.48 (dd, 1H), .4.43 (s, 1H), 4.28 (dd, 1H), 4.17 (dq, 2H), 2.16 (s, 3H). $^{13}$C-NMR (125 MHz, DMSO-d$_6$): δ 184.13, 170.25, 137.73, 132.84, 126.71, 126.70, 124.21, 121.07, 114.52, 112.52, 89.14, 82.82, 71.63, 68.92, 63.45, 20.83. HRMS (ES) m/z calcd. for $C_{16}H_{14}Cl_3NO_6$·Na 433.9784, found 433.9795. Anal calcd for $C_{16}H_{14}Cl_3NO_6$·¼EtOAc: C, 45.92; H, 3.63; N, 3.15. Found: C, 46.19; H, 3.68; N, 3.18.

2,5,6-Trichloro-3-cyano-1-(5-O-acetyl-β-D-ribofuranosyl)indole (4.124)

2,5,6-Trichloro-3-cyano-1-(2,3-O-isopropylidene-5-O-acetyl-β-D-ribofuranosyl)indole (4.123, 2.45 g, 5.3 mmol) was dissolved in 90% aqueous trifluoroacetic acid (25 mL) and the solution was stirred at room temperature for 2 min. The solvent was then removed under vacuum and the residue dissolved in EtOAc (100 mL). The organic solution was washed with 10% aqueous $NaHCO_3$ (100 mL), then dried over $MgSO_4$, filtered and evaporated to yield a pale yellow solid. The solid was dissolved in DMF (1 mL) and subjected to column chromatography (50×450 mm) on silica gel with 7.5% $MeOH/CHCl_3$. Fractions containing product were pooled and evaporated to yield a white solid which was recrystallized from $CHCl_3$/hexane to yield 1.85 g (83%) of 4.124 as a white crystalline solid: mp 103-104° C.; $R_f$ 0.6 (10% $MeOH/CHCl_3$); $^1H$-NMR (500 MHz, DMSO-$d_6$): δ 8.04 (s, 1H), 7.98 (s, 1H), 5.96 (d, 1H), 5.58 (d, 1H, $D_2O$ exch.), 5.47 (d, 1H, $D_2O$ exch.), 4.45 (dd, 1H), 4.38 (q, 1H), 4.25 (dd, 1H), 4.14 (dq, 2H), 2.13 (s, 3H). $^{13}C$-NMR (125 MHz, DMSO-$d_6$): δ 170.22, 135.57, 132.11, 127.19, 126.64, 125.49, 119.99, 114.86, 112.65, 89.80, 86.62, 82.87, 71.71, 68.90, 63.43, 20.80. HRMS (EI) m/z calcd. for $C_{16}H_{13}Cl_3N_2O_5$ 417.9890, found 417.9883. Anal calcd for $C_{16}H_{13}Cl_3N_2O_5$: C, 45.79; H, 3.12; N, 6.68. Found: C, 45.78; H, 3.08; N, 6.53.

2,5,6-Trichloro-3-formyl-1-(5-O-propionyl-β-D-ribofuranosyl)indole (4.128)

2,5,6-Trichloro-3-formyl-1-(2,3-O-isopropylidene-5-O-propionyl-β-D-ribofuranosyl)indole (4.125, 169 mg, 0.35 mmol) was dissolved in 90% aqueous trifluoroacetic acid (10 mL) and was stirred at room temperature for 2 min. The solvent was then removed under vacuum and the residue dissolved in EtOAc (100 mL). The organic solution was washed with 10% aqueous $NaHCO_3$ (50 mL), then dried over $MgSO_4$, filtered and evaporated to yield a pale yellow solid. The solid was dissolved in 10% $MeOH/CHCl_3$ (1 mL) and subjected to column chromatography (40×350 mm) on silica gel with 10% $MeOH/CHCl_3$. Fractions containing product were pooled and evaporated to yield a pale yellow solid which was recrystallized from boiling EtOAc/hexane to yield 112 mg (72%) of 4.128 as a pale yellow crystalline solid: mp 139-140° C.; $R_f$ 0.6 (10% $MeOH/CHCl_3$); $^1H$-NMR (500 MHz, DMSO-$d_6$): δ 10.04 (s, 1H), 8.28 (s, 1H), 8.01 (s, 1H), 6.04 (d, 1H), 5.60 (d, 1H, $D_2O$ exch.), 5.48 (d, 1H, $D_2O$ exch.), 4.48 (dd, 1H), 4.42 (q, 1H), 4.29 (dd, 1H), 4.20 (q, 1H), 4.14 (m, 1H), 2.44 (q, 2H), 1.08 (t, 3H). $^{13}C$-NMR (125 MHz, DMSO-$d_6$): δ 184.20, 173.53, 137.77, 132.86, 126.71, 126.69, 124.25, 121.08, 114.50, 112.53, 89.11, 82.86, 71.66, 68.95, 63.43, 26.84, 8.94. HRMS (EI) m/z calcd. for $C_{17}H_{16}Cl_3NO_6$ 435.0043, found 435.0042. Anal calcd for $C_{17}H_{16}Cl_3NO_6$: C, 46.76; H, 3.69; N, 3.21. Found: C, 46.91; H, 3.76; N, 3.14.

2,5,6-Trichloro-3-formyl-1-(5-O-butyryl-β-D-ribofuranosyl)indole (4.129)

2,5,6-Trichloro-3-formyl-1-(2,3-O-isopropylidene-5-O-butyryl-β-D-ribofuranosyl)indole (4.126, 164 mg, 0.33 mmol) was dissolved in 90% aqueous trifluoroacetic acid (10 mL) and stirred at room temperature for 2 min. The solvent was then removed under vacuum and the residue dissolved in EtOAc (100 mL). The organic solution was washed with 10% aqueous $NaHCO_3$ (50 mL), then dried over $MgSO_4$, filtered and evaporated to yield a pale yellow solid. The solid was dissolved in 10% $MeOH/CHCl_3$ (1 mL) and subjected to column chromatography (40×350 mm) on silica gel with 10% $MeOH/CHCl_3$. Fractions containing product were pooled and evaporated to yield a pale yellow solid which was recrystallized from boiling EtOAc/hexane to yield 111 mg (74%) of 4.129 as a pale yellow crystalline solid: mp 128-129 C; $R_f$ 0.6 (10% $MeOH/CHCl_3$); $^1H$-NMR (500 MHz, DMSO-$d_6$): δ 10.04 (s, 1H), 8.29 (s, 1H), 8.01 (s, 1H), 6.04 (d, 1H), 5.61 (d, 1H, $D_2O$ exch.), 5.49 (d, 1H, $D_2O$ exch.), 4.51 (dd, 1H), 4.43 (q, 1H), 4.28 (dd, 1H), 4.20 (q, 1H), 4.12 (m, 1H), 2.44 (m, 2H), 1.59 (q, 2H), 0.90 (t, 3H). $^{13}C$-NMR (125 MHz, DMSO-$d_6$): δ 184.22, 172.68, 137.80, 132.86, 126.74, 126.70, 124.28, 121.11, 114.52, 112.55, 89.10, 82.86, 71.64, 68.98, 63.32. 17.92, 13.41. HRMS (EI) m/z calcd. for $C_{18}H_{18}Cl_3NO_6$ 449.0200, found 449.1096. Anal calcd for $C_{18}H_{18}Cl_3NO_6$: C, 47.97; H, 4.03; N, 3.11. Found: C, 48.21; H, 4.24; N, 3.10.

2,5,6-Trichloro-3-formyl-1-(5-O-methoxycarbonyl-β-D-ribofuranosyl)indole (4.130)

2,5,6-Trichloro-3-formyl-1-(2,3-O-isopropylidene-5-O-methoxycarbonyl-β-D-ribofuranosyl)indole (4.127, 191 mg, 0.40 mmol) was dissolved in 90% aqueous trifluoroacetic acid (10 mL) and was stirred at room temperature for 2 min. The solvent was then removed under vacuum and the residue dissolved in EtOAc (100 mL). The organic solution was washed with 10% aqueous $NaHCO_3$ (50 mL), then dried over $MgSO_4$, filtered and evaporated to yield a pale yellow solid. The solid was dissolved in 10% $MeOH/CHCl_3$ (1 mL) and subjected to column chromatography (40×350 mm) on silica gel with 10% $MeOH/CHCl_3$. Fractions containing product were pooled and evaporated to yield a pale yellow solid which was recrystallized from $MeOH/H_2O$ to yield 126 mg (72%) of 4.130 as a pale yellow crystalline solid: mp 148-149 C; $R_f$ 0.5 (10% $MeOH/CHCl_3$); $^1H$-NMR (500 MHz, DMSO-$d_6$): δ 10.04 (s, 1H), 8.27 (s, 1H), 8.00 (s, 1H), 6.05 (d, 1H), 5.63 (broad, 1H, $D_2O$ exch.), 5.51 (broad, 1H, $D_2O$ exch.), 4.49-4.41 (m, 3H), 4.21 (q, 1H), 4.17 (m, 1H), 3.76 (s, 3H). $^{13}C$-NMR (125 MHz, DMSO-$d_6$): δ 184.16, 154.94, 137.81, 132.88, 126.87, 126.77, 124.18, 121.02, 114.53, 112.55, 88.96, 82.60, 71.40, 69.02, 67.02, 54.87. HRMS (EI) m/z calcd. for $C_{16}H_{14}Cl_3NO_7$ 436.9836, found 436.9834. Anal calcd for $C_{16}H_{14}Cl_3NO_7$: C, 43.81; H, 3.22; N, 3.19. Found: C, 43.68; H, 3.39; N, 3.18.

5,6-Dichloro-2-bromo-3-formyl-1-(5-O-acetyl-β-D-ribofuranosyl)indole (4.136)

5,6-Dichloro-2-bromo-3-formyl-1-(2,3-O-isopropylidene-5-O-acetyl-β-D-ribofuranosyl)indole (4.135, 257 mg, 0.51 mmol) was dissolved in 90% aqueous trifluoroacetic acid (10 mL) and the solution was stirred at room temperature for 5 min. The solvent was evaporated until approx 1 mL remained, and the remainder was poured into 10% aqueous $NaHCO_3$ (50 mL). The aqueous suspension was extracted with EtOAc (2×50 mL), and the combined organic extracts were dried over $MgSO_4$, filtered and evaporated to yield a white powder. The solid was dissolved in DMF (0.5 mL) and subjected to column chromatography (40×350 mm) on silica gel with 10% $MeOH/CHCl_3$. Fractions containing product were pooled and evaporated to yield a white solid which was recrystallized from EtOAc and hexane to yield 220 mg (93%)

of 4.136 as a white crystalline solid: mp 159-160° C.; $R_f$ 0.5 (10% MeOH/CHCl$_3$); $^1$H-NMR (500 MHz, DMSO-d$_6$): δ 9.96 (s, 1H), 8.30 (s, 1H), 7.99 (s, 1H), 6.06 (d, 1H), 5.58 (d, 1H, D$_2$O exch.), 5.49 (d, 1H, D$_2$O exch.), 4.49 (dd, 1H), 4.43 (q, 1H), 4.27 (dd, 1H), 4.19 (q, 1H), 4.15 (m, 1H), 2.17 (s, 3H). $^{13}$C-NMR (125 MHz, DMSO-d$_6$): δ 185.55, 170.26, 134.00, 128.64, 126.60, 126.52, 125.35, 120.87, 114.87, 114.49, 90.45, 82.73, 71.50, 68.86, 63.41, 20.86. HRMS (EI) m/z calcd. for C$_{16}$H$_{14}$BrCl$_2$NO$_6$ 464.9381, found 464.9383. Anal calcd for C$_{16}$H$_{14}$BrCl$_2$NO$_6$: C, 43.01; H, 3.61; N, 2.87. Found: C, 43.31; H, 3.81; N, 2.85.

5,6-Dichloro-2-bromo-3-formyl-1-(β-D-ribofuranosyl)indole (4.137)

5,6-Dichloro-2-bromo-3-formyl-1-(5-O-acetyl-β-D-ribofuranosyl)indole (4.136, 101 mg, 0.22 mmol) was dissolved in dry MeOH (10 mL) to which was added sodium methoxide (25 mg, 0.46 mmol). The solution was stirred at room temperature for 15 min, until the starting material was consumed (TLC). Water (30 mL) was added and the solution evaporated until the MeOH was completely removed. The residual aqueous suspension was extracted with EtOAc (3×30 mL) and the combined organic extracts washed with brine (20 mL), dried over MgSO$_4$, filtered and evaporated to yield a white solid. The solid was dissolved in MeOH (1 mL) and subjected to column chromatography (40×350 mm) on C18-reverse phase silica gel with 75% MeOH/H$_2$O. Fractions containing product were pooled and evaporated to yield a white solid which was recrystallized from MeOH and H$_2$O to yield 43 mg (47%) of 4.137 as a pale tan powder: mp 210-211° C.; $R_f$ 0.2 (10% MeOH/CHCl$_3$); $^1$H-NMR (500 MHz, DMSO-d$_6$): δ 9.95 (s, 1H), 8.69 (s, 1H), 8.28 (s, 1H), 6.06 (d, 1H), 5.49-5.43 (m, 2H, D$_2$O exch.), 5.31 (d, 1H, D$_2$O exch.), 4.44 (q, 1H), 4.18 (m, 1H), 4.04 (d, 1H), 3.77-3.71 (m, 2H). $^{13}$C-NMR (125 MHz, DMSO-d$_6$): δ 185.53, 134.05, 128.85, 126.58, 126.47, 125.31, 120.56, 116.00, 114.68, 90.27, 86.55, 71.69, 69.62, 60.98. HRMS (EI) m/z calcd. for C$_{14}$H$_{12}$BrCl$_2$NO$_5$ 422.9276, found 422.9271. Anal calcd for C$_{14}$H$_{12}$BrCl$_2$NO$_5$: C, 39.56; H, 2.85; N, 3.30. Found: C, 39.77; H, 3.03; N, 3.32.

5,6-Dichloro-2-bromo-3-cyano-1-(5-O-acetyl-β-D-ribofuranosyl)indole (4.139)

5,6-Dichloro-2-bromo-3-cyano-1-(2,3-O-isopropylidene-5-O-acetyl-β-D-ribofuranosyl)indole (4.138, 184 mg, 0.36 mmol) was dissolved in 90% aqueous trifluoroacetic acid (5 mL). The resulting solution was stirred at room temperature for 2 min, then evaporated to approx 1 mL. The remaining solution was poured into 10% aqueous NaHCO$_3$ (50 mL). The aqueous suspension was extracted with EtOAc (2×50 mL), and the combined organic extracts were dried over MgSO$_4$, filtered and evaporated to yield a white solid. The solid was recrystallized from boiling EtOAc and hexane to yield 149 mg (88%) of 4.139 as a white crystalline solid: mp 103-105° C.; $R_f$ 0.5 (10% MeOH/CHCl$_3$); $^1$H-NMR (500 MHz, DMSO-d$_6$): δ 8.04 (s, 1H), 7.97 (s, 1H), 5.97 (d, 1H), 5.58 (d, 1H, D$_2$O exch.), 5.48 (d, 1H, D$_2$O exch.), 4.48 (dd, 1H), 4.39 (q, 1H), 4.27 (dd, 1H), 4.18 (q, 1H), 4.14 (m, 1H), 2.16 (s, 3H). $^{13}$C-NMR (125 MHz, DMSO-d$_6$): δ 170.24, 132.95, 126.92, 126.81, 126.54, 125.65, 119.79, 114.75, 113.63, 91.19, 90.20, 82.81, 71.62, 68.85, 63.40, 20.84.

5,6-Dichloro-2-bromo-1-(β-D-ribofuranosyl)indole-3-carboxamide oxime (4.140)

A solution of hydroxylamine in absolute MeOH was prepared by adding potassium hydroxide (1.83 g, 33 mmol) to hydroxylamine hydrochloride (2.50 g, 36 mmol) dissolved in absolute MeOH (20 mL) and stirring for 10 min. The resulting solids were filtered and rinsed with cold absolute MeOH (10 mL), and the filtrate used without further purification. 5,6-Dichloro-2-bromo-3-cyano-1-(5-O-acetyl-β-D-ribofuranosyl)indole (4.139, 133 mg, 0.29 mmol) was dissolved in the crude solution of hydroxylamine in MeOH and stirred at room temperature for 4 days. The solvent was then removed under vacuum, and the residual solid dissolved in brine (40 mL). The aqueous suspension was extracted with EtOAc (2×50 mL), and the combined organic extracts dried over MgSO$_4$, filtered and evaporated to yield a pale yellow solid. The solid was dissolved in MeOH (1 mL) and subjected to column chromatography (40×350 mm) on silica gel with 20% MeOH/CHCl$_3$. Fractions containing product were pooled and evaporated to yield a pale yellow solid. The solid was dissolved in MeOH (1 mL) and subjected to column chromatography (40×350 mm) on C18-reverse phase silica gel with 75% MeOH/H$_2$O. Fractions containing product were pooled and evaporated to yield a pale yellow solid which was recrystallized from MeOH/H$_2$O to yield 54 mg (41%) of 4.140 as a pale yellow powder: mp slow dec >170 □C; $R_f$ 0.5 (20% MeOH/CHCl$_3$); $^1$H-NMR (500 MHz, DMSO-d$_6$): δ 9.66 (s, 1H, D$_2$O exch.), 8.48 (s, 1H), 7.89 (s, 1H), 5.99 (d, 1H), 5.76 (s, 2H, D$_2$O exch.), 5.35 (t, 1H, D$_2$O exch.), 5.31 (d, 1H, D$_2$O exch.), 5.22 (d, 1H, D$_2$O exch.), 4.45 (q, 1H), 4.15 (t, 1H), 3.96 (d, 1H), 3.72 (m, 2H). $^{13}$C-NMR (125 MHz, DMSO-d$_6$): δ 146.18, 133.16, 127.04, 124.88, 123.77, 120.74, 115.72, 114.86, 110.61, 90.17, 85.68, 71.21, 69.55, 61.07. HRMS (ES) m/z calcd. for C$_{14}$H$_{14}$BrCl$_2$N$_3$O$_5$+H 453.9572, found 453.9570. Anal calcd for C$_{14}$H$_{14}$BrCl$_2$N$_3$O$_5$·¼MeOH: C, 36.96; H, 3.26; N, 9.07. Found: C, 37.11; H, 3.22; N, 8.85.

5,6-Dichloro-2-bromo-3-acetyl-1-(2-deoxy-β-D-ribofuranosyl)indole (4.143)

5,6-Dichloro-2-bromo-3-acetyl-1-[3,5-di-O-(p-toluoyl)-2-deoxy-β-D-ribofuranosyl]indole (4.142, 1.24 g, 1.7 mmol) was suspended in absolute MeOH (75 mL) to which was added sodium methoxide (250 mg, 4.6 mmol). The suspension was stirred at room temperature for 2 h, after which time the solution first clarified and then a precipitate formed. Water (100 mL) was added, and the suspension was evaporated until no more MeOH remained. The remaining solids were filtered and recrystallized twice from MeOH/H$_2$O to yield 475 mg (68%) of 4.143 as a white crystalline solid: mp slow dec. >235° C.; $R_f$ 0.5 (10% MeOH/CHCl$_3$); $^1$H-NMR (500 MHz, DMSO-d$_6$): δ 8.57 (s, 1H), 8.37 (s, 1H), 6.56 (dd, 1H), 5.46 (s, 1H, D$_2$O exch.), 5.31 (s, 1H, D$_2$O exch.), 4.48 (d, 1H), 3.92 (d, 1H), 3.76 (s, 2H), 2.65 (s, 3H), 2.48 (m, 1H), 2.13 (ddd, 1H). $^{13}$C-NMR (125 MHz, DMSO-d$_6$): δ 192.59, 133.20, 126.74, 125.89, 125.77, 121.91, 121.80, 115.94, 115.32, 87.59, 87.30, 69.84, 60.66, 39.23 (under DMSO), 30.95. HRMS (EI) m/z calcd. for C$_{15}$H$_{14}$BrCl$_2$NO$_4$ 420.9483, found 420.9493. Anal calcd for C$_{15}$H$_{14}$BrCl$_2$NO$_4$: C, 42.58; H, 3.34; N, 3.31. Found: C, 42.77; H, 3.25; N, 3.22.

B. Biological Evaluation.

Cell culture procedures. The routine growth and passage of KB, BSC-1, and HFF cells was performed in monolayer cultures using minimal essential medium (MEM) with either Hanks salts [MEM(H)] or Earle salts [MEM(E)] supplemented with 10% calf serum or 10% fetal bovine serum (HFF cells). The sodium bicarbonate concentration was varied to meet the buffering capacity required. Cells were passaged at 1:2 to 1:10 dilutions according to conventional procedures by using 0.05% trypsin plus 0.02% EDTA in a HEPES buffered salt solution.[30]

Virological procedures. The Towne strain, plaque-purified isolate P$_o$, of HCMV was kindly provided by Dr. Mark Stinski, University of Iowa. The KOS strain of HSV-1 was used in most experiments and was provided by Dr. Sandra K. Weller, University of Connecticut. Stock HCMV was prepared by infecting HFF cells at a multiplicity of infection (m.o.i.) of <0.01 plaque-forming units (p.f.u.) per cell as detailed previously (Turk, et al., Agents Chemother. 1987, 31, 544-550, herein incorporated by reference). High titer HSV-1 stocks were prepared by infecting KB cells at an m.o.i. of <0.1 also as detailed previously (see Turk et al.). Virus titers were determined using monolayer cultures of HFF cells for HCMV and monolayer cultures of BSC-1 cells for HSV-1 as described earlier (Prichard, et al., J. Virol. Methods 1990, 28, 101-106, herein incorporated by reference). Briefly, HFF or BSC-1 cells were planted as described above in 96-well cluster dishes and incubated overnight at 37° C. The next day cultures were inoculated with HCMV or HSV-1 and serially diluted 1:3 across the remaining eleven columns of the 96-well plate. After virus adsorption the inoculum was replaced with fresh medium and cultures were incubated for seven days for HCMV, two or three days for HSV-1. Plaques were enumerated under 20-fold magnification in wells having the dilution which gave 5 to 20 plaques per well. Virus titers were calculated according to the following formula: Titer (p.f.u./mL)=number of plaques×5×3$^n$; where n represents the n$^{th}$ dilution of the virus used to infect the well in which plaques were enumerated.

HCMV plaque reduction assay. HFF cells in 24-well cluster dishes were infected with approximately 100 p.f.u. of HCMV per cm$^2$ cell sheet using the procedures detailed above. Following virus adsorption, the compounds, prepared as 10 mg/mL stock solutions in DMSO were diluted with growth medium and were added to duplicate wells in four to eight selected concentrations. After incubation at 37° C. for 7-10 days, cell sheets were fixed, stained with crystal violet and microscopic plaques enumerated as described above. Drug effects were calculated as a percentage of reduction in number of plaques in the presence of each drug concentration compared to the number observed in the absence of drug.

HSV-1 ELISA. An ELISA was employed (Prichard, et al., Antiviral Res. 1990, 14, 181-206, herein incorporated by reference) to detect HSV-1. Ninety-six-well cluster dishes were planted with 10,000 BSC-1 cells per well in 200 µL per well of MEM(E) plus 10% calf serum. After overnight incubation at 37° C., selected drug concentrations in quadruplicate and HSV-1 at a concentration of 100 p.f.u./well were added. Following a 3-day incubation at 37° C., medium was removed, plates were blocked, rinsed, and horse radish peroxidase conjugated rabbit anti-HSV-I antibody was added. Following removal of the antibody containing solution, plates were rinsed, and then developed by adding 150 µL per well of a solution of tetramethylbenzidine as substrate. The reaction was stopped with H$_2$SO$_4$ and absorbance was read at 450 and 570 nm. Drug effects were calculated as a percentage of the reduction in absorbance in the presence of each drug concentration compared to absorbance obtained with virus in the absence of drug.

Cytotoxicity assays. Two different assays were used for routine cytotoxicity testing. (i) Cytotoxicity produced in stationary HFF cells was determined by microscopic inspection of cells not affected by the virus used in plaque assays (Turk, et al., Agents Chemother. 1987, 31, 544-550, herein incorporated by reference). (ii) The effect of compounds during two population doublings of KB cells was determined by crystal violet staining and spectrophotometric quantitation of dye eluted from stained cells as described earlier (Prichard, et al., Antiviral Res. 1991, 35, 1060-1065, herein incorporated by reference). Briefly, 96-well cluster dishes were planted with KB cells at 3000-5000 cells per well. After overnight incubation at 37° C., test compound was added in quadruplicate at six to eight concentrations. Plates were incubated at 37° C. for 48 h in a CO$_2$ incubator, rinsed, fixed with 95% ethanol, and stained with 0.1% crystal violet. Acidified ethanol was added and plates read at 570 nm in a spectrophotometer designed to read 96-well ELISA assay plates.

Data Analysis. Dose response relationships were used to quantitate drug effects by linear regression of the percent inhibition of parameters derived in the preceding assays against logio drug concentrations. Fifty percent inhibitory concentrations (IC$_{50}$'s) were calculated from the linear portions of the regression lines. Samples containing positive controls (acyclovir for HSV-1, GCV for HCMV, and 2-acetylpyridine thiosemicarbazone for cytotoxicity) were used in all assays.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in relevant fields are intended to be within the scope of the following claims.

We claim:

1. A compound as depicted in formula (I), wherein formula (I) is as follows:

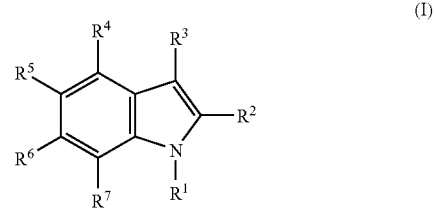

wherein:
R$^1$ is i) a substituent selected from: 1-D- or 1-L-ribosyl; ii) the 2-deoxy derivative of said substituent; or iii) the α or β-anomer of said substituent;
R$^2$ is NR$^8$R$^9$ where R$^8$=R$^9$=H, CH$_3$, C$_2$H$_5$ isopropyl, or cyclopropyl; halogen, chloro, or bromo; —O—R$^{10}$ where R$^{10}$=CH$_3$, C$_2$H$_5$, or CH$_2$C$_6$H$_5$; or —S—R$^{11}$ where R$^{11}$=H, CH$_3$, C$_2$H$_5$, or CH$_2$C$_6$H$_5$;
R$^3$ is; —CXNH$_2$ where X is =S, =NOH, or =N—NH$_2$; —CR=O where R is CH$_3$, C$_2$H$_5$, or C$_3$H$_7$; or —CH$_2$— RC=O where R is H, CH$_3$, C$_2$H$_5$, or C$_3$H$_7$; and
R$^4$—R$^7$ are selected from Cl, Br, F, I, a nitro group, and an azido group.

2. A pharmaceutical composition comprising a compound of claim 1 and a pharmaceutically acceptable carrier or a pharmaceutically acceptable excipients.

3. A compound as depicted in formula (I), wherein formula (I) is as follows:

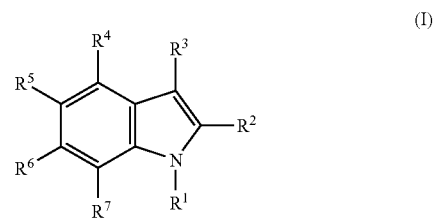

wherein:
- $R^1$ is D-ribofuranosyl, 2'-deoxy-D-ribofuranosyl, or 5'-O-acetyl-D-ribofuranosyl,
- $R^2$ is —$NR^8R^9$ where $R^8$=$R^9$=H, $CH_3$, $C_2H_5$, or when $R^8$=H, $R^9$=isopropyl or cyclopropyl; where $R^2$=Cl, or Br;
- $R^3$ is; —$CXNH_2$ where X is =S, =NOH, or =N—HN—R; —RC=O where R=H, $CH_3$, $C_2H_5$, or $C_3H_7$; or $R^3$ is thienyl or furanyl; and
- $R^4$=$R^7$ are exocyclic groups selected from chloro, bromo, hydrogen and nitro.

4. A pharmaceutical composition comprising a compound of claim 3 and a pharmaceutically acceptable carrier or a pharmaceutically acceptable excipients.

5. The compound of claim 1, wherein said compound is selected from the group consisting of

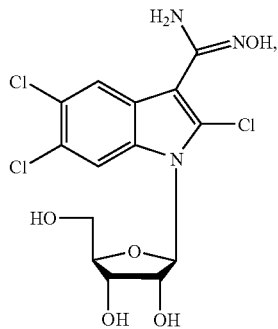
4.33

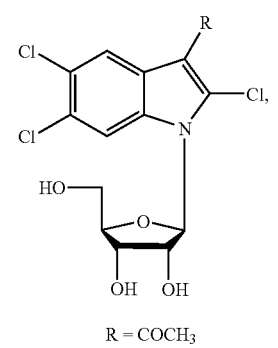
4.46
R = COCH₃

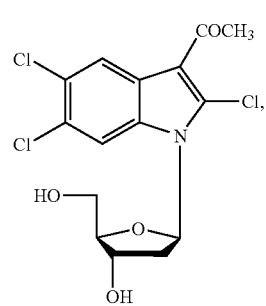
4.117

-continued

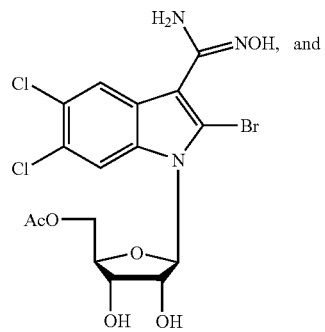
4.140

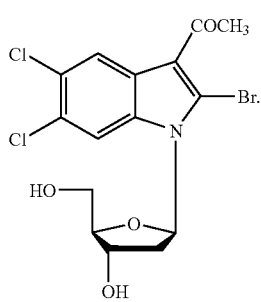
4.143

6. The compound of claim 1, wherein said compound is selected from the group consisting of

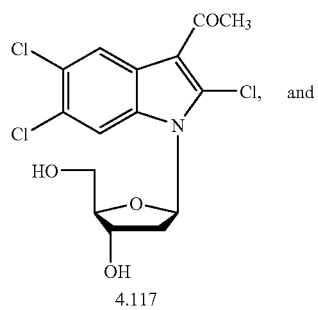
4.117

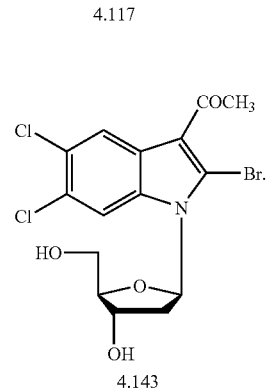
4.143

7. The compound of claim 3, wherein said compound is selected from the group consisting of

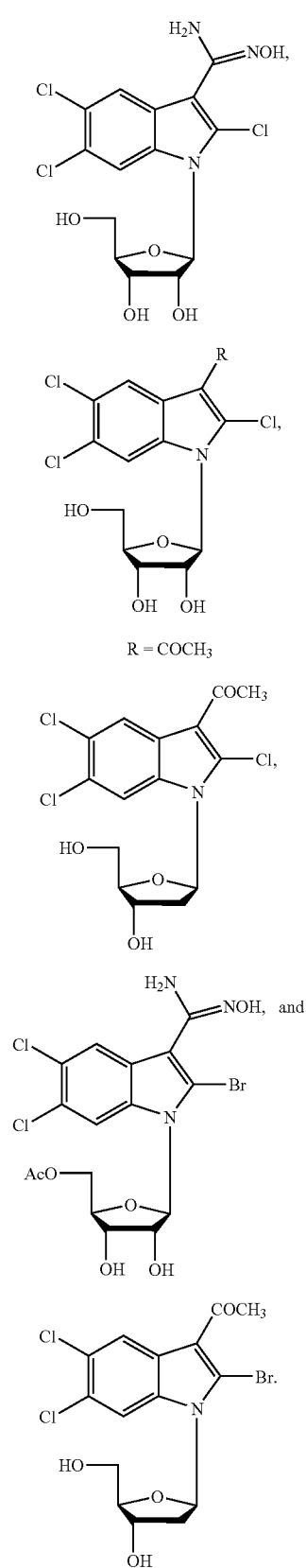

8. The compound of claim 3, wherein said compound is selected from the group consisting of

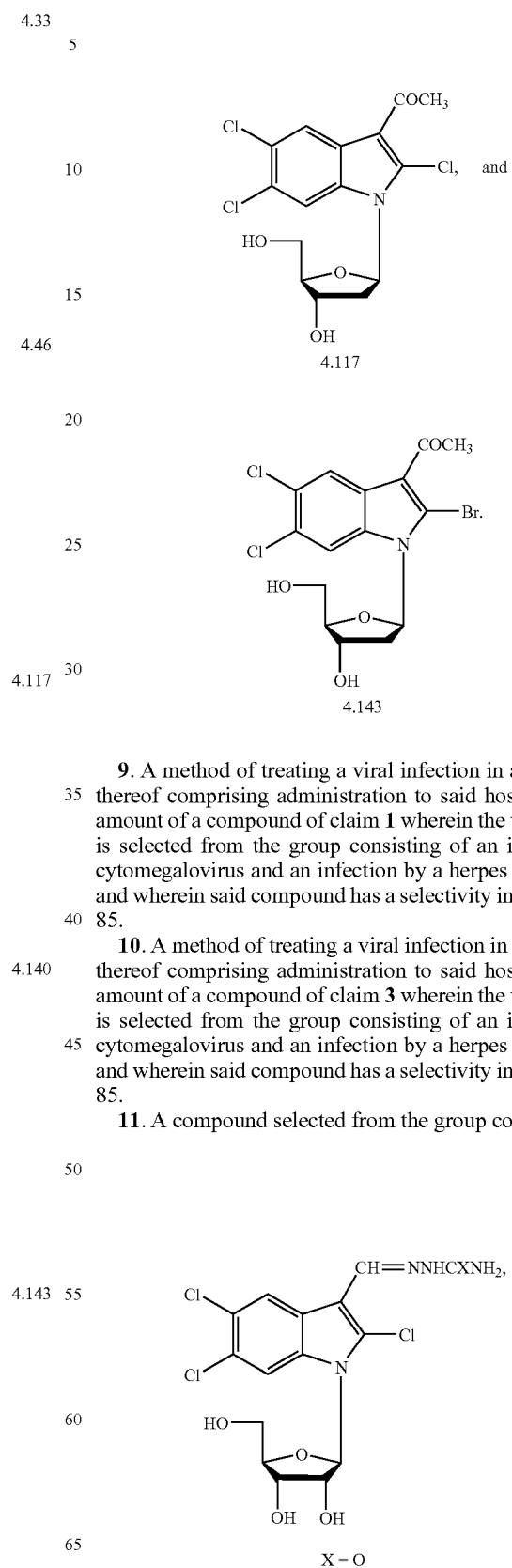

9. A method of treating a viral infection in a host in need thereof comprising administration to said host an effective amount of a compound of claim 1 wherein the viral infection is selected from the group consisting of an infection by a cytomegalovirus and an infection by a herpes simplex virus and wherein said compound has a selectivity index of at least 85.

10. A method of treating a viral infection in a host in need thereof comprising administration to said host an effective amount of a compound of claim 3 wherein the viral infection is selected from the group consisting of an infection by a cytomegalovirus and an infection by a herpes simplex virus and wherein said compound has a selectivity index of at least 85.

11. A compound selected from the group consisting of

-continued
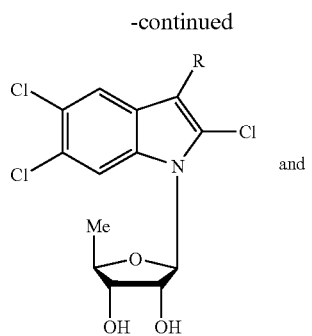
(4.97)
R = CHO
and
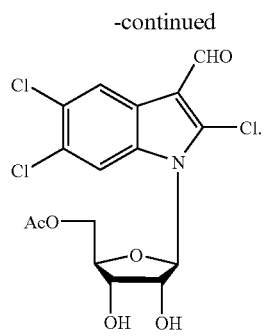
(4.122)
* * * * *

UNITED STATES PATENT AND TRADEMARK OFFICE
CERTIFICATE OF CORRECTION

PATENT NO. : 7,419,963 B2 Page 1 of 1
APPLICATION NO. : 10/959885
DATED : September 2, 2008
INVENTOR(S) : Leroy B. Townsend et al.

It is certified that error appears in the above-identified patent and that said Letters Patent is hereby corrected as shown below:

Title Page, insert item
--(73) Assignee: The Regents of the University of Michigan, Ann Arbor, MI (US)--

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,419,963 B2 Page 1 of 1
APPLICATION NO. : 10/959885
DATED : September 2, 2008
INVENTOR(S) : Leroy B. Townsend and John C. Drach It is certified that error appears in the above-identified patent and that said Letters Patent is hereby corrected as shown below:

Claim 3, Column 45, line 11 should read --$R^4$-$R^7$ are exocyclic groups selected from chloro, bromo,--

Signed and Sealed this

Third Day of August, 2010

David J. Kappos
*Director of the United States Patent and Trademark Office*